US006984645B2

(12) United States Patent
Magnin et al.

(10) Patent No.: US 6,984,645 B2
(45) Date of Patent: Jan. 10, 2006

(54) DUAL INHIBITORS OF ADIPOCYTE FATTY ACID BINDING PROTEIN AND KERATINOCYTE FATTY ACID BINDING PROTEIN

(75) Inventors: David R. Magnin, Hamilton, NJ (US); Richard B. Sulsky, West Trenton, NJ (US); Jeffrey A. Robl, Newtown, PA (US); Thomas J. Caulfield, Paris (FR); Rex A. Parker, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 233 days.

(21) Appl. No.: 10/295,819

(22) Filed: Nov. 15, 2002

(65) Prior Publication Data

US 2003/0225091 A1 Dec. 4, 2003

Related U.S. Application Data

(60) Provisional application No. 60/333,194, filed on Nov. 16, 2001.

(51) Int. Cl.
   A61K 31/435 (2006.01)
   A61K 31/19 (2006.01)
   A61K 31/195 (2006.01)
   C07D 233/54 (2006.01)
   C07D 65/03 (2006.01)

(52) U.S. Cl. ............... 514/277; 514/358; 514/400; 514/563; 514/568; 546/342; 546/347; 548/341.5; 562/476

(58) Field of Classification Search ............... 514/277, 514/358, 400, 563, 568; 546/342, 347; 548/341.5; 562/476
   See application file for complete search history.

(56) References Cited

U.S. PATENT DOCUMENTS

| 3,674,836 | A | 7/1972 | Creger |
| 3,983,140 | A | 9/1976 | Endo et al. |
| 4,027,009 | A | 5/1977 | Grier et al. |
| 4,046,889 | A | 9/1977 | Ondetti et al. |
| 4,231,938 | A | 11/1980 | Monaghan et al. |
| 4,316,906 | A | 2/1982 | Ondetti et al. |
| 4,337,201 | A | 6/1982 | Petrillo, Jr. |
| 4,344,949 | A | 8/1982 | Hoefle et al. |
| 4,346,227 | A | 8/1982 | Terahara et al. |
| 4,374,829 | A | 2/1983 | Harris et al. |
| 4,432,971 | A | 2/1984 | Karanewsky et al. |
| 4,448,784 | A | 5/1984 | Glamkowski et al. |
| 4,450,171 | A | 5/1984 | Hoffman et al. |
| 4,452,790 | A | 6/1984 | Karanewsky et al. |
| 4,473,575 | A | 9/1984 | Watthey |
| 4,499,289 | A | 2/1985 | Baran et al. |
| 4,572,912 | A | 2/1986 | Yoshioka et al. |

(Continued)

FOREIGN PATENT DOCUMENTS

| DE | 19622222 | 12/1997 |
| EP | 060668 | 9/1982 |
| EP | 079022 | 5/1983 |
| EP | 080822 | 6/1983 |
| EP | 142146 | 5/1985 |
| EP | 221025 | 5/1987 |
| EP | 481522 | 4/1992 |
| EP | 534363 | 3/1993 |
| EP | 534396 | 3/1993 |
| EP | 534492 | 3/1993 |
| EP | 595610 | 5/1994 |
| EP | 599444 | 6/1994 |
| EP | 629627 | 12/1994 |
| EP | 675714 | 10/1995 |
| FR | 2596393 | 10/1987 |
| GB | 2103614 | 2/1983 |
| GB | 2304106 | 3/1997 |

(Continued)

OTHER PUBLICATIONS

US 4,385,051, 5/1983, Oka et al. (withdrawn)

Ashworth, D.M. et al., "2–Cyanopyrrolidides as Potent, Stable Inhibitors of Dipeptidyl Peptidase IV", Bioorganic & Medicinial Chemistry Letters, vol. 6, No. 10, pp. 1163–1166 (1996).

Ashworth, D.M. et al., "4–Cyanothiazolidides as Very Potent, Stable Inhibitors of Dipeptidyl Peptidase IV", Bioorganic & Medicinial Chemistry Letters, vol. 6, No. 22, pp. 2745–2748 (1996).

Attwood, M.R. et al., "New potent inhibitors of angiotensin converting enzyme", FEBS, vol. 165, No. 2, pp. 201–206 (1984).

Baum, T. et al., "Antihypertensive Activity of SCH 31846, a Non–Sulfhydryl Angiotensin–Converting Enzyme Inhibitor", Journal of Cardiovascular Pharmacology, vol. 5, No. 4, pp. 655–667 (1983).

(Continued)

Primary Examiner—Paul A. Zucker
(74) Attorney, Agent, or Firm—Joseph C. Wang; Laurelee A. Duncan

(57) ABSTRACT

Compounds that are dual aP2/k-FABP inhibitors are provided having the formula

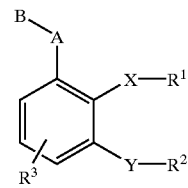

wherein A, B, X, Y, $R^1$, $R^2$ and $R^3$ are as described herein. A method is also provided for treating diabetes and related diseases, especially Type II diabetes, employing dual aP2/k-FABP inhibitors alone or in combination with at least one other antidiabetic agent such as metformin, glyburide, troglitazone and/or insulin.

14 Claims, No Drawings

U.S. PATENT DOCUMENTS

| | | |
|---|---|---|
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,722,810 A | 2/1988 | Delaney et al. |
| 4,749,688 A | 6/1988 | Haslanger et al. |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,223,516 A | 6/1993 | Delaney et al. |
| 5,225,401 A | 7/1993 | Seymour |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,362,727 A | 11/1994 | Robl |
| 5,366,973 A | 11/1994 | Flynn et al. |
| 5,385,929 A | 1/1995 | Bjorge et al. |
| 5,447,954 A | 9/1995 | Gribble et al. |
| 5,488,064 A | 1/1996 | Sher |
| 5,491,134 A | 2/1996 | Sher et al. |
| 5,504,080 A | 4/1996 | Karanewsky |
| 5,506,219 A | 4/1996 | Robl |
| 5,525,723 A | 6/1996 | Robl |
| 5,541,204 A | 7/1996 | Sher et al. |
| 5,552,397 A | 9/1996 | Karanewsky et al. |
| 5,594,016 A | 1/1997 | Ueno et al. |
| 5,595,872 A | 1/1997 | Wetterau, II et al. |
| 5,612,359 A | 3/1997 | Murugesan |
| 5,614,492 A | 3/1997 | Habener |
| 5,631,224 A | 5/1997 | Efendic et al. |
| 5,686,104 A | 11/1997 | Mills et al. |
| 5,691,322 A | 11/1997 | Robl |
| 5,698,527 A | 12/1997 | Kim |
| 5,712,279 A | 1/1998 | Biller et al. |
| 5,712,396 A | 1/1998 | Magnin et al. |
| 5,739,135 A | 4/1998 | Biller et al. |
| 5,753,675 A | 5/1998 | Wattanasin |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,962,440 A | 10/1999 | Sulsky |
| 6,218,408 B1 | 4/2001 | Marzabadi et al. |
| 6,395,767 B2 | 5/2002 | Robl et al. |
| 6,414,002 B1 | 7/2002 | Cheng et al. |
| 6,414,126 B1 | 7/2002 | Ellsworth et al. |

FOREIGN PATENT DOCUMENTS

| | | |
|---|---|---|
| WO | WO 86/03488 | 6/1986 |
| WO | WO 86/07054 | 12/1986 |
| WO | WO 94/15592 | 7/1994 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 99/38501 | 8/1999 |
| WO | WO 99/46272 | 9/1999 |
| WO | WO 99/58518 | 11/1999 |
| WO | WO 99/58522 | 11/1999 |
| WO | WO 99/58552 | 11/1999 |
| WO | WO 99/61431 | 12/1999 |
| WO | WO 99/61435 | 12/1999 |
| WO | WO 99/67278 | 12/1999 |
| WO | WO 99/67279 | 12/1999 |
| WO | WO 00/15229 | 3/2000 |
| WO | WO 00/50574 | 8/2000 |
| WO | WO 00/59506 | 10/2000 |
| WO | WO 01/13917 | 3/2001 |
| WO | WO 01/14376 | 3/2001 |
| WO | WO 01/44239 | 6/2001 |
| WO | WO 01/60784 | 8/2001 |

OTHER PUBLICATIONS

Biller, S.A. et al., "Isoprenoid (Phosphinylmethyl)phosphonates as Inhibitors of Squalene Synthetase", Journal of Medicinal Chemistry, vol. 31, No. 10, pp. 1869–1871 (1988).

Biller, S.A. et al., "Squalene Synthase Inhibitors", Current Pharmaceutical Design, vol. 2, pp. 1–40 (1996).

Bristol–Myers Squibb Company newsletter, vol. 7, No. 3, pp. 20–21 (1996).

Capson, T.L., "Synthesis and Evaluation of Ammonium Analogs of Carbocationic Intermediates in Squalene Biosynthesis", dissertation, Department of Medicinal Chemistry, University of Utah, pp. iv–v, Table of Contents, 16–17, 40–43, 48–51, Summary (Jun. 1987).

Carlsson, A. et al., "In den Catecholamin–Metabolismus eingreifende Substanzen. 3. 2,3–Dihydroxyphenylacetamide und verwandte Verbindungen", Helvetica Chimica Acta, vol. 47, No. 5, pp. 1340–1349 (1964).

Chemical Abstracts, vol. 102, 72588v, p. 40 (1985).

Cohen, D.M. et al., "CI–925: A New Orally Active Non–sulfhydryl Angiotensin Converting Enzyme (ACE) Inhibitor" (53, 266), The Pharmacologist, FASEB Meeting Information, vol. 26, No. 1, p. 177 (1984).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", J. Am. Chem. Soc., vol. 98, No. 5, pp. 1291–1293 (1976).

Cornicelli, J.A. et al., "15–Lipoxygenase and Its Inhibition: A Novel Therapeutic Target for Vascular Disease", Current Pharmaceutical Design, vol. 5, pp. 11–20 (1999).

Easton, M.L. et al., "Metabolic disposition of CI–925–$^{14}$C, a potent ACE inhibitor in rats and dogs" (30, 243), The Pharmacologist, FASEB Meeting Information, vol. 26, No. 1, p. 172 (1984).

Ghiselli, G., "The Pharmacological Profile of FCE 27677: A Novel ACAT Inhibitor with Potent Hypolipidemic Activity Mediated by Selective Suppression of the Hepatic Secretion of ApoB–100–Containing Lipoprotein", Cardiovascular Drug Reviews, vol. 16, No. 1, pp. 16–30 (1998).

Hotamisligil, G.S. et al., "Uncoupling of Obesity from Insulin Resistance Through a Targeted Mutation in aP2, the Adipocyte Fatty Acid Binding Protein", Science, vol. 274, pp. 1377–1379 (1996).

Hughes, T.E. et al., "(1–[[[2–[(5–Cyanopyridin–2–yl)amino]ethyl]amino]acetyl]–2–cyano–(S)–pyrrolidine), a Slow–Binding Inhibitor of Dipeptidyl Peptidase IV", Biochemistry, vol. 38, pp. 11597–11603 (1999).

Kalra, A.J. et al., "Synthesis of Apuleidin, a Flavone from *Apuleia leiocarpa*", Indian Journal of Chemistry, vol. 13, pp. 18–19 (1975).

Kim, D.H. et al., "Mercaptopropanoyl)indoline-2-carboxylic Acids and Related Compounds as Potent Angiotensin Converting Enzyme Inhibitors and Antihypertensive Agents", J. Med. Chem. vol. 26, pp. 394–403 (1983).

Krause, B.R. et al., "ACAT Inhibitors: Physiologic Mechanism for Hypolipidemic and Anti–Atherosclerotic Activities in Experimental Animals", Inflammation: Mediators Pathways, CRC Press, Inc., pp. 173–198 (1995).

Lees, K.R. et al., "The Haemodynamic and Humoral Effects of Treatment for One Month with the Angiotensin Converting Enzyme Inhibitor Perindopril in Salt Replete Hypertensive Patients", European Journal of Clinical Pharmacology, vol. 31, pp. 519–524 (1987).

Makowski, L. et al., "Lack of macrophage fatty–acid–binding protein aP2 protects mice deficient in apolipoprotein E against atherosclerosis", Nature Medicine, vol. 7, No. 6, pp. 699–705 (2001).

McChesney, J.D. et al., "Simple Analogs of the Toxin Callicarpone", Journal of Pharmaceutical Sciences, vol. 68, No. 9, pp. 1116–1120 (1979).

McClard, R.W. et al., "Novel Phosphonylphosphinyl (P–C–P–C–) Analogues of Biochemically Interesting Diphosphates. Syntheses and Properties of P–C–P–C– Analogues of Isopentenyl Diphosphate and Dimethylallyl Diphosphate", J. Am. Chem. Soc., vol. 109, pp. 5544–5545 (1987).

Murakami, K. et al., "A Novel Insulin Sensitizer Acts as a Coligand for Peroxisome Proliferator–Activated Receptor–α (PPAR–α) and PPAR–γ., etc.", Diabetes, vol. 47, pp. 1841–1847 (1998).

Nicolosi, R.J. et al., "The ACAT Inhibitor, CI–1011 is effective in the prevention and regression of aortic fatty streak area in hamsters", Atherosclerosis, vol. 137, pp. 77–85 (1998).

Noguchi, K. et al., "Comparison of Acute Hemodynamic Effects of MC–838, a New Angiotensin–Converting Enzyme Inhibitor, with Captopril in Anesthetized Dogs", Japan, J. Pharmacol., vol. 40, pp. 373–380 (1986).

Nussberger, J. et al., "Repeated Administration of the Converting Enzyme Inhibitor Cilazapril to Normal Volunteers", Journal of Cardiovascular Pharmacology, vol. 9, pp. 39–44 (1987).

Onoyama, K. et al., "Pharmacokinetic Properties of a New Angiotensin I Converting Enzyme Inhibitor (Alacepril) in Normal Office Workers", Current Therapeutic Research, vol. 40, No. 3, pp. 543–550 (1986).

Onoyama, K. et al., "Pharmacokinetic Properties of a New Angiotensin I Converting Enzyme Inhibitor in Patients with Chronic Renal Failure", Current Therapeutic Research, vol. 39, No. 5, pp. 671–680 (1986).

Ortiz de Montellano, P.R. et al., "Inhibition of Squalene Synthetase by Farnesyl Pyrophosphate Analogues", Journal of Medicinal Chemistry, vol. 20, No. 2, pp. 243–249 (1977).

Perentesis, G. et al., "Multiple–Dose Efficacy and Tolerance of Spiropril (SCH 33844) in Mild/Moderate Hypertensive Patients" (1137), Acta Pharmacologica et Toxicologica, III World Conference on Clinical Pharmacology & Therpeutics, Abstracts II, vol. 59, Supp. V. p. 173 (1986).

Rosenblum, S.B. et al., "Discovery of 1–(4–Fluorophenyl)–(3R)–[3–(4–fluorophenyl)–(3S)–hydroxypropyl]–(4S)–(4–hydroxyphenyl)–2–azetidinone (SCH 58235): A Designed, Potent, Orally Active Inhibitor of Cholesterol Absorption", J. Med. Chem., vol. 41, pp. 973–980 (1998).

Salisbury, B.G. et al., "Hypocholesterolemic activity of a novel inhibitor of cholesterol absorption, SCH 48461", Atherosclerosis, vol. 115, pp. 45–63 (1995).

Schölinhammer, V.G. et al., "Biochemische Untersuchungen an Tienocarbin und verwandten Verbindungen", Arzneimittelforschung, vol. 34, pp. 1254–1258 (1985).

Sendobry, S.M. et al., "Attenuation of diet–induced atherosclerosis in rabbits with a highly selective 15–lipoxygenase inhibitor lacking significant antioxidant properties", British Journal of Pharmacology, vol. 120, pp. 1199–1206 (1997).

Shionoiri, H. et al., "Pharmacodynamics and Pharmacokinetics of Single–Dose Ramipril in Hypertensive Patients with Various Degrees of Renal Function", Current Therapeutic Research, vol. 40, No. 1, pp. 74–85 (1986).

Sliskovic, D.R. et al., "ACAT Inhibitors: Potential Anti–atherosclerotic Agents", Current Medicinal Chemistry, vol. 1, pp. 204–225 (1994).

Stout, D.M., "Inhibitors of Acyl–CoA:Cholesterol O–Acyl Transferase (ACAT) as Hypocholesterolemic Agents. 6. The First Water–Soluble ACAT Inhibitor with Lipid–Regulating Activity, etc.", Chemtracts–Organic Chemistry, vol. 8, pp. 359–362 (1995).

Sybertz, E.J. et al., "Angiotensin–Converting Enzyme Inhibitory Activity of SCH 31846, a New Non–Sulfhydryl Inhibitor", Journal of Cardiovascular Pharmacology, vol. 5, pp. 643–654 (1983).

Takata, Y. et al., "A Comparison of the Activity of the Angiotensin Converting Enzyme Inhibitors SQ 14 225, SA 446, and MK 421", Clinical and Experimental Pharmacology & Physiology, vol. 10, pp. 131–145 (1983).

"Treatment of Lipoprotein Disorders, ACAT Inhibitor" (Avasimibe), Drugs of the Future, vol. 24, No. 1, pp. 9–15 (1999).

Uysal, K.T. et al., "Improved Glucose and Lipid Metabolism in Genetically Obese Mice Lacking aP2", Endocrinology, vol. 141, No. 9, pp. 3388–3396 (2000).

Yamada, M. et al., "A Potent Dipeptide Inhibitor of Dipeptidyl Peptidase IV", Bioorganic & Medicinal Chemistry Letters, vol. 8, pp. 1537–1540 (1998).

DUAL INHIBITORS OF ADIPOCYTE FATTY ACID BINDING PROTEIN AND KERATINOCYTE FATTY ACID BINDING PROTEIN

This application claims priority to U.S. Provisional Application Ser. No. 60/333,194 filed Nov. 16, 2001, the entirety of which is incorporated herein by reference.

FIELD OF THE INVENTION

The present invention relates to inhibitors of the adipocyte fatty acid binding protein (aP2), and to dual inhibitors of aP2 and keratinocyte fatty acid binding protein (k-FABP), especially aryl carboxylic acids and tetrazoles of Formula I. The present invention further relates to a method for treating diabetes, especially Type II diabetes, as well as hyperglycemia, hyperinsulinemia, obesity, Syndrome X, diabetic complications, atherosclerosis and related diseases, and other chronic inflammatory and autoimmune/inflammatory diseases, employing the compounds of the present invention alone or in combination with one or more types of therapuetic agents.

BACKGROUND OF THE INVENTION

Fatty acid binding proteins (FABPs) are small cytoplasmic proteins that bind to fatty acids such as oleic acids which are important metabolic fuels and cellular regulators. Dysregulation of fatty acid metabolism in adipose tissue is a prominent feature of insulin resistance and the transition from obesity to non-insulin dependent diabetes mellitus (NIDDM or Type II diabetes).

aP2 (adipocyte fatty binding protein), an abundant 14.6 KDa cytosolic protein in adipocytes, and one of a family of homologous intracellular fatty acid binding proteins (FABPs), is involved in the regulation of fatty acid trafficking in adipocytes and mediates fatty acid fluxes in adipose tissue. G. S. Hotamisligil et al, "Uncoupling of Obesity from Insulin Resistance Through a Targeted Mutation in aP2, the Adipocyte Fatty Acid Binding Protein", Science, Vol. 274, Nov. 22, 1996, pp. 1377–1379, report that aP2-deficient mice placed on a high fat diet for several weeks developed dietary obesity, but, unlike control-mice on a similar diet, did not develop insulin resistance or diabetes. Hotamisligil et al conclude "aP2 is central to the pathway that links obesity to insulin resistance" (Abstract, page 1377).

Also, it has been shown by Uysal et al in "Improved glocose and lipid metabolism in genetically obese mice lacking aP2" in Endocrinology, Vol. 141, 2000, pp. 3388–3396 that ob/ob mice deficient of aP2 had lower plasma glucose, improved peripheral insulin resistance, and beneficial effects on lipid metabolism.

Additionally, Makowski et. al. in "Lack of macrophage fatty-acid-binding protein aP2 protects mice deficient in apolipoprotein E against atherosclerosis" in Nature Medicine, Vol. 7, 2001, pp. 699–705 showed that Apoe–/– mice with either total aP2 deficiency or aP2–/– macrophage deficiency showed reductions in the formation of atherosclerotic plague, as well as reduction of TNF-alpha and a variety of inflammatory cytokines, as compared to aP2 replete ApoE–/– mice.

Since it is known that both aP2 and k-FABP (mal-1), both intracellular fatty acid binding proteins, are expressed in both adipocyte and macrophage cells, concommitant inhibition of both FABPs should be expected to have greater effects in treating the diseases such as diabetes, obesity, atherosclerosis, inflammation, and those previously mentioned.

PCT applications WO 00/15229 and WO 00/59506 disclose methods for treating diabetes employing an aP2 inhibitor.

SUMMARY OF THE INVENTION

In accordance with the present invention, aryl compounds are provided which are aP2 inhibitors and/or dual aP2/k-FABP inhibitors having the structure of formula I

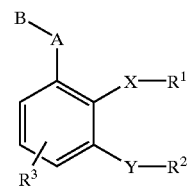

including pharmaceutically acceptable salts thereof, prodrug esters thereof, and all stereoisomers thereof wherein A is
  a bond,
  a $C_1$–$C_3$ alkylene group optionally independently substituted on available atoms with one to six halo, hydroxy, alkoxy, hydroxyalkyl, $SR^4$, alkyl, alkenyl, cyano, $CONHR^4$, $COOR^4$, oxo, $NHOR^4$, $=NOR^4$ or $N(R^8)COR^4$; or
  a $C_2$–$C_3$ alkenylene group optionally independently substituted on available atoms with one to four halo, hydroxy, alkoxy, hydroxyalkyl, $SR^4$, alkyl, alkenyl, cyano, $CONHR^4$, $COOR^4$, oxo, $NHOR^4$, $=NOR^4$, or $N(R^8)COR^4$;

B is carboxyl or tetrazole;

X and Y are independently
  —$O(CR^5R^6)_q$—,
  —$(CR^5R^6)_qO$—,
  —$(CR^5R^6)_qN(R^7)CO$—,
  —$N(R^7)CO(CR^5R^6)_q$—,
  —$N(R^7)CO(CR^5R^6)_qO$—,
  —$N(R^7)CO(CR^5R^6)_qC(O)O$—,
  —$N(R^7)CO$—$CR^5$=$CR^6$—,
  —$(CR^5R^6)_qN(R^7)SO_2$—,
  —$N(R^7)SO_2(CR^5R^6)_q$—,
  —$O$—$CO(CR^5R^6)_q$—,
  —$O(CR^5R^6)_qCO$—,
  —$(CR^5R^6)_qO$—$CO$—, or
  —$(CR^5R^6)_qS(O)_t$—;

$R^1$ is aryl, heteroaryl, alkyl, cycloalkyl, aralkyl, heteroarylalkyl, cylcoalkenyl or heterocyclo any of which may be optionally substituted with $Z^{1a}$, $Z^{2a}$ and one or more $Z^{3a}$;

$R^2$ is aryl, heteroaryl, alkyl, cycloalkyl, aralkyl, heteroarylalkyl, cylcoalkenyl or heterocyclo any of which may be optionally substituted with $Z^{1b}$, $Z^{2b}$ and one or more $Z^{3b}$;

$R^3$ is H, OH, alkyl, hydroxyalkyl, aryl, nitro, halo, amino, alkylamino, alkoxy, cyano, thioalkyl, carboxyl, $COOR^4$, $NR^7COR^4$, or $NR^7COOR^4$;

$R^4$ is
  (1) H; or
  (2) alkyl, haloalkyl (especially di- or trihaloalkyl), aminoalkyl, alkoxyalkyl, hydroxyalkyl, aryl or heteroaryl any of which may be optionally substituted with $Z^{1c}$, $Z^{2c}$ and one or more $Z^{3c}$;

$R^5$ and $R^6$ are independently
  (1) H, OH, halo, cyano or oxo; or
  (2) alkoxy, alkyl, alkenyl, hydroxyalkyl, aryl, aralkyl, heteroaryl, heteroarylalkyl, alkylthio, aryloxy or heteroaryloxy any of which may be optionally substituted with $Z^{1d}$, $Z^{2d}$ and one more $Z^{3d}$;

$R^7$ is
  (1) H, OH, or cyano; or
  (2) alkoxy, alkyl, alkenyl, hydroxyalkyl, aryl, aralkyl, heteroaryl, heteroarylalkyl, alkylthio, aryloxy or heteroaryloxy any of which may be optionally substituted with $Z^{1e}$, $Z^{2e}$ and one more $Z^{3e}$;

$R^8$ is
  (1) H, OH; or
  (2) alkyl, aryl, heteroaryl, alkoxy, aryloxy, or alkenyl any of which may be optionally subtituted with $Z^{1f}$, $Z^{2f}$ and one or more $Z^{3f}$;

t is 0, 1 or 2;
q is 0 to 5.
$Z^{1a-1f}$, $Z^{2a-2f}$, and $Z^{3a-3f}$ are optional substituents independently selected from
  (1) V, where V is
    (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
    (ii) a group (i) which is itself substituted by one or more of the same or different groups (i); or
    (iii) a group (i) or (ii) which is independently substituted by one or more (preferably 1 to 3) of the following groups (2) to (13) of the definition of $Z^{1a}$,
  (2) —OH or —OV,
  (3) —SH or —SV,
  (4) —C(O)$_p$H, —C(O)$_p$V, or —O—C(O)V, where p is 1 or 2,
  (5) —SO$_3$H, —S(O)$_p$V, or S(O)$_p$N(V$^1$)V,
  (6) halo,
  (7) cyano,
  (8) nitro,
  (9) —U$^1$—NV$^2$V$^3$,
  (10) —U$^1$—N(V$^1$)—U$^2$—NV$^2$V$^3$,
  (11) —U$^1$—N(V$^4$)—U$^2$—V,
  (12) —U$^1$—N(V$^4$)—U$^2$—H,
  (13) oxo;

$U^1$ and $U^2$ are each independently
  (1) a single bond,
  (2) —U$^3$—S(O)$_p$—U$^4$—,
  (3) —U$^3$—C(O)—U$^4$—,
  (4) —U$^3$—C(S)—U$^4$—,
  (5) —U$^3$—O—U$^4$—,
  (6) —U$^3$—S—U$^4$—,
  (7) —U$^3$—O—C(O)—U$^4$—,
  (8) —U$^3$—C(O)—O—U$^4$—,
  (9) —U$^3$C(=NV$^{1a}$)—U$^4$—, or
  (10) —U$^3$—C(O)—C(O)—U$^4$—;

$V^1$, $V^{1a}$, $V^2$, $V^3$ and $V^4$
  (1) are each independently hydrogen or a group provided in the definition of $Z^{1a}$; or
  (2) V$^2$ and V$^3$ may together be alkylene or alkenylene, completing a 3- to 8-membered saturated or unsaturated ring together with the atoms to which they are attached, which ring is unsubstituted or substituted with one or more groups listed in the definition of $Z^{1a}$; or
  (3) V$^2$ or V$^3$, together with V$^1$, may be alkylene or alkenylene completing a 3- to 8-membered saturated or unsaturated ring together with the nitrogen atoms to which they are attached, which ring is unsubstituted or substituted with one or more groups listed in the definition of $Z^{1a}$; or
  (4) V$^2$ and V$^3$ together with the nitrogen atom to which they are attached may combine to form a group —N=CV$^5$V$^6$ where V$^5$ and V$^6$ are each independently H or a group provided in the definition of V; and $U^3$ and $U^4$ are each independently
  (1) a single bond,
  (2) alkylene,
  (3) alkenylene, or
  (4) alkynylene.

In addition, in accordance with the present invention, a method is provided for treating diabetes, especially Type II diabetes, and related diseases such as insulin resistance, hyperglycemia, hyperinsulinemia, elevated blood levels of fatty acids or glycerol, obesity, hypertriglyceridemia, atherosclerosis, inflammation, diabetic retinopathy, diabetic neuropathy and diabetic nephropathy wherein a therapeutically effective amount of a compound of formula I is administered to a human patient in need of treatment.

In addition, in accordance with the present invention, a method is provided for treating diabetes and related diseases as defined above and hereinafter, wherein a therapeutically effective amount of a combination of a compound of formula I and another type antidiabetic agent is administered to a human patient in need of treatment.

In the above method of the invention, the compound of structure I will be employed in a weight ratio to another antidiabetic agent (depending upon its mode of operation) within the range from about 0.01:1 to about 100:1, preferably from about 0.5:1 to about 10:1.

Preferred compounds of formula I include compounds where
A is a bond, an optionally substituted $C_1$–$C_2$ alkylene group, or an optionally substituted $C_2$ alkenylene group;
B is carboxyl or tetrazole;
X and Y are independently —O(CR$^5$R$^6$)$_q$—, —(CR$^5$R$^6$)$_q$O—, —N(R$^7$)CO(CR$^5$R$^6$)$_q$—, —N(R$^7$)CO(CR$^5$R$^6$)$_q$O—, —N(R$^7$)CO(CR$^5$R$^6$)$_q$C(O)O—, —N(R$^7$)CO—CR$^5$=R$^6$—, —N(R$^7$)SO$_2$(CR$^5$R$^6$)$_q$—, or —O(CR$^5$R$^6$)$_q$CO—
where
  q is 0, 1 or 2;
  $R^1$ is aryl, heteroaryl (including N-oxides thereof), cycloalkyl or alkyl, any of which may be optionally substituted with $Z^{1a}$, $z^{2a}$ and one more $Z^{3a}$ (especially where $Z^{1a}$, $Z^{2a}$ and $Z^{3a}$ are independently halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl);
  $R^2$ is aryl, heteroaryl (including N-oxides thereof), cycloalkyl or alkyl, any of which may be optionally substituted with $Z^{1b}$, $Z^{2b}$ and one more $Z^{3b}$ (especially where $Z^{1b}$, $Z^{2b}$ and $Z^{3b}$ are independently halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl);
  $R^3$ is H, OH, halo, alkyl, haloalkyl or hydroxyalkyl;
  $R^5$ and $R^6$ are independently
    (1) H or OH; or (2) alkyl, aryl, aralkyl or heteroarylalkyl any of which may be optionally substituted with $Z^{1d}$, $Z^{2d}$ and one or more $Z^{3d}$; and $R^7$ is
(1) H or OH; or
(2) alkyl, aryl, aralkyl or heteroarylalkyl any of which may be optionally substituted with $Z^{1e}$, $Z^{2e}$ and one or more $Z^{3e}$.

More preferred compounds of formula I include compounds where

A is a bond, or a $C_1$–$C_2$ alkylene group optionally substituted with one OH, SH, $NH_2$, or =$NHOR^4$, or optionally substituted with at least one $COOR^4$, halogen or oxo;

B is carboxyl or prodrug ester thereof;

X and Y are independently —$O(CR^5R^6)_q$—, —$(CR^5R^6)_qO$—, —$N(R^7)CO(CR^5R^6)_q$—, or —$N(R^7)SO_2(CR^5R^6)_q$—
where
q is 0 or 1, and $R^1$ is aryl (preferably phenyl, napthyl, benzodioxolyl, benzodioxinyl, or anthracenyl), heteroaryl (including N-oxides thereof) (preferably, (pyridinyl, benzimidazolyl, quinoxalinyl, furanyl, thienyl, benzothiophenyl, or isothiozolyl) or, $C_3$–$C_6$ cycloalkyl any of which may be optionally substituted with one or more $Z^{1a}$, $Z^{2a}$ and one or more $Z^{3a}$ (especially where $Z^{1a}$, $Z^{2a}$ and $Z^{3a}$ are selected from halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl);

$R^2$ is aryl (preferably phenyl, napthyl, benzodioxolyl, benzodioxinyl, or anthracenyl), heteroaryl (including N-oxides thereof) (preferably, (pyridinyl, benzimidazolyl, quinoxalinyl, furanyl, thienyl, benzothiophenyl, or isothiozolyl) or, $C_3$–$C_6$ cycloalkyl any of which may be optionally substituted with one or more $Z^{1b}$, $Z^{2b}$ and one or more $Z^{3b}$ (especially where $Z^{1b}$, $Z^{2b}$ and $Z^{3b}$ are selected from halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl);

$R^3$ is H, OH, halo, alkyl, or haloalkyl;

$R^5$ and $R^6$ are independently
(1) H; or
(2) alkyl, aralkyl, or heteroarylalkyl any of which may be optionally substituted with $Z^{1d}$, $Z^{2d}$ and one or more $Z^{3d}$; and $R^7$ is
(1) H; or
(2) alkyl, aralkyl, or heteroarylalkyl any of which may be optionally substituted with $Z^{1d}$, $Z^{2d}$ and one or more $Z^{3d}$.

Most preferred compounds of formula I include compounds where

A is a hydroxy-substituted $C_1$ alkylene group (preferably the (S) isomer);

B is carboxyl;

X and Y are —$O(CR^5R^6)_q$—,
where
q is 1, and $R^1$ is phenyl or pyridinyl either of which may be optionally substituted with $Z^{1a}$, $Z^{2a}$ and one or more $Z^{3a}$ (especially where $Z^{1a}$, $Z^{2a}$ and $Z^{3a}$ are selected from halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl);

$R^2$ is phenyl optionally substituted with $Z^{1b}$, $Z^{2b}$ and one or more $Z^{3b}$ (especially where $Z^{1b}$, $Z^{2b}$ and $Z^{3b}$ are selected from one or more halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl);

$R^3$ is H, or halo; and $R^5$ and $R^6$ are H;

DETAILED DESCRIPTION OF THE INVENTION

Compounds of the invention of general structure I may be synthesized as illustrated generically in the schemes set forth below, and as further illustrated by the examples set forth herein.

Scheme 1

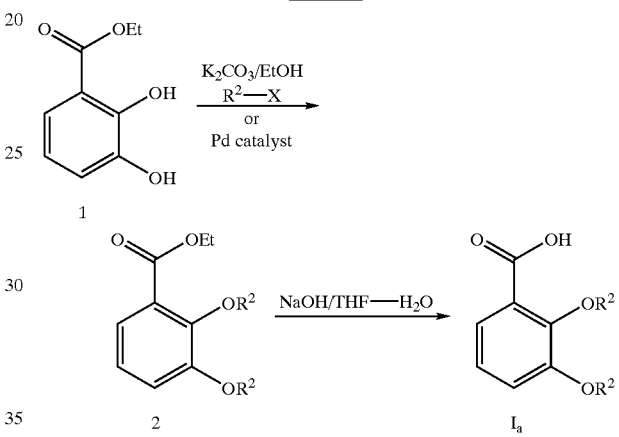

Benzoate 1 is converted to bis ether 2 by reaction with an appropriate halide. Saponification provides compound $I_a$.

Scheme 2

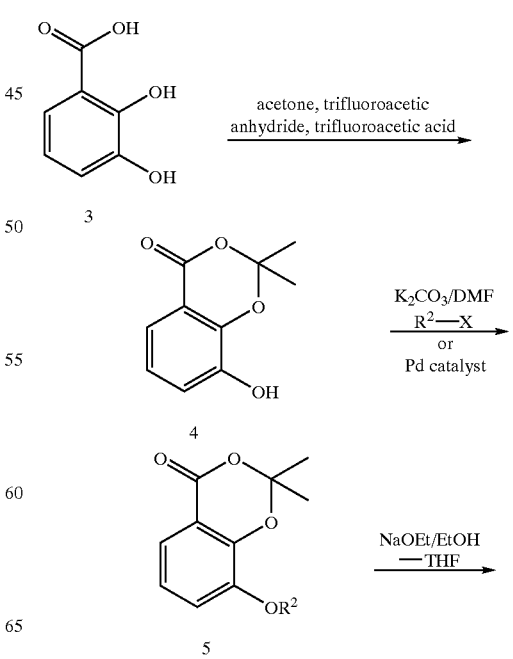

7
-continued
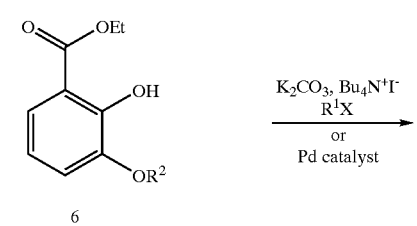
6
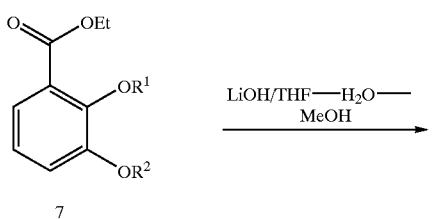
7
8
-continued
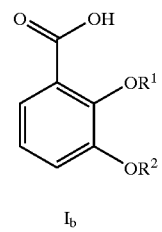
I_b
Alternatively, catechol 3 can be monoprotected to provide phenol ether 4 and reacted with an appropriate halide to provide 5. Transesterification of 5 with sodium ethoxide gives phenol 6 which is reacted with an appropriate halide, resulting in ester 7. Saponification as before provided I_b.
Scheme 3
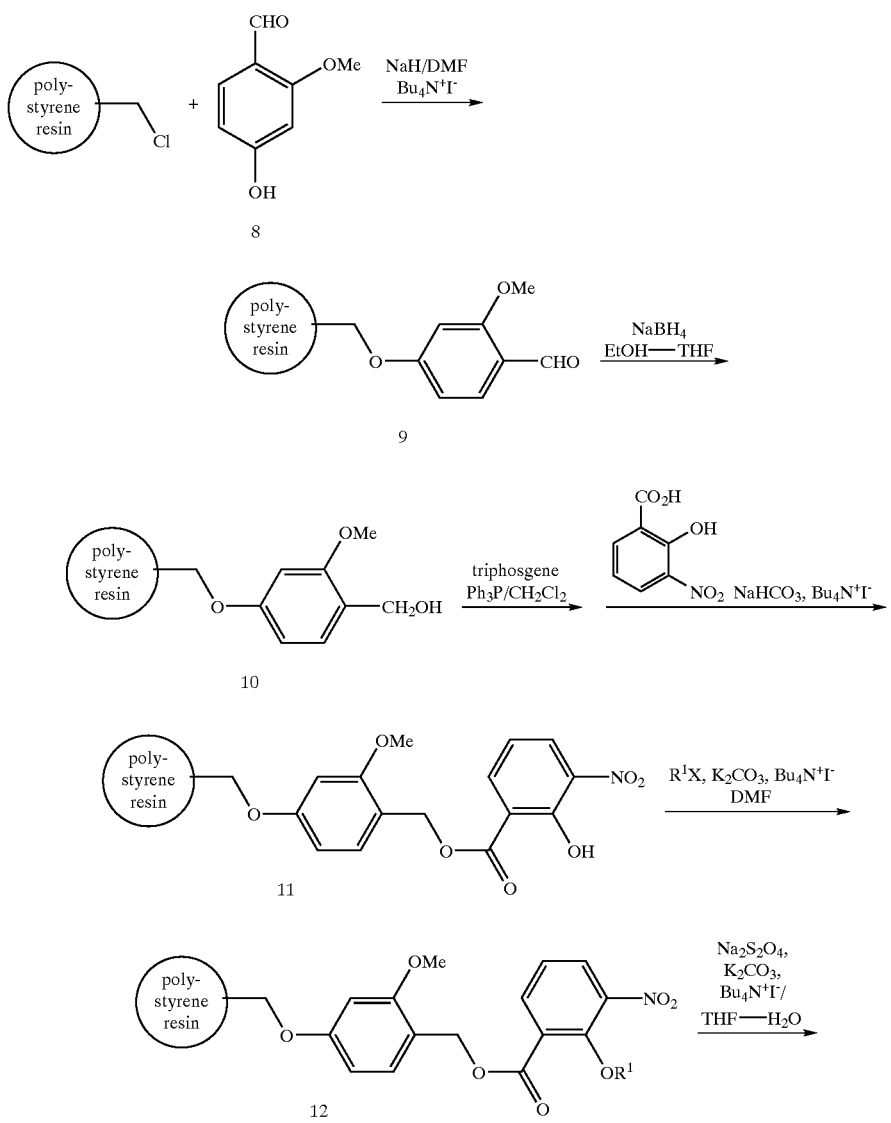

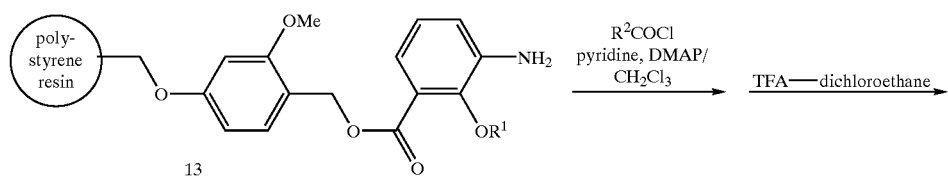

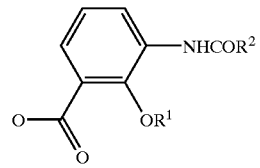

Additional compounds within formula I can be generated via solid phase synthesis. For example, Merrifield resin can be reacted with phenol 8, the resulting aldehyde 9 reduced to alcohol 10 and reacted with 2-hydroxy-3-nitrobenzoic acid to provide phenol 11. Reaction with the appropriate alkyl halide resulted in ether 12. Reduction of the nitro group provided aniline 13. Acylation or sulfonylation (Scheme 4) followed by removal from the resin resulted in amide $I_c$ or sulfonamide $I_d$.

Scheme 4

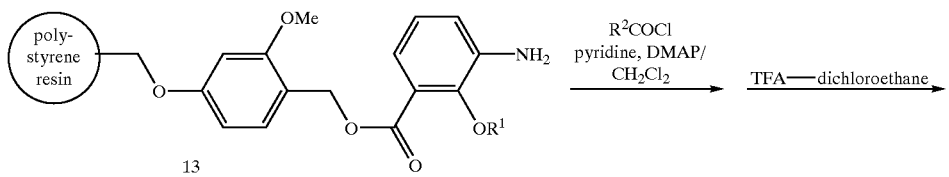

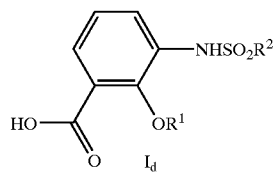

Scheme 5

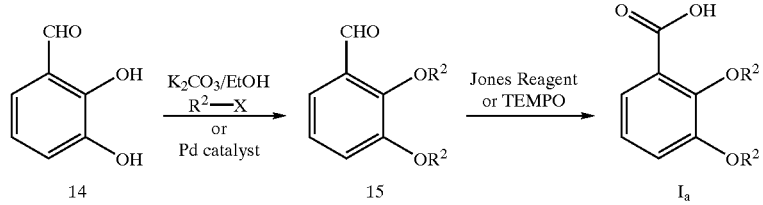

Compound I_a was also obtained by reaction of catechol 14 to give bis ether 15 followed by oxidation.

Scheme 6

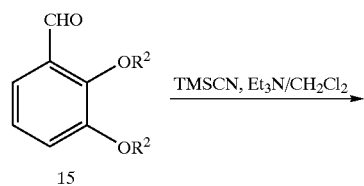

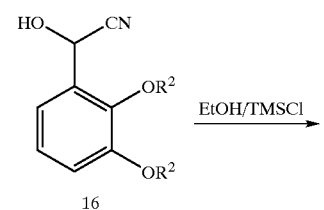

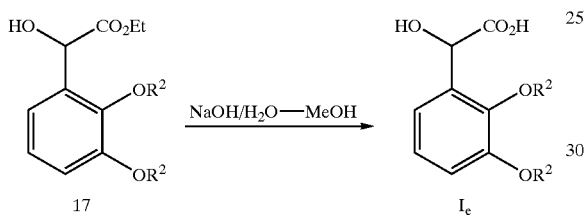

In addition, aldehyde 15 can be converted to cyanohydrin 16 by standard methods and the cyanohydrin converted to ester 17. Saponification resulted in mandelic acid $I_e$.

The enantiomers of compound $I_e$ can be readily separated by the use of a chiral auxillary. Thus, alcohol 17 was esterified with (S)-t-butyloxycarbonyl proline and the resulting diastereomers 18a and 18b were isolated by normal phase chromatography. Subsequent saponification provided (R)-Ie and (S)-$I_e$ in high enantiomeric purity.

Scheme 8

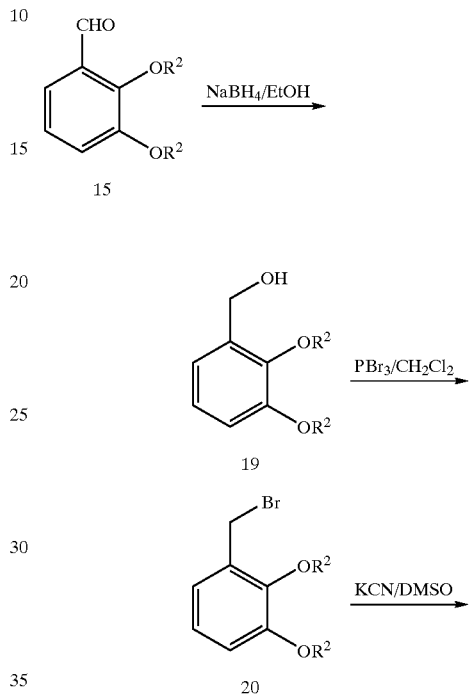

Scheme 7

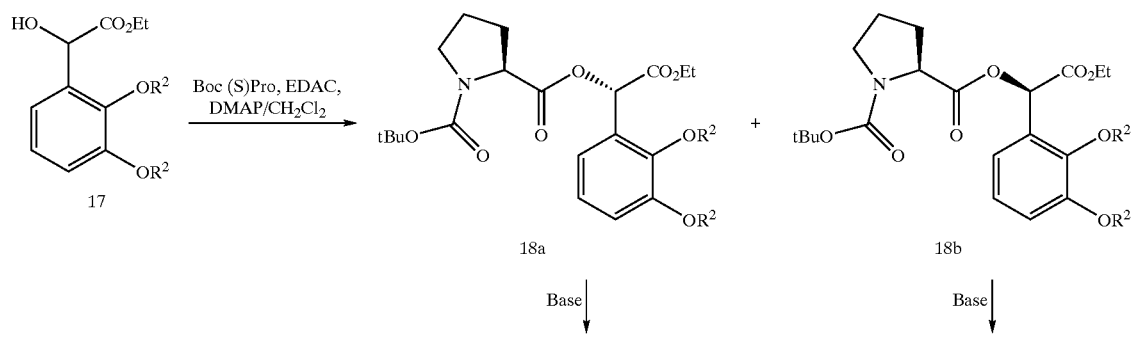

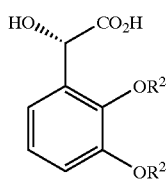

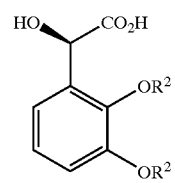

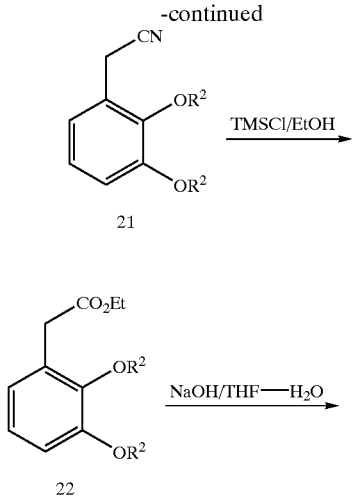

Phenylacetic acids $I_f$ could be prepared from aldehyde 15. By known methods alcohol 19 led to bromide 20 and to nitrile 21. Alcoholic acidolysis provided ester 22 and saponification gave $I_f$.

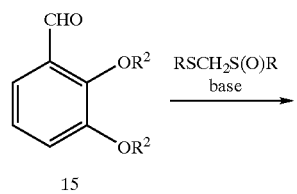

Alternatively, $I_f$ could be prepared from aldehyde 15 by condensation with either methyl sulfinyl methyl sulfoxide or ethyl sulfinyl ethyl sulfide and an appropriate base to give vinyl thioacetal 23. Methanolic acidolysis provided ester 24 and saponification led to $I_f$.

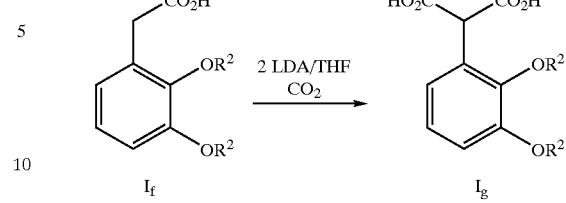

Treatment of $I_f$ with two equivalents of lithium diisopropyl amide followed by carbon dioxide provides malonate $I_g$.

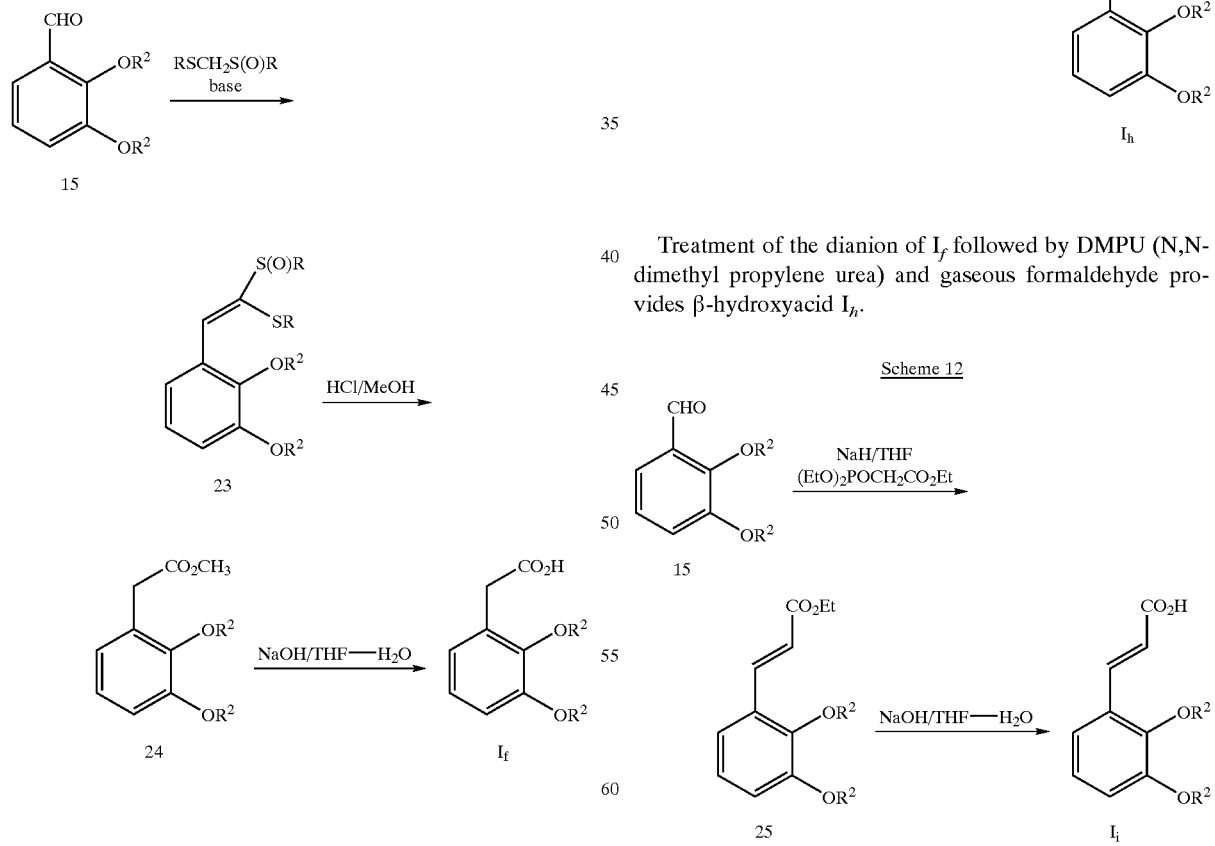

Treatment of the dianion of $I_f$ followed by DMPU (N,N-dimethyl propylene urea) and gaseous formaldehyde provides β-hydroxyacid $I_h$.

Aldehyde 15 could also be used to prepare cinnamate 25, which upon hydrolysis provideds unsaturated acid $I_i$.

Scheme 13

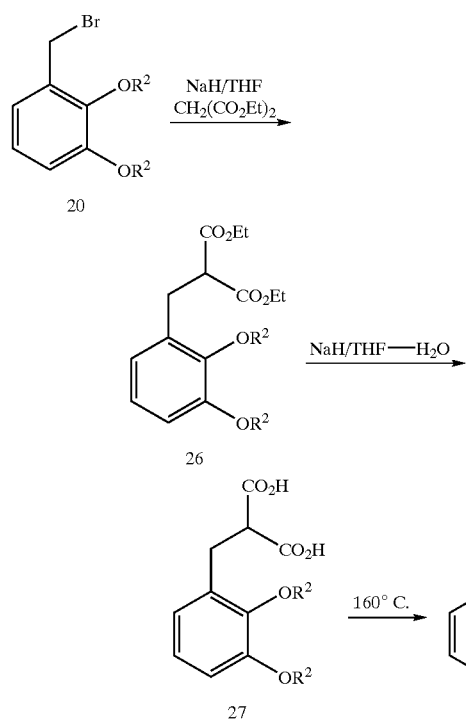

The corresponding saturated acid I$_j$ can be prepared from bromide 20 by alkylation with diethyl malonate, followed by saponification and pyrolysis.

Scheme 14

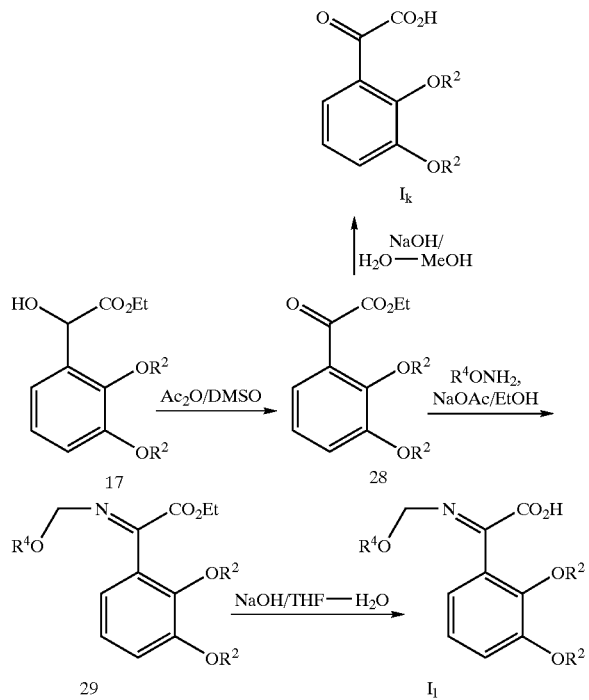

Treatment of the mandelate 17 with oxidizing agents (for example, Jones reagent or AcNHTEMPO) provided ketoester 28; saponification led to ketoacid I$_k$. Reaction of 28 with hydroxylamine or methoxylamine hydrochloride followed by saponification provided oximes I$_l$ as separable geometric isomers.

Scheme 15

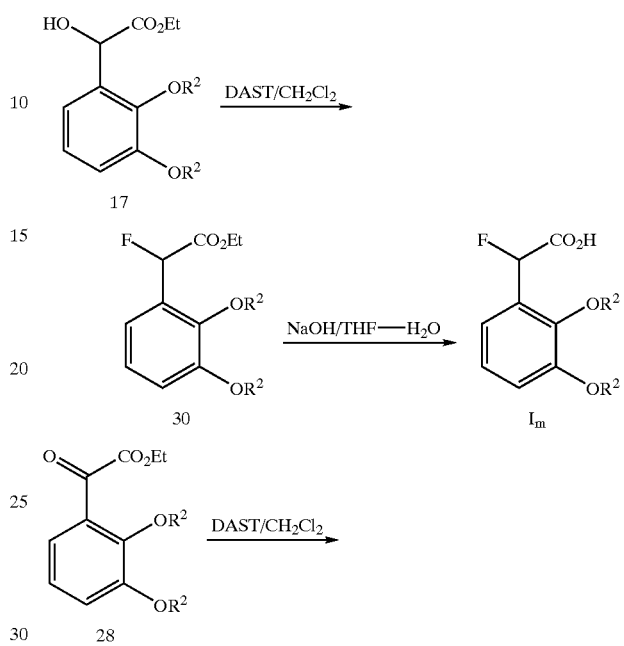

Alcohol 17 on treatment with one equivalent of DAST provides fluoride 30 and saponification yields α-fluorophenylacetic acid I$_m$. Analogously, ketoester 28 on reaction with excess DAST provides difluoride 31 and then I$_n$.

Scheme 16

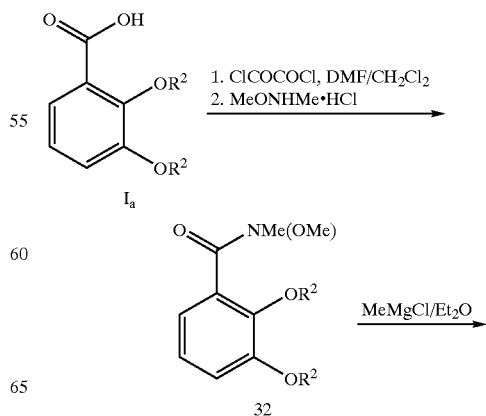

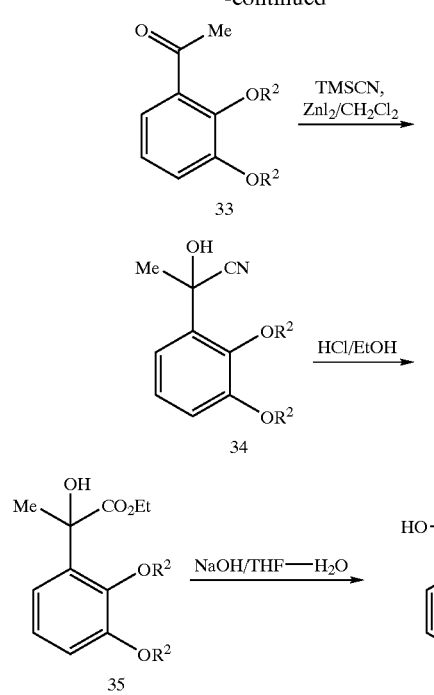

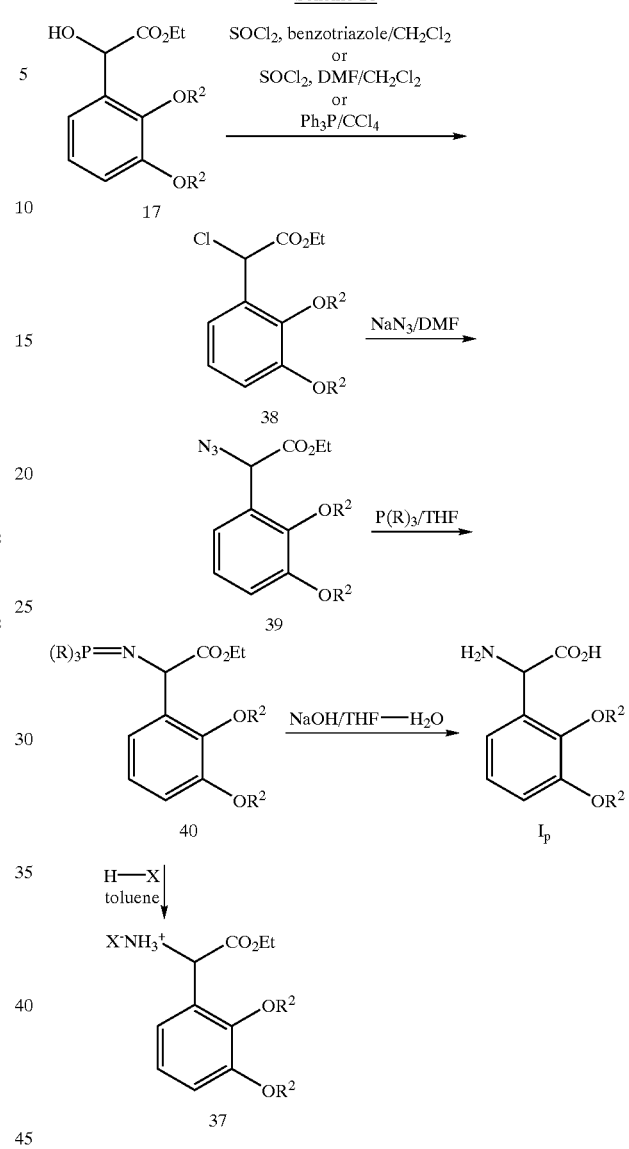

Benzoic acid $I_a$ can be used to prepare α-methyl mandelic acid $I_o$ by preparation of amide 32 and subsequent addition of methyl magnesium chloride to provide acetophenone 33. Cyanohydrin 34 derived from 33 was then hydrolyzed to prepare ester 35 and saponification led to $I_o$.

Amino acid $I_p$ and acylated derivatives $I_q$ can be prepared from aldehyde 15 or hydroxyester 17 as described in Schemes 17, 18 and 19. A modified Strecker procedure provides amino ester 37, hydrolysis of which provides $I_p$. Alternatively, 37 could be prepared from azide 39 and subsequent Staudinger reaction. Acylation of 37 using a variety of methods gave acetomido ester 38, saponification then providing $I_q$.

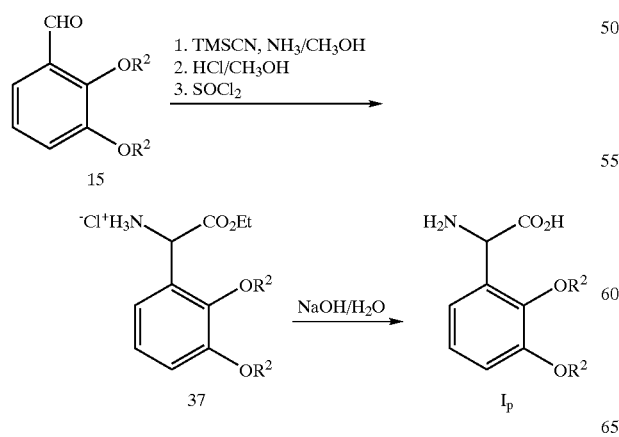

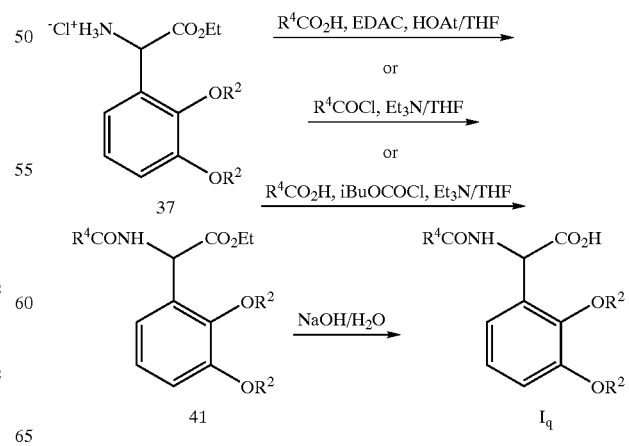

Scheme 20

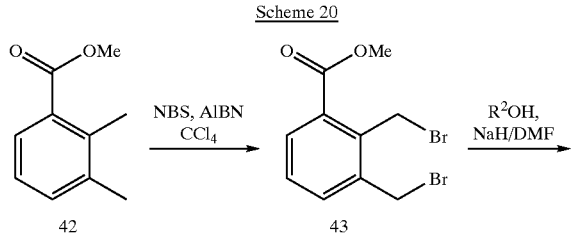

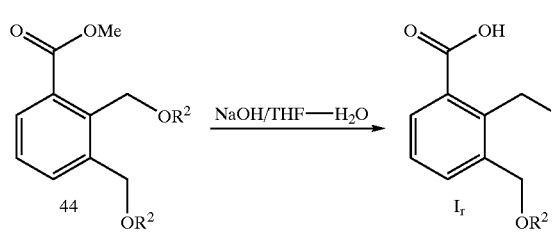

Benzoic acid $I_r$ can be prepared from 2,3-dimethylbenzoate. Double radical bromination of 42 leads predominantly to 43. Displacement of the bromides with an appropriate alcohol anion gives 44 and saponification provides $I_r$.

Scheme 21

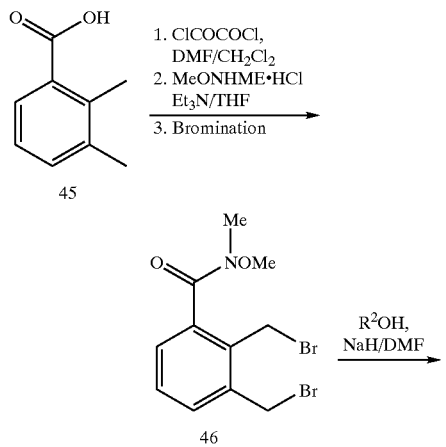

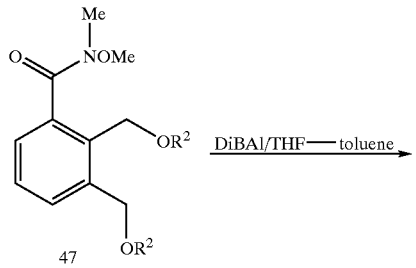

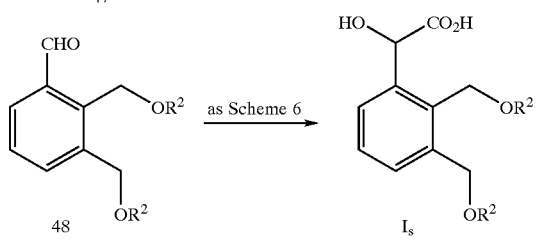

Mandelic acid $I_s$ can be prepared from 2,3-dimethylbenzoic acid 45. The acid is converted into dibromo amide 46. Displacement with an appropriate oxide gives 47, reduction of which provides aldehyde 48. Cyanohydrin formation and hydrolyses, analogous to Scheme 1, provides $I_s$.

Scheme 22

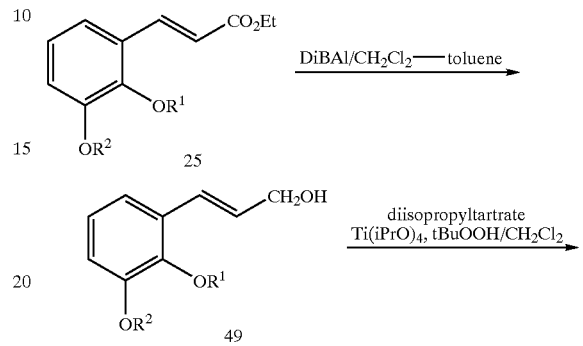

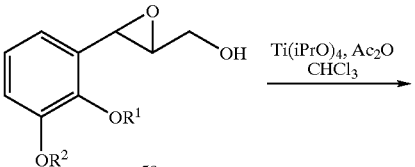

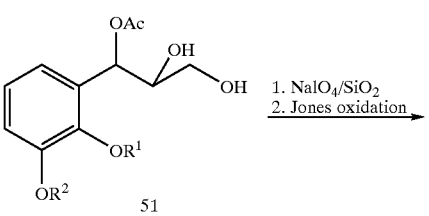

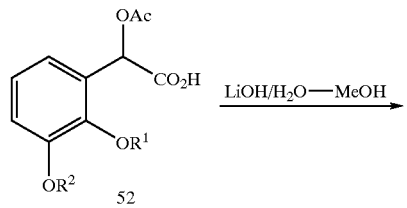

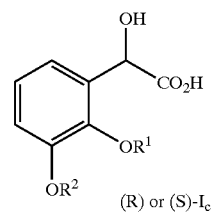

(R) or (S)-$I_e$

An alternative chiral synthesis of (R) or (S)-1e can be shown as follows: cinnamate 25 is reduced to allylic alcohol 49. Sharpless epoxidation with chiral diisopropyltartrate provides epoxide 50 with high enantiomeric excess, which, upon ring-opening with titanium (IV) acetoxytriisopropoxide gives diol 51. Oxidative cleavage of the diol leads to O-(acetyl) mandelate 52 and saponification provides (R) or (S)-1$_e$.

Scheme 23

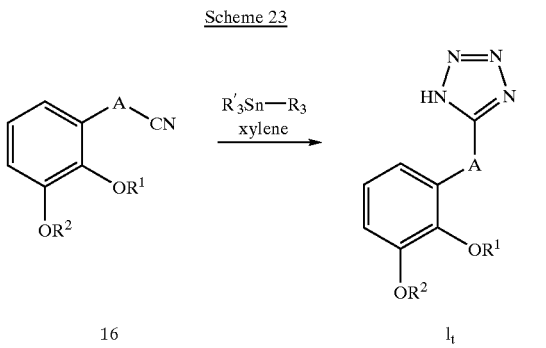

Preparation of tetrazole $1_t$ proceeds from cyanohydrin 16, by treatment with a trialkyltinazide at reflux in xylene.

A dual aP2/k-FABP inhibitor (or dual k-FABP/aP2 inhibitor) is defined herein as any compound which has a $K_i$ value in both an aP2 and K-FABP assay of less than 500 nM (preferably less than 100 nM and more preferably less than 50 nM) and wherein the $K_i$ of the compound in the k-FABP assay differs no more than 100 times the $K_i$ of the compound in the aP2 assay (more preferably the $K_i$ of the compound in the k-FABP assay differs no more than 10 times the $K_i$ of the compound in the aP2 assay). Dual aP2/k-FABP inhibitors will preferably contain less than 60 carbon atoms, more preferably less than 45 carbon atoms, and will contain less than 20 heteroatoms, more preferably less than 12 heteroatoms.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkoxy, haloalkoxy, (alkoxy)alkoxy, alkoxyalkyl, (hydroxy)alkoxyalkyl, (alkoxy)alkoxyalkyl, aryl, aryloxy, (aryl)aryl or diaryl, (aryl)alkoxyaryl, diaryl, arylalkyl, (aryl)alkoxy, (aryl)alkoxyalkyl, (aryloxy)aralkyl, alkenyl, cycloalkyl, cycloalkylalkyl, cycloalkylalkyloxy, amino, substituted amino, alkylamino, hydroxy, hydroxyalkyl, hydroxycarbonyl, alkylcarbonyl, alkoxycarbonyl, arylcarbonyl, acyl, heterocylo, (heterocyclo)alkyl, heteroaryl, heteroaryloxy, heteroarylalkyl, heteroarylalkoxy, aryloxyalkyl, aryloxyaryl, (amino)carbonyl, (substituted amino)carbonyl, alkanoylamino, arylcarbonylamino, nitro, cyano, thiol, haloalkyl, trihaloalkyl and/or alkylthio (where the alkyl radical is optionally substituted), arylthio (where the aryl radical is optionally substituted), sulfonylaryl, arylsulfonylalkyl, alkylsulfonyl, $COOR^4$, $COR^4$ or $SR^4$. Where particular substituted alkyl groups are identified herein they are named by adding the term "alkyl" at the end of the name of the substituent radical (e.g., aralkyl, heteroaralkyl etc.).

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

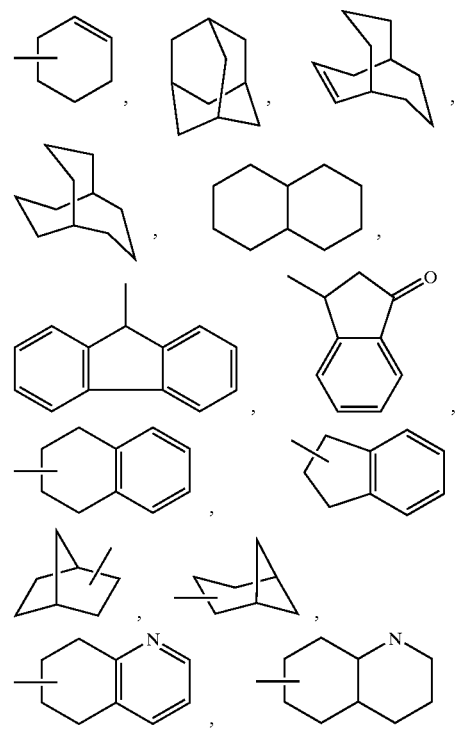

and the like any of which groups may be optionally substituted with 1 to 4 substituents such as halogen, alkyl, haloalkyl, alkoxy, haloalkoxy, hydroxy, aryl, aryloxy, arylalkoxy, arylalkyl, cycloalkyl, alkylamido, alkanoylamino, oxo, acyl, arylcarbonylamino, amino, nitro, cyano, thiol, alkylthio, arylsulfonylalkyl, alkylsulfonyl, $COOR^4$, $COR^4$, and/or $SR^4$.

The term "cycloalkylene" as employed herein refers to a "cycloalkyl" group which includes free bonds and thus is a linking group such as

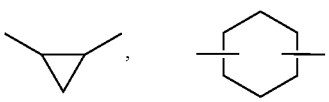

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, heterocyclo, alkanoylamino, alkylamido, arylcarbonyl-amino, nitro, cyano, thiol, alkylthio and/or any of the alkyl substituent groups.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, heterocyclo, hydroxy, alkanoylamino, alkylamido, arylcarbonylamino, nitro, cyano, thiol, and/or alkylthio, and/or any of the alkyl substituents.

The terms "arylalkenyl" and "arylalkynyl" as used alone or as part of another group refer to alkenyl and alkynyl groups as described above having an aryl substituent.

Where alkyl groups as defined above have single bonds for attachment to two other groups from the same or different, they are termed "alkylene" groups and may optionally be substituted as defined above for "alkyl".

Where alkenyl groups as defined above and alkynyl groups as defined above, respectively, have single bonds for attachment to two other groups, they are termed "alkenylene groups" and "alkynylene groups", respectively, and may optionally be substituted as defined above for "alkenyl" and "alkynyl".

Suitable alkylene, alkenylene or alkynylene groups $(CH_2)_x$ or $(CH_2)_y$ (where, y is 1 to 8, preferably 1 to 5, and x is 1 to 5, preferably 1 to 3, which includes alkylene, alkenylene or alkynylene groups) as defined herein, may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy.

Examples of $(CH_2)_x$ or $(CH_2)_y$, alkylene, alkenylene and alkynylene include

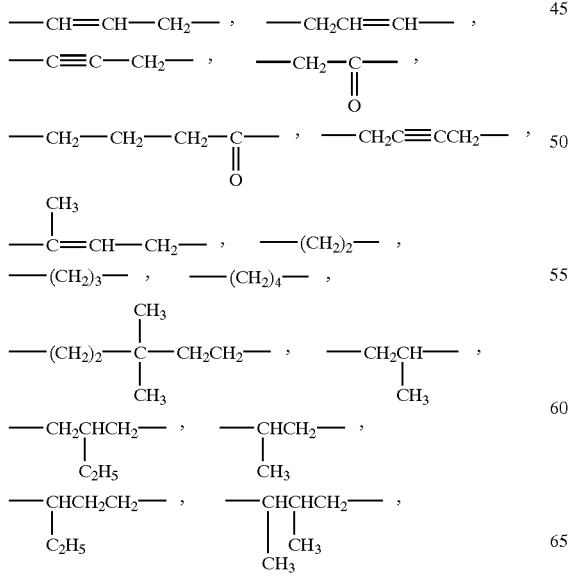

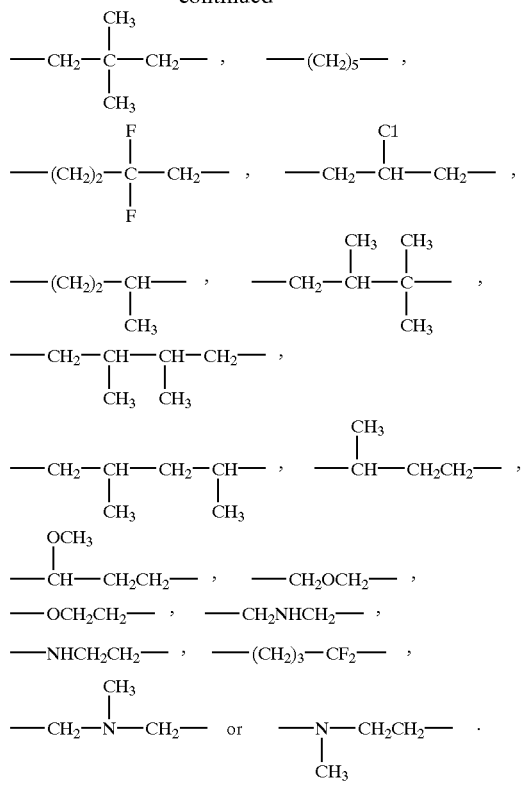

The term "halogen" or "halo" as used herein alone or as part of another group refers to chlorine, bromine, fluorine, and iodine as well as $CF_3$, with chlorine, bromine or fluorine being preferred.

Unless otherwise indicated, the terms "aryl" or "ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or heterocyclo rings for example

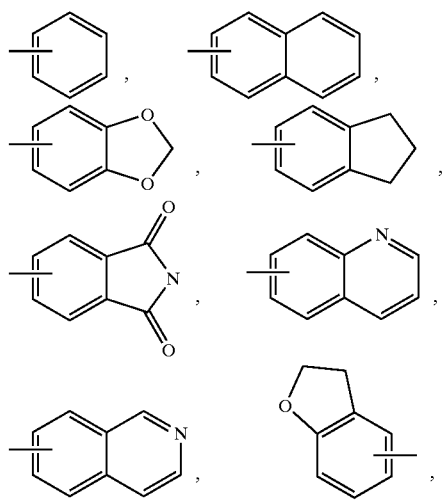

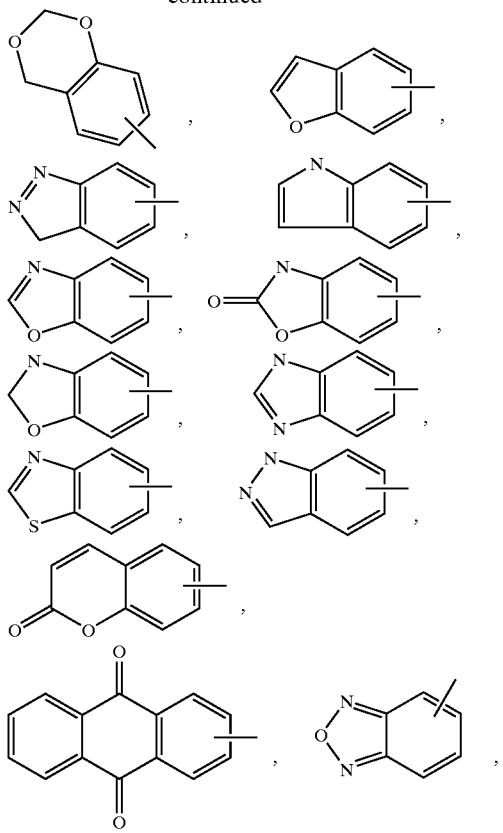

and may be optionally substituted through available carbon atoms with 1, 2, or 3 groups selected from hydrogen, halo, haloalkyl, alkyl, substituted alkyl, alkoxy, haloalkoxy, alkenyl, trifluoromethyl, trifluoromethoxy, alkynyl, cycloalkyl, (cycloalkyl)alkyl, heterocyclo, heterocycloalkyl, aryl, substituted aryl, heteroaryl, substituted heteroaryl, (aryl)alkyl, aryloxy, (aryloxy)alkyl, (aryl)alkoxy, arylthio, arylazo, heteroarylalkyl, heteroarylalkenyl, heteroarylheteroaryl, heteroaryloxy, hydroxy, nitro, cyano, amino, substituted amino, thiol, alkylthio, arylthio, heteroarylthio, arylthioalkyl, alkoxyarylthio, alkylcarbonyl, arylcarbonyl, aminocarbonyl, (substituted amino)carbonyl, (alkyl)aminocarbonyl, (substituted alkyl)aminocarbonyl, (aryl)aminocarbonyl, (substituted aryl)aminocarbonyl, alkoxycarbonyl, (amino)alkoxycarbonyl, (substituted amino)alkoxycarbonyl, alkylcarbonyloxy, arylcarbonyloxy, alkylcarbonylamino, arylcarbonylamino, arylsulfinyl, arylsulfinylalkyl, arylsulfonylamino or arylsulfonylaminocarbonyl, sulfonylaryl, (alkyl)sulfonylaryl, sulfonylarylalkyl, (alkyl)sulfonylaralalkyl, arylsulfonylalkyl, alkylsulfonyl, COOR$^4$, COR$^4$ and/or SR$^4$.

Unless otherwise indicated, the term "lower alkoxyl", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl (optionally substituted), aryl (optionally substituted), arylalkyl (optionally substituted), arylalkyl (optionally substituted), heteroaryl (optionally substituted), heteroarylalkyl (optionally substituted), heterocyclo (optionally substituted), (heterocyclo)alkyl (optionally substituted), cycloalkyl (optionally substituted), cycloalkylalkyl (optionally substituted), haloalkyl (optionally substituted), hydroxyalkyl (optionally substituted), alkoxyalkyl (optionally substituted) or thioalkyl (optionally substituted). In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, substituted alkyl, alkoxy, alkylthio, halo, trifluoromethyl, hydroxy, aryl or substituted aryl.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl group (i.e.,

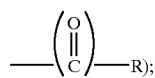

examples of acyl groups include any of the R$^1$ groups attached to a carbonyl, such as alkanoyl, alkenoyl, aroyl, aralkanoyl, heteroaroyl, cycloalkanoyl, heterocycloalkanoyl and the like. Such groups may also be identified by adding the term "carbonyl" at the end of the name of the organic radical R bonded to the acyl group (e.g., alkylaminocarbonyl, alkoxycarbonyl, etc).

Unless otherwise indicated, the term "heterocycle" or "heterocyclo" as used herein alone or as part of another group refers to a 5-, 6- or 7-membered saturated or partially unsaturated ring which includes 1 or more hetero atoms such as nitrogen, oxygen and/or sulfur, linked through a carbon atom or a heteroatom, where possible, optionally via the linker (CH$_2$)$_x$, such as

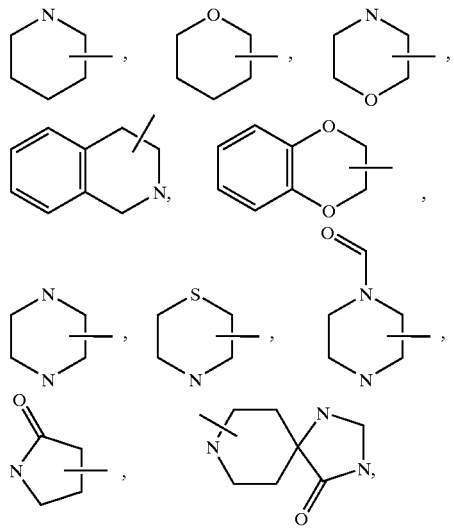

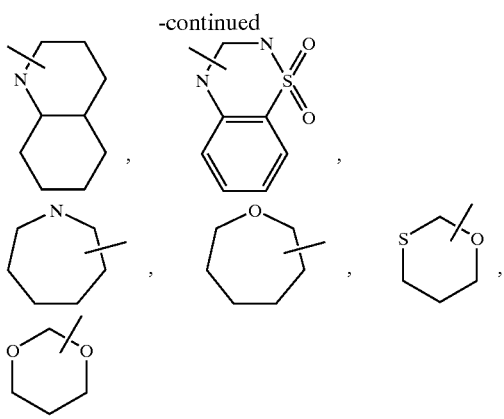

and the like. The above groups may include 1 to 4 substituents such as alkyl, substituted alkyl, halo, alkoxy, haloalkoxy, aryloxy, cyano, nitro, oxo, aryl, substituted aryl, aralkyl, substituted aralkyl, arylsulfonylalkyl, alkylsulfonyl, $COOR^4$, $COR^4$, and/or $SR^4$. In addition, any of the heterocyclo rings can be fused to a cycloalkyl, aryl, heteroaryl or heterocyclo ring. In addition, any of the heterocyclo rings can be joined by spiro union to cycloalkyl rings or other heterocyclo rings.

Unless otherwise indicated, the term "heteroaryl" as used herein alone or as part of another group refers to monocyclic and bicyclic aromatic rings containing from 5 to 10 atoms, which includes 1, 2, 3 or 4 hetero atoms such as nitrogen, oxygen or sulfur, and such rings fused to an aryl, cycloalkyl, heteroaryl or heterocyclo ring (e.g. benzothiophenyl, indolyl), where the nitrogen and sulfur heteroatoms may optionally be oxidized and the nitrogen heteroatoms may optionally be quaternized. The heteroaryl group may optionally include 1 to 4 substituents such as halo, haloalkyl, alkyl, substituted alkyl, alkoxy, haloalkoxy, alkenyl, trifluoromethyl, trifluoromethoxy, alkynyl, cycloalkyl, cycloalkyl-alkyl, heterocyclo, heterocycloalkyl, aryl, substituted aryl, heteroaryl, substituted heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonylaminocarbonyl, sulfonylaryl, sulfonylarylalkyl, arylsulfonylalkyl, alkylsulfonyl, $COOR^4$, $COR^4$ and/or $SR^4$. Examples of heteroaryl groups include the following:

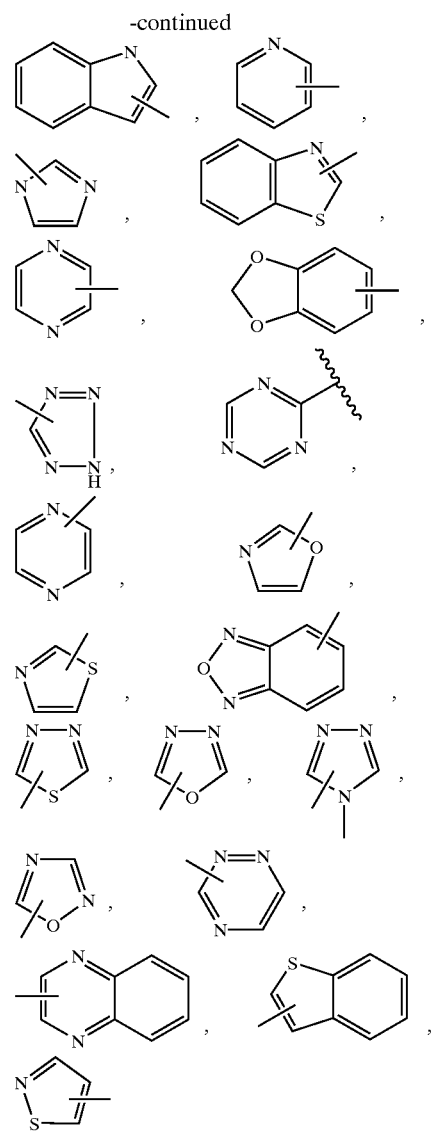

and the like.

The term "heterocycloalkyl" as used herein alone or as part of another group refers to heterocyclo groups as defined above linked to a $(CH_2)_x$ chain.

The term "heteroarylalkyl" or "heteroarylalkenyl" as used herein alone or as part of another group refers to a heteroaryl group as defined above linked to a —$(CH_2)_x$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains a both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. When diastereomeric or enantiomeric products are prepared, they can be separated by conventional methods for example, chromatographic or fractional crystallization.

Thus, where desired, the compounds of the present invention may be used in combination with one or more hypolipidemic agents or lipid-lowering agents, or lipid agents, or lipid modulating agents, and/or one or more other types of therapeutic agents including antidiabetic agents, anti-obesity agents, antihypertensive agents, platelet aggregation inhibitors, anti-Alzheimer's agents, anti-dementia agents, and/or other cardiovascular agents (including anti-anginal agents, anti-arrhythmic agents, anti-atherosclerosis agents, anti-inflammatory agents, anti-platelet agents, anti-heart failure agents), which may be administered orally in the same dosage form or in a separate oral dosage form, or by injection.

The hypolipidemic agent or lipid-lowering agent or other lipid agent or lipid modulating agent which may be optionally employed in combination with the compounds of the present invention may include 1,2,3 or more MTP inhibitors, HMG CoA reductase inhibitors, squalene synthetase inhibitors, PPAR α agonists, PPAR dual α/γ agonists, PPAR δ agonists, fibric acid derivatives, ACAT inhibitors, lipoxygenase inhibitors, cholesterol absorption inhibitors, ileal Na$^+$/bile acid cotransporter inhibitors, upregulators of LDL receptor activity, cholesteryl ester transfer protein inhibitors, bile acid sequestrants, and/or nicotinic acid and derivatives thereof.

MTP inhibitors employed herein include MTP inhibitors disclosed in U.S. Pat. No. 5,595,872, 5,739,135, 5,712,279, 5,760,246, 5,827,875, 5,885,983 and 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

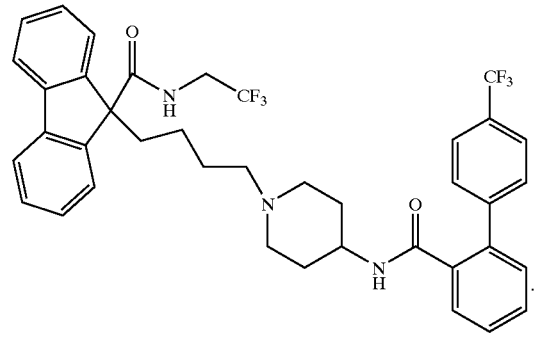

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. No. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphonosulfonates disclosed in U.S. Pat. No. 5,712,396, those disclosed by Biller et al, J. Med. Chem., 1988, Vol. 31, No. 10, pp 1869–1871, including isoprenoid (phosphinylmethyl)phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137 (1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd), as well as F-1394, CS-505, F-12511, HL-004, K-10085 and YIC-C8–434.

The hypolipidemic agent may be an upregulator of LDL receptor activity such as MD-700 (Taisho Pharmaceutical Co. Ltd) and LY295427 (Eli Lilly).

The hypolipidemic agent may be a cholesterol absorption inhibitor preferably Schering-Plough's $SCH_{48461}$ (ezetimibe) as well as those disclosed in Atherosclerosis 115, 45–63 (1995) and J. Med. Chem. 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425–430 (1999).

The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201;

a beta-lactam cholesterol absorption inhibitor such as disclosed in EP 675714;

an HDL upregulator such as an LXR agonist, a PPAR α-agonist and/or an FXR agonist;

an LDL catabolism promoter such as disclosed in EP 1022272;

a sodium-proton exchange inhibitor such as disclosed in DE 19622222;

an LDL-receptor inducer or a steroidal glycoside such as disclosed in U.S. Pat. No. 5,698,527 and GB 2304106;

an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E;

isoniazid as disclosed in WO 97/35576;

a cholesterol absorption inhibitor, an HMG-CoA synthase inhibitor, or a lanosterol demethylase inhibitor as disclosed in WO 97/48701;

a PPAR δ agonist for treating dyslipidemia;

or a sterol regulating element binding protein-I (SREBP-1) as disclosed in WO 2000/050574, for example, a sphingolipid, such as ceramide, or neutral sphingomyelenase (N-SMase) or fragment thereof.

Preferred hypolipidemic agents are pravastatin, lovastatin, simvastatin, atorvastatin, fluvastatin, pitavastatin and rosuvastatin, as well as niacin and/or cholestagel.

The above-mentioned U.S. patents are incorporated herein by reference. The amounts and dosages employed will be as indicated in the Physician's Desk Reference and/or in the patents set out above or as otherwise known in the art.

The compounds of the present invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent or other lipid agent or lipid modulating agent will be as disclosed in the various patents and applications discussed above.

The dosages and formulations for the other hypolipidemic agent or other lipid agent or lipid modulating agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, or fluvastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The anti-atherosclerotic agent includes a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties," Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of the present invention and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The antidiabetic agent which may be optionally employed in combination with the compounds of the present invention may be 1,2,3 or more antidiabetic agents or antihyperglycemic agents including insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl.

Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms.

The compounds of the present invention will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention will be employed in a weight ratio to the glucosidase inhibitor within the range from about 0.01:1 to about 100:1, preferably from about 0.05:1 to about 10:1.

The compounds of the present invention may be employed in combination with a PPAR γ agonist such as a thiazolidinedione oral anti-diabetic agent or other insulin sensitizers (which has an insulin sensitivity effect in NIDDM patients) such as troglitazone (disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention will be employed in a weight ratio to the thiazolidinedione in an amount within the range from about 0.01:1 to about 100:1, preferably from about 0.05:1 to about 10:1.

The sulfonyl urea and PPAR γ agonists in amounts of less than about 150 mg oral antidiabetic agent may be incorporated in a single tablet with the compounds of the present invention.

The compounds of the present invention may also be employed in combination with a antihyperglycemic agent such as insulin or with glucagon-like peptide-1 (GLP-1) or mimetic such as GLP-1 (1–36) amide, GLP-1(7–36) amide, GLP-1 (7–37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the PPAR anti-diabetic agent may be employed in amounts within the range from about 0.01 to about 2000 mg/day which may be administered in single or divided doses one to four times per day.

Where present insulin and other anti-diabetic agents as set out above may be employed in formulations, amounts and dosing as indicated by the Physician's Desk Reference.

Where present GLP-1 peptides or mimetics may be administered in oral buccal formulations, by nasal administration or parenterally as described in U.S. Pat. Nos. 5,346,701 (TheraTech), 5,614,492 and 5,631,224 which are incorporated herein by reference.

The antidiabetic agent or other lipid agent may also be a PPAR modulator such as a PPAR alpha/gamma dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. Pat. No. 6,414,002, the disclosure of which is incorporated herein by reference, employing dosages as set out therein, which compounds designated as preferred are preferred for use herein.

The antidiabetic agent may be an SGLT2 inhibitor such as disclosed in U.S. Pat. No. 6,414,126, employing dosages as set out therein. Preferred are the compounds designated as preferred in the above application.

The antidiabetic agent may be a DP4 inhibitor such as disclosed in U.S. Pat. No. 6,395,767, WO99/38501, WO99/46272, WO99/67279, WO99/67278, WO99/61431, NVP-DPP728A (1-[[[2-[(5-cyanopyridin-2-yl)amino]ethyl] amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compounds of the present invention may be repaglinide, nateglinide (Novartis) or KAD1229 (PF/Kissei), with repaglinide being preferred.

The antidiabetic compound may be a melanocortin receptor agonist such as a spiropiperidine as disclosed in WO 99/64002.

The compounds of the present invention will be employed in a weight ratio to the meglitinide, PPAR modulator such as a PPAR gamma agonist, PPAR α agonist, PPAR δ agonits or antagonist, PPAR alpha/gamma dual agonist, DP4 inhibitor or SGLT2 inhibitor or other antidiabetic agent within the range from about 0.01:1 to about 100:1, preferably from about 0.05:1 to about 10:1.

The other type of therapeutic agent which may be optionally employed with the compounds of the present invention may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor beta drug, a PTP-1B inhibitor, an anorectic agent, a PPAR modulator including PPAR γ antagonists, PPAR α agonists, PPAR δ antagonists, a CCKA agonist, a leptin inhibitor such as a leptin receptor activator, a neuropeptide Y antagonist, a melanocortin-4-receptor (MC4R) agonist, or a fatty acid oxidation upregulator or inducer such as Famoxin (Genset).

The beta 3 adrenergic agonist which may be optionally employed in combination with the compounds of the present invention may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750, 355 and CP331648 being preferred.

The neuropeptide Y antagonists which may be optionally employed in combination with the compounds of the present invention include those described in WO 01/13917, in U.S. Pat. No. 6,218,408 and in WO 01/14376.

The lipase inhibitor which may be optionally employed in combination with compounds of the present invention may be orlistat or ATL-962 (Alizyme), with orlistat being preferred.

The serotonin (and dopoamine) reuptake inhibitor which may be optionally employed in combination with compounds of the present invention may be sibutramine, topiramate (Johnson & Johnson) or axokine (Regeneron), with sibutramine and topiramate being preferred.

The thyroid receptor beta compound which may be optionally employed in combination with compounds of the present invention may be a thyroid receptor ligand as disclosed in WO97/21993, WO99/00353, GB98/284425, and WO 01/60784.

The anorectic agent which may be optionally employed in combination with compounds of the present invention may be dexamphetamine, phentermine, phenylpropanolamine or mazindol, with dexamphetamine being preferred.

The CCKA agonists which may be employed herein include Glaxo-SmithKline's GI-181,771 and Sanofi's SR146,131.

The PTP-LB inhibitor which may be an anti-oesity and/or an antidiabetic agent include those disclosed in WO 99/585, 521, WO 99/58518, WO 99/58522 and WO 99/61435.

The anti-obesity agent employed may also be Pfizer's P57 or CP-644,673.

The various anti-obesity agents described above may be employed in the same dosage form with the compounds of the present invention or in different dosage forms, in dosages and regimens as generally known in the art or in the PDR.

The antihypertensive agents which may be employed in combination with the compounds of the invention include ACE inhibitors, angiotensin II receptor antagonists, NEP inhibitors such as candoxatril, NEP/ACE inhibitors, as well as calcium channel blockers (such as verapamil and amlodipine besylate), T-channel calcium antagonists (such as mibefradil), β-adrenergic blockers, diuretics, α-adrenergic blockers (such as doxazosin mesylate and terazosin HCl), dual ET/AT receptor antagonists, heart failure drugs such as digoxin, and other types of antihypertensive agents.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Curr. Ther. Res. 39:671 (1986); 40:543 (1986); ramipril (Hoechst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31–2201 (Hoffman-LaRoche) disclosed in FEBS Lett. 165:201(1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and C1925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4tetrahydro-6,7-dimethoxy-3-isoquinolinecarboxyhic acid HCl) disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, gemopatrilat ([S[(R*,R*)]-hexahydro-6-[(2-mercapto-1-oxo-3-phenylpropyl)amino]-2,2-dimethyl-7-oxo-1H-azepine-1-acetic acid) and CGS 30440.

The angiotensin II receptor antagonist (also referred to herein as angiotensin II antagonist or AII antagonist) suitable for use herein includes, but is not limited to, irbesartan, losartan, valsartan, candesartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist will be as set out in the latest edition of the Physician's Desk Reference (PDR).

Dual ET/AT receptor antagonists suitable for use herein include those disclosed in WO 01/44239.

Other examples of preferred antihypertensive agents suitable for use herein include omapatrilat, gemopatrilat, amlodipine besylate, prazosin HCl, verapamil, nifedipine, diltiazem, felodipine, nisoldipine, isradipine, nicardipine, beta blockers such as nadolol, atenolol, sotalol, terazosin, doxazosin, carvedilol, and propranolol, and clonidine HCl.

Diuretics which may be employed in combination with compounds of the present invention include hydrochlorothiazide, torasemide, furosemide, spironolactone, and indapamide.

Antiplatelet agents which may be employed in combination with compounds of the present invention include aspirin, clopidogrel, ticlopidine, dipyridamole, abciximab, tirofiban, eptifibatide, anagrelide, and ifetroban, with clopidogrel and aspirin being preferred.

The antihypertensive agents, diuretics and antiplatelet drugs may be employed in amounts as indicated in the PDR. Ifetroban may be employed in amounts as set out in U.S. Pat. No. 5,100,889.

Anti-Alzheimer's agents or anti-dementia agents suitable for use herein include tacrine HCl and donepezil, as well as γ-secretase inhibitors, β-secretase inhibitors and/or antihypertensive agents. Dosages employed will be as set out in the PDR.

a cyclooxygenase (COX)-2 inhibitor, such as celecoxib, rofecoxib or paracoxib or a glycoprotein IIa/IIIb receptor antagonist such as disclosed in WO 99/45913 and tirofiban or abciximab;

a 5-HT reuptake inhibitor such as disclosed in WO 99/44609;

anti-anginal agents such as vasodilators, for example, isosorbide dinitrate, or nitroglycerin;

anti-atherosclerosis agents such as ACAT inhibitors and lipoxygenase inhibitors as described herein and phospholipase A-2 inhibitors such as S-3013 and SB-435,495 (which are also anti-inflammatory agents); or an immunosuppressant (for use in transplantations) such as cyclosporine, mycophenolate mofetil, azathioprine and the like.

It will be appreciated that unless otherwise specified the dosage regiment for therapeutic agents used in combination with the compounds of the invention will be as specified in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 20 and 2,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The aP2/mal-1 inhibitor activity of the compounds of the invention may be determined using methods well known to those of skill in the art.

The following Examples illustrate embodiments of the present invention, and are not intended to limit the scope of the claims. Abbreviations employed herein are defined below. Compounds of the Examples are identified by the example and step in which they are prepared (for example, "1A" denotes the title compounds of step A of Example 1), or by the example only where the compound is the title compound of the example (for example "4" denotes the title compound of Example 4).

9-BBN=9-borabicyclo[3.3.1]nonane
Calc=calculated
DiBAl=diisobutylaluminum hydride
DMAP=Dimethylaminopyridine
DMF=dimethylformamide
DMSO=dimethylsulfoxide
Et=ethyl
Fnd=found
h=hours
LC/MS=liquid chromatography/mass spectrometry
LDA=lithium diisopropylamide
Me=methyl
Ms=mesyl=methanesulfonyl
OAc=acetate
Ph=phenyl
TFA=trifluoroacetic acid
THF=tetrahydrofuran
TMS=trimethylsilyl

EXAMPLE 1

2,3-Bis[(2-chlorophenyl)methoxy]-α-hydroxybenzeneacetic acid

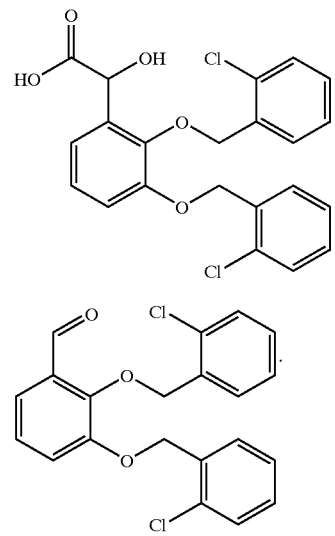

To a stirred slurry of 2,3-dihydroxybenzaldehyde (6.91 g, 50.0 mmol) and potassium carbonate (17.2 g, 125 mmol) in EtOH (60 mL) at room temperature under argon was added 2-chlorobenzyl chloride (15 mL, 120 mmol). The reaction mixture was heated to reflux for 16 h, then cooled and poured into water (150 mL). The resulting solids were collected, washed with water, air-dried and recrystallized from methanol to give the title compound as white needles (16.28 g, 71% yield), mp 98–100° C. LC/MS gave the correct molecular ion [(M+H)⁺=387] for the desired compound.

B

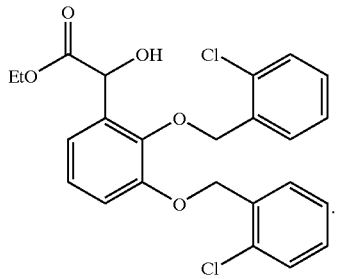

To a stirred solution of part A compound (5.01 g, 12.9 mmol) in CH$_2$Cl$_2$ (50 mL) at room temperature under argon was added trimethylsilylcyanide (1.725 mL, 12.9 mmol) and triethylamine (200 µL, 1.4 mmol). The resulting yellow solution was stirred for 3 h and then evaporated. The residuum was then dissolved in EtOH (25 mL) and trimethylsilyl chloride (25 mL) was added. The colorless solution was heated to 50° C. for 48 h. The solution was cooled, evaporated and the residuum was stirred rapidly for 1 h with CH$_2$Cl$_2$ (50 mL), EtOH (25 mL) and saturated sodium bicarbonate solution (50 mL). The mixture was partially evaporated to remove the ethanol and the remainder partitioned with CH$_2$Cl$_2$. The organic extract was dried (MgSO$_4$) and evaporated. Purification by flash chromatography (5×25 cm column, 1:49 Et$_2$O/CH$_2$Cl$_2$) provided the title compound as a colorless oil which slowly solidified (4.97 g, 84% yield), mp 47–49° C. LC/MS gave the correct molecular ion [(M+H)⁺=461] for the desired compound.

C

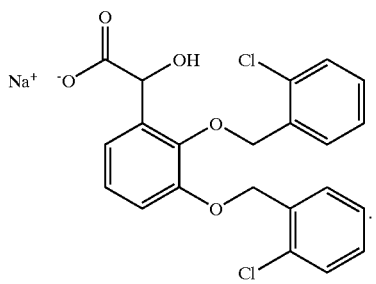

A solution of part B compound (1.40 g, 3.03 mmol) in THF (10 mL) was stirred at room temperature under argon, as 1 M NaOH solution (5 mL, 5.0 mmol) was added. After 24 h, the reaction mixture was diluted with water (20 mL) and extracted twice with Et$_2$O. The aqueous phase was acidified with 1 M hydrochloric acid (5.5 mL, 5.5 mmol), extracted twice with CH$_2$Cl$_2$, the extracts dried (MgSO$_4$) and evaporated. A portion of the resulting gummy solid (1.10 g) was dissolved in Et$_2$O (20 mL) and extracted once with 0.1 M sodium hydroxide solution (23 mL, 2.3 mmol). The aqueous layer was purged with nitrogen gas for 15 min and then lyophilized to give the title compound as a white powder, 988 mg, 87% yield. LC/MS gave the correct molecular ion [(M+H)⁺=433] for the desired compound as its free acid.

EXAMPLE 2

α(R)-2,3-Bis[(2-chlorophenyl)methoxy]-α-hydroxybenzeneacetic acid

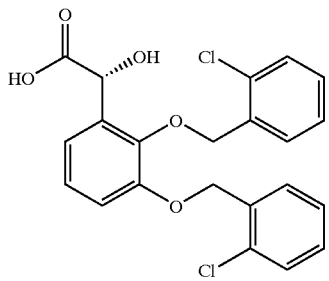

A

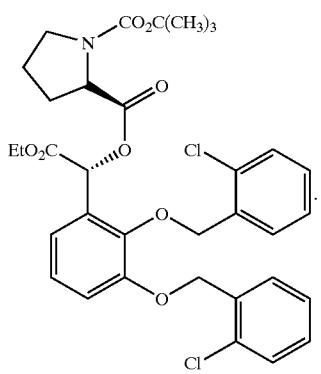

To a stirred slurry of Example 1, Part B compound (1.334 g, 2.89 mmol), N-t-butyloxycarbonyl-(S)-proline (646 mg, 3.00 mmol), triethylamine (210 µL, 1.5 mmol) and DMAP (122 mg, 1.0 mmol) in CH$_2$Cl$_2$ (10 mL) at room temperature under argon was added N-Ethyl N',N'-diisoproylaminoethyl carbodiimide (573 mg, 3.0 mmol). After 16 h, the reaction mixture was diluted with CH$_2$Cl$_2$ and washed once with 5% potassium hydrogren sulfate solution. The organic phase was dried (Na$_2$SO$_4$) and evaporated. Purification by flash chromatography (5×25 cm column, 1.5 L 1:24 Et$_2$O/CH$_2$Cl$_2$, then 1:16 Et$_2$O/CH$_2$Cl$_2$) gave two fractions. The first product to elute was the title compound as a colorless oil. LC/MS gave the correct molecular ion [(M+H)⁺=659] for the desired compound.

B

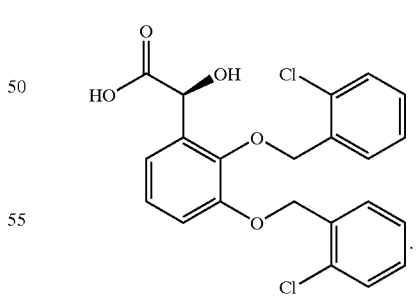

To a stirred solution of part A compound (2.18 g, 3.30 mmol) in dioxane (10 mL) at room temperature under argon was added KOH solution (10.0 mL, 1 M, 10.0 mmol). The resulting solution was heated to 70° C. for 4 h and then cooled to room temperature. After acidifying with 5% potassium hydrogen sulfate solution, the reaction mixture was extracted twice with CH$_2$Cl$_2$. The extracts were combined, washed once with brine, dried (MgSO$_4$) and evaporated. The oily residue was dissolved in 4 N HCl/dioxane (10 mL), stirred under argon for 2 h and then evaporated and re-evaporated twice from hexanes. The residual oil was dissolved in ether (10 mL) and washed twice with water (10 mL) and then extracted with 0.1 M NaOH (30.0 mL, 3.00 mmol). The aqueous layer was frozen and lyophilized to provide the title compound as a white powder, 1.30 g (100% yield). LC/MS gave the correct molecular ion [(M+H)$^+$= 433] for the desired compound. Chiral purity was determined by chromatography of the methyl ester (prepared from a 3 mg sample of the title compound using trimethylsilyl-diazomethane in Et$_2$O/CH$_3$OH) on a normal-phase OD column (hexane/isopropanol as the elutent). Optical purity was determined to be 96.7%.

EXAMPLE 3

α(S) -2,3-Bis[(2-chlorophenyl)methoxy]-α-hydroxybenzeneacetic acid

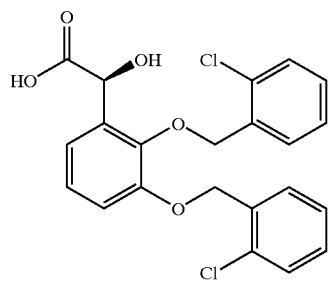

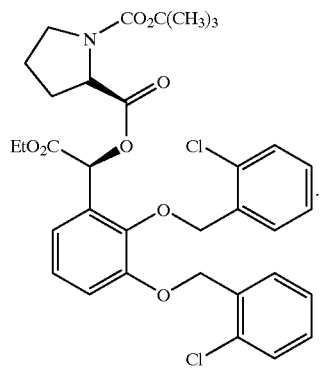

To a stirred slurry of Example 1, Part B compound (1.334 g, 2.89 mmol), N-t-butyloxycarbonyl-(S)-proline (646 mg, 3.00 mmol), triethylamine (210 μL, 1.5 mmol) and DMAP (122 mg, 1.0 mmol) in CH$_2$Cl$_2$ (10 mL) at room temperature under argon was added N-Ethyl N',N'-diisoproylaminoethyl carbodiimide (573 mg, 3.0 mmol). After 16 h, the reaction mixture was diluted with CH$_2$Cl$_2$ and washed once with 5% potassium hydrogren sulfate solution. The organic phase was dried (Na$_2$SO$_4$) and evaporated. Purification by flash chromatography (5×25 cm column, 1.5 L 1:24 Et$_2$O/CH$_2$Cl$_2$, then 1:16 Et$_2$O/CH$_2$Cl$_2$) gave two fractions. The first product to elute was Example 2 Part C compound. The second was the title compound as a colorless oil. LC/MS gave the correct molecular ion [(M+H)$^+$=659] for the desired compound.

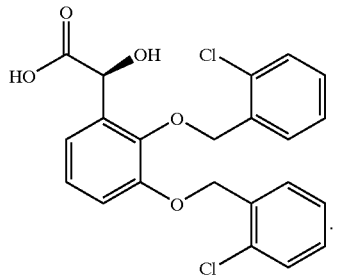

To a stirred solution of part A compound (2.56 g, 3.90 mmol) in dioxane (10 mL) at room temperature under argon was added KOH solution (10.0 mL, 1 M, 10.0 mmol). The resulting solution was heated to 70° C. for 4 h and then cooled to room temperature. After acidifying with 5% potassium hydrogen sulfate solution, the reaction mixture was extracted twice with CH$_2$Cl$_2$. The extracts were combined, washed once with brine, dried (MgSO$_4$) and evaporated. The oily residue was dissolved in 4 N HCl/dioxane (10 mL), stirred under argon for 2 h and then evaporated and re-evaporated twice from hexanes. The residual oil was dissolved in ether (10 mL) and washed twice with water (10 mL) and then extracted with 0.1 M NaOH (33.0 mL, 3.30 mmol). The aqueous layer was frozen and lyophilized to provide the title compound as a white powder, 1.50 g (100% yield). LC/MS gave the correct molecular ion [(M+H)$^+$= 433] for the desired compound. Chiral purity was determined by chromatography of the methyl ester (prepared from a 3 mg sample of the title compound using trimethylsilyl-diazomethane in Et$_2$O/CH$_3$OH) on a normal-phase OD column (hexane/isopropanol as the elutent). Optical purity was determined to be 96.5%.

EXAMPLE 4

2-(E)-3-[2,3-Bis[(2-chlorophenyl)methoxy]phenyl]-2-propenoic acid

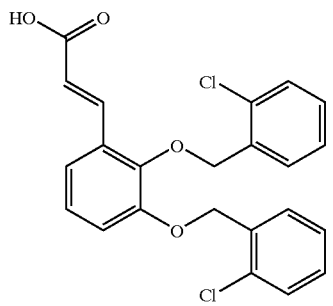

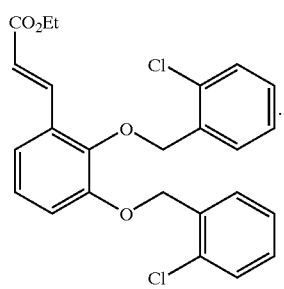

To a stirred solution of triethyl phosphonoacetate (561 mg, 2.50 mmol) in THF (5.0 mL) at room temperature under argon was added sodium hydride (60% mineral-oil dispersion, 96 mg, 2.4 mmol). The reaction mixture was warmed to 50° C. for 1 h and then cooled to room temperature. Example 1 Part A compound (775 mg, 2.00 mmol) was added in one portion. The resulting mixture was stirred for 30 min, quenched with saturated sodium bicarbonate solution and extracted with CH$_2$Cl$_2$. The organic extract was dried (MgSO$_4$) and evaporated. Recrystallization from CH$_2$Cl$_2$/hexanes gave title compound as a white solid (715 mg, 78% yield), mp 95–97° C. LC/MS gave the correct molecular ion [(M+H)$^+$=457] for the desired compound.

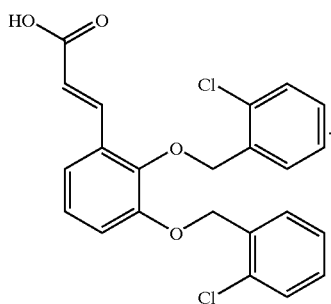

B

To a stirred solution of part A compound (700 mg, 1.53 mmol) in THF (3 mL) at room temperature under argon was added NaOH solution (3.0 mL, 1 M, 3.0 mmol). The resulting solution was heated to 50° C. for 14 h and then cooled to room temperature. After acidifying with 1 M HCl, the resulting solids were collected, washed with water and air-dried to provide the title compound as a white solid, 648 mg (99% yield), mp 187–189° C. LC/MS gave the correct molecular ion [(M+H)$^+$=430] for the desired compound.

EXAMPLE 5

2,3-Bis[(2-chlorophenyl)methoxy]benzeneacetic acid

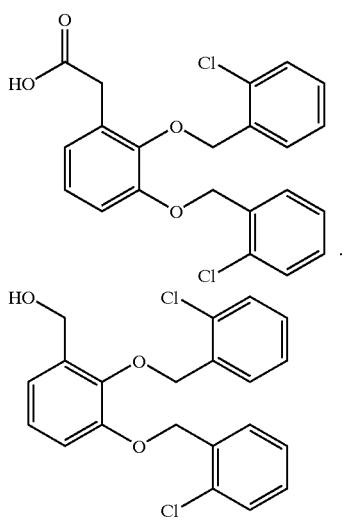

A

To a stirring slurry Example 1 Part A compound (1.00 g, 2.58 mmol) in EtOH (10 mL) at room temperature was added powdered sodium borohydride (100 mg, 2.6 mmol) over 1 min. The resulting mixture was stirred for 16 h, quenched with saturated sodium bicarbonate solution (20 mL) and stirred 20 min. The resulting solids were collected, washed with water and air-dried to give the title compound as a white solid (930 mg, 93% yield), mp 102–104° C. LC/MS gave the correct molecular ion [(M+H)$^+$=389] for the desired compound.

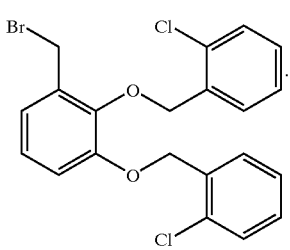

B

To a stirred solution of part A compound (930 mg, 2.4 mmol) in CH$_2$Cl$_2$ (10 mL) at 0° C. under argon was added phosphorous tribromide solution (5.0 mL, 1 M in CH$_2$Cl$_2$, 5.0 mmol) over 1 min. The resulting solution was warmed to room temperature. After 3 h, the reaction was quenched with saturated sodium bicarbonate solution (20 mL) and then treated with solid sodium bicarbonate to bring to pH 7. The mixture was extracted twice with EtOAc, dried (MgSO$_4$) and evaporated to provide the title compound as a white amorphous solid, 1.05 g (97% yield). LC/MS gave the correct molecular ion [(M+H)$^+$=451] for the desired compound.

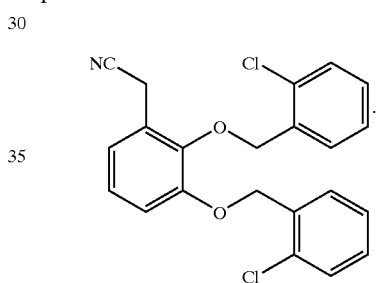

C

To a stirred solution of part B compound (875 mg, 1.94 mmol) in DMSO (8 mL) at room temperature under argon was added potassium cyanide (1.30 g, 20 mmol). The resulting solution was warmed to 65° C. After 3 h, the reaction was quenched with water and the resulting gummy solid was collected, washing with water. The solid was dissolved in CH$_2$Cl$_2$, washed with water, dried (MgSO$_4$) and evaporated. Purification by flash chromatography provided the title compound as a light yellow amorphous solid, 343 mg (44% yield). LC/MS gave the correct molecular ion [(M+H)$^+$=398] for the desired compound.

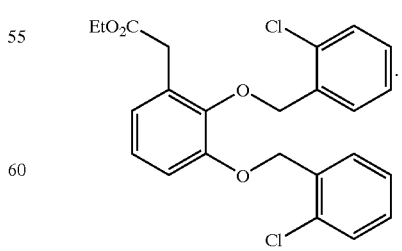

D

To a stirred solution of part C compound (340 mg, 0.85 mmol) in EtOH (4 mL) at room temperature under argon was added chlorotrimethylsilane (4 mL). The resulting solution was warmed to 50° C. After 34 h, the reaction was cooled to room temperature and evaporated. The residue was stirred vigorously with saturated sodium bicarbonate solution (10 mL) for 30 min and then extracted three times with CH$_2$Cl$_2$. The extracts were combined, dried (MgSO$_4$) and evaporated. Purification by flash chromatography provided the title compound as a colorless oil, 223 mg (59% yield). LC/MS gave the correct molecular ion [(M+H)$^+$=445] for the desired compound.

E

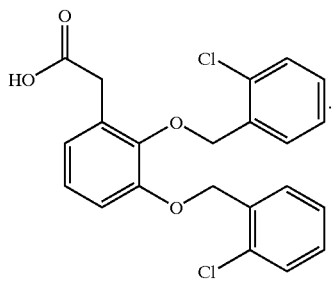

To a stirred solution of part D compound (220 mg, 0.49 mmol) in THF (1 mL) at room temperature under argon was added sodium hydroxide solution (1.5 mL, 1.0 M, 1.5 mmol). The resulting solution was heated to 50° C. for 15 h. The reaction mixture was cooled, diluted with water (3 mL) and extracted once with Et$_2$O. The aqueous phase was acidified with 1 N HCl to pH 2 and extracted twice with CH$_2$Cl$_2$. The CH$_2$Cl$_2$ extracts were combined, dried (MgSO$_4$) and concentrated to ~2 mL. Hexanes were added, the flask scratched and the resulting white solid was collected and air-dried to give the title compound as a white solid, 198 mg, 94% yield, mp 105–107° C. LC/MS gave the correct molecular ion [(M+H)$^+$=417] for the desired compound.

EXAMPLE 6

2,3-Bis[(2-chlorophenyl)methoxy]benzeneacetic acid Alternative Synthesis

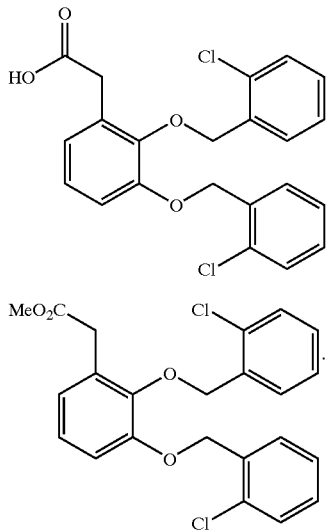

To a stirred solution of Example 1 Part A compound (1.94 g, 5.00 mmol) and methylthiomethyl methylsulfoxide (0.58 mL, 5.6 mmol) in THF (5 mL) at room temperature under argon was added Triton-B (0.5 mL, 40% in MeOH). The resulting solution was heated to gentle reflux for 16 h and then evaporated and re-evaporated twice from hexanes. The residue was purified by flash chromatography to give the thioketene S-oxide as a colorless oil, 2.06 g (83% yield).

This oil was dissolved in MeOH (100 mL) and HCl gas was bubbled into the solution as the temperature rose to 66° C. before subsiding to room temperature. After 30 min more, the reaction was evaporated and re-evaporated from CH$_2$Cl$_2$. Purification by flash chromatography gave the title compound as a white solid, 1.66 g, 93% yield. LC/MS gave the correct molecular ion [(M+H)$^+$=431] for the desired compound.

B

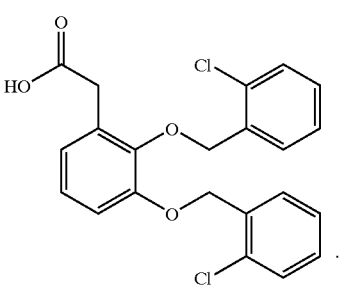

By the method of Example 5 Part E, Part A compound (1.00 g, 2.32 mmol) was hydrolyzed to give the title compound as a white solid, 964 mg, 100% yield, mp 105–107° C.

EXAMPLE 7

[[2,3-Bis[(2-chlorophenyl)methoxy]phenyl]methyl] propanedioic acid

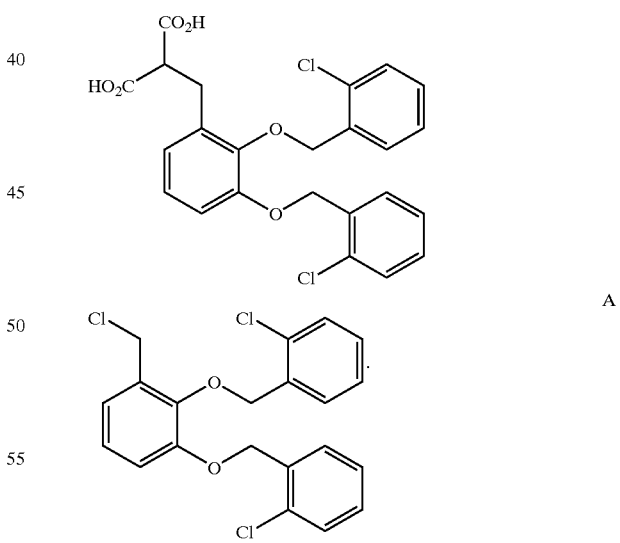

To a stirred solution of Example 5 Part A compound (1.00 g, 2.57 mmol) and triphenylphosphine (674 mg, 2.57 mmol) in THF (2.5 mL) at room temperature under argon was added carbon tetrachloride (15 mL) and the reaction heated to 50° C. After 24 h, the reaction evaporated and purified by flash chromatography to provide the title compound as a white solid, 517 mg (49% yield), mp 96–98° C. LC/MS gave the correct molecular ion [(M+H)⁺=407] for the desired compound.

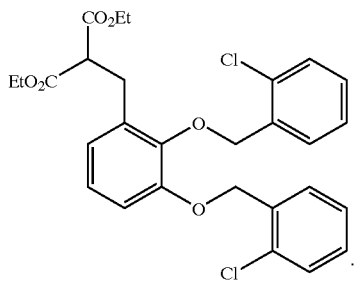

B

To a stirred slurry of sodium hydride (60% mineral oil dispersion, 75 mg, 1.88 mmol) in THF (5 mL) at room temperature under argon was added a solution of diethyl malonate (300 µL, 2.0 mmol) in THF (5 mL). After 30 min, a solution of Part A compound (500 mg, 1.23 mmol) in THF (2 mL) was added in one portion. After 14 h, the reaction mixture was quenched with 5% potassium hydrogen sulfate solution and extracted twice with EtOAc. The organic extracts were combined, dried (MgSO₄) and evaporated. Purification by flash chromatography on silica gel provided the title compound as a colorless oil, 524 mg (80% yield). LC/MS gave the correct molecular ion [(M+H)⁺=531] for the desired compound.

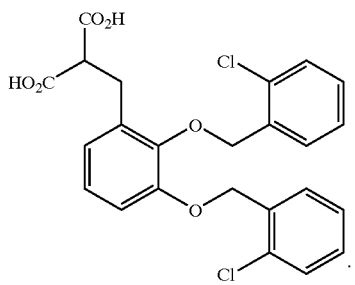

C

A stirred mixture of part B compound (520 mg, 0.99 mmol) in potassium hydroxide solution (246 mg, 4.4 mmol in 4 mL of water) was heated to reflux under argon for 24 h. The reaction mixture was cooled, diluted with water (3 mL) and extracted once with Et₂O. The aqueous phase was brought to pH 2 with 3 N HCl and the resulting solids filtered, washed with water and air-dried to give the title compound as a white solid, 365 mg (77% yield), mp 148–150° C. (dec). LC/MS gave the correct molecular ion [(M+H)⁺=475] for the desired compound.

EXAMPLE 8

2,3-Bis[(2-chlorophenyl)methoxy]benzenepropanoic acid

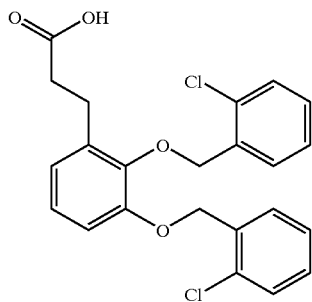

Example 7 Part C compound (256 mg, 0.54 mmol) was heated to 155° C. at a pressure of 1 Torr for 3 h. The reaction mixture was cooled and recrystallized directly from hexanes/toluene to provide the title compound as a white solid (225 mg, 97% yield), mp 131–132° C. LC/MS gave the correct molecular ion [(M+H)⁺=431] for the desired compound.

EXAMPLE 9

2,3-Bis[(2-chlorophenoxy)methyl]benzoic acid

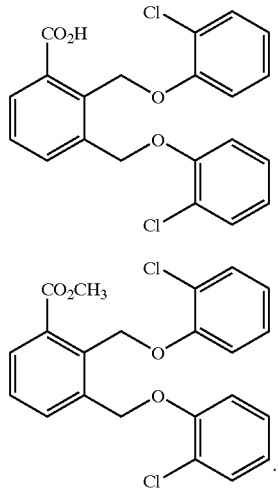

A

To a stirred solution of methyl 2,3-dimethylbenzoate (1.75 g, 10.7 mmol) in carbon tetrachloride (35 mL) under argon was added freshly recrystallized N-bromosuccinimide (3.90 g, 21.9 mmol) and AIBN (50 mg). The reaction mixture was heated to reflux under argon for 4 h and then cooled and filtered. Evaporation gave a yellow oil, 3.53 g, predominantly methyl 2,3-bis(bromomethyl)benzoate.

To a stirred solution of 2-chlorophenol (2.83 g, 22.0 mmol) in DMF (20 mL) at room temperature under argon was added sodium hydride (60% mineral oil dispersion, 880 mg, 22 mmol) over 5 min. The resulting clear solution was stirred 30 min and a solution in DMF (5 mL) of the dibromide prepared above was added. After 14 h, the reaction mixture was quenched with water and extracted three times with Et₂O. The extracts were combined and washed twice with water, once with brine, dried (MgSO₄) and evaporated. Purification by flash chromatography on silica gel provided the title compound as a white solid, 2.03 g (46% yield), mp 107–109° C. LC/MS gave the correct molecular ion [(M+H)⁺=417] for the desired compound.

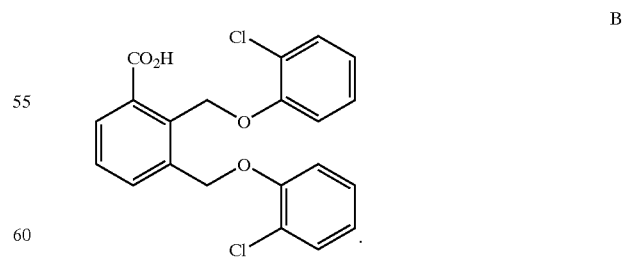

B

To a solution of Part A compound (270 mg, 0.647 mmol) in EtOH (2 mL) at room temperature under argon was added sodium hydroxide solution (2.0 mL, 1 M, 2.0 mmol). The mixture was heated to 50° C. for 1 h. The reaction mixture was cooled, diluted with water (3 mL) and extracted once with Et$_2$O. The aqueous phase was brought to pH 2 with 1 N HCl and the resulting solids filtered, washed with water and air-dried to give the title compound as a white solid, 238 mg (91% yield), mp 172–174° C. LC/MS gave the correct molecular ion [(M+H)$^+$=403] for the desired compound.

EXAMPLE 10

3-[(2-Chlorophenoxy)methyl]-2-[(2-chlorophenyl)methoxy]benzoic acid

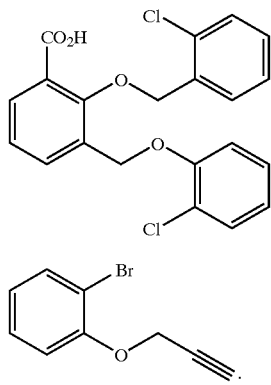

To a stirred solution of 2-bromophenol (3.42 g, 19.8 mmol) in DMF (10 mL) under argon was added propargyl bromide (80% in toluene, 4.12 g, 27.7 mmol) and potassium carbonate (3.80 g, 27.5 mmol). The reaction mixture was stirred for 90 min, then diluted with water and extracted twice with Et$_2$O. The extracts were combined, washed once with water, three times with 1 M NaOH (25 mL portions) and once with brine, dried (MgSO$_4$) and evaporated. Purification by flash chromatography on silica gel provided the title compound as a colorless oil, 3.93 g (94% yield). LC/MS gave the correct molecular ion [(M+H)$^+$=211] for the desired compound.

B

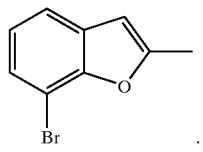

A stirred slurry of Part A compound (3.00 g, 14.2 mmol) and cesium fluoride (3.02 g, 20 mmol) in N,N-diethylaniline (24 mL) under argon was heated to 210° C. for 4 h. The reaction mixture was then cooled, diluted with hexanes and washed three times with 1 M HCl (100 mL portions). The organic phase was dried (MgSO$_4$) and evaporated. Purification by flash chromatography (hexanes as the elutant) provided the title compound as a colorless oil, 1.94 g (67% yield). LC/MS gave the correct molecular ion [(M+H)$^+$=211] for the desired compound.

C

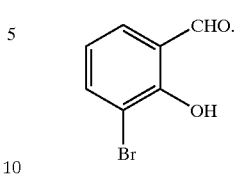

A stirred solution of Part B compound (1.94 g, 9.19 mmol) in CH$_2$Cl$_2$ (100 mL) protected from atmospheric moisture by a calcium chloride drying tube was cooled to −78° C. and a 3% O$_3$/O$_2$ gas mixture is bubbled through the solution until a blue color persists (~35 min). The solution was purged with nitrogen gas and then dimethylsulfide (5 mL) was added and the reaction allowed to warm to room temperature. After 4 h, the solution was evaporated and the residue redissolved in MeOH (8 mL) to which was added water (8 mL) and potassium carbonate (1.1 g, 80 mmol). The mixture was heated to 55° C. under argon for 1 h and then cooled, neutralized with 1 M potassium hydrogen sulfate to pH 7 and extracted twice with CH$_2$Cl$_2$. The organic extracts were combined, dried (MgSO$_4$) and evaporated. Purification by flash chromatography provided the title compound as a light yellow crystalline solid, 1.47 g (80% yield). LC/MS gave the correct molecular ion [(M+H)$^+$=201] for the desired compound.

D

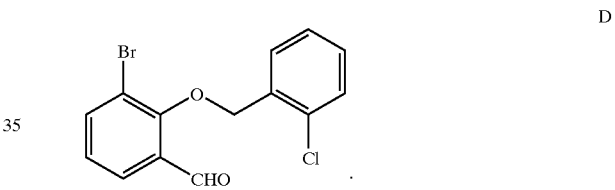

To a solution of Part C compound (638 mg, 3.17 mmol) in DMF (10 mL) at room temperature under argon was added sodium hydride (60% mineral oil dispersion, 140 mg, 3.5 mmol). After 20 min, 2-chloro-benzyl chloride (0.50 mL, 4.0 mmol) and tetrabutylammonium iodide (200 mg, 0.5 mmol) was added and the reaction was heated to 60° C. After 14 h the reaction mixture was cooled, diluted with Et$_2$O and washed once with 5% potassium hydrogen sulfate solution, twice with water, once with brine, dried (MgSO$_4$) and evaporated. Purification by flash chromatography provided the title compound as a white solid, 734 mg (71% yield), mp 96–98° C. LC/MS gave the correct molecular ion [(M+H)$^+$=325] for the desired compound.

E

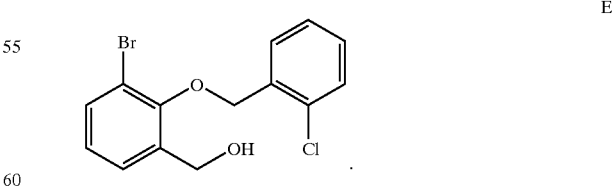

To a solution of Part D compound (672 mg, 2.06 mmol) in CH$_2$Cl$_2$ (10 mL) at room temperature under argon was added diisobutylaluminum hydride solution (1 M in toluene, 2.3 mL, 2.3 mmol). After 1 h, the reaction mixture was quenched with 1 M potassium sodium tartrate solution (4 mL) and stirred for 1 h. The reaction mixture was extracted twice with EtOAc. The organic extracts were combined, dried (MgSO$_4$) and evaporated to provide the title compound as a white solid, 675 mg (100% yield). LC/MS gave the correct molecular ion [(M+H)$^+$=327] for the desired compound.

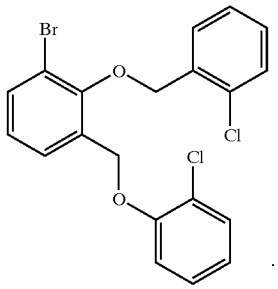

F

To a solution of Part E compound (407 mg, 1.24 mmol) in CH$_2$Cl$_2$ (5 mL) at 0° C. under argon was added phosphorous tribromide solution (1 M in CH$_2$Cl$_2$, 2.5 mL, 2.5 mmol). After 15 min, the reaction mixture was warmed to room temperature for 1 h and then diluted with CH$_2$Cl$_2$, washed once with water, once with saturated sodium bicarbonate solution and once with brine. The organic extract was dried (MgSO$_4$) and evaporated. The product was unstable and therefore used immediately by dissolving in DMF (1 mL) and adding to a solution prepared from 2-chlorophenol (0.2 mL, 1.3 mmol) and sodium hydride (60% mineral oil dispersion, 50 mg, 1.25 mmol) in DMF (3 mL) at room temperature under argon. The reaction mixture was stirred for 16 h. The reaction was quenched with water and extracted three times with hexanes. The hexanes extracts were combined, washed once with water, dried (MgSO$_4$) and evaporated. Purification by flash chromatrography on silica gel provided the title compound as a colorless oil, 115 mg (21% yield). LC/MS gave the correct molecular ion [(M+H)$^+$=437] for the desired compound.

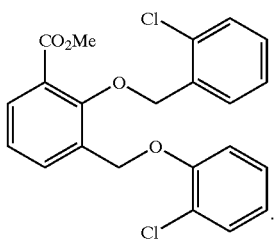

G

To a solution of Part F compound (110 mg, 0.25 mmol) in methanol (1.5 mL) and DMF (2 mL) was added Pd(OAc)$_2$ (12 mg, 0.05 mmol), dppf (21 mg, 0.05 mmol) and triethylamine (70 μL, 0.5 mmol). The stirred solution was purged twice with carbon monoxide gas and then heated under a CO-filled balloon at 80° C. After 18 h, the reaction mixture was cooled, diluted with water and brought to pH$_3$ with 10% aqueous potassium hydgrogen sulfate. The mixture was extracted twice with ether and the organic extract dried (MgSO$_4$). Flash chromatography on silica gel gave the title compound as a colorless oil, 51 mg (49% yield). LC/MS gave the correct molecular ion [(M+H)$^+$=417] for the desired compound.

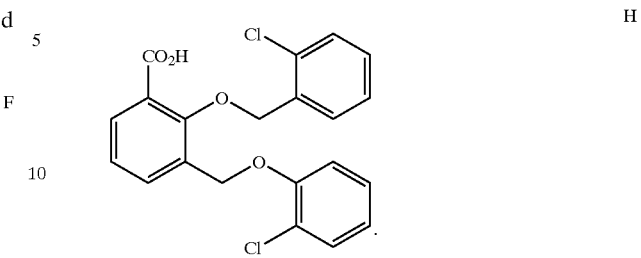

H

To a solution of Part G compound (50 mg, 0.12 mmol) in THF (1 mL) at room temperature under argon was added sodium hyroxide solution (1 mL, 1 M, 1 mmol). After 14 h, the solution was acidified (1 M HCl) and partially evaporated. The resulting solids were filtered, washed with water and air-dried to give the title compound as a white solid, 45 mg, 93% yield, mp 172–174° C. LC/MS gave the correct molecular ion [(M+H)$^+$=403] for the desired compound.

EXAMPLE 11

Alternate Synthesis of Example 10

3-[(2-Chlorophenoxy)methyl]-2-[(2-chlorophenyl)methoxy]benzoic acid

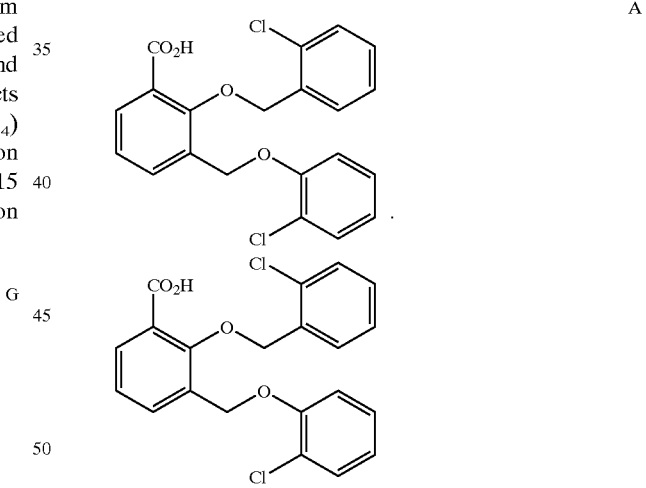

To a solution of Example 10 Part F compound (208 mg, 0.474 mmol) in THF (4 mL) at −78° C. under argon was added n-butyllithium solution (200 μL, 2.5 M in hexane, 0.5 mmol) over 10 min. After 3 h, dry carbon dioxide gas was bubbled into the reaction mixture as the reaction was allowed to warm to room temperature. After 1 h at room temperature, the reaction mixture was quenched with 1 M NaOH (1 mL, 1 mmol) and extracted twice with hexanes. The aqueous phase was brought to pH 2 with 1 N HCl and the resulting solids filtered, washed with water and air-dried to give the title compound as a white solid, 16.5 mg (9% yield), mp 172–174° C. LC/MS gave the correct molecular ion [(M+H)$^+$=403] for the desired compound.

EXAMPLE 12

α-Amino-2,3-bis[(2-chlorophenyl)methoxy]benzeneacetic acid

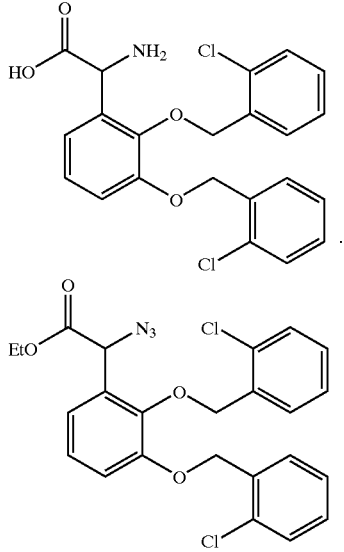

A

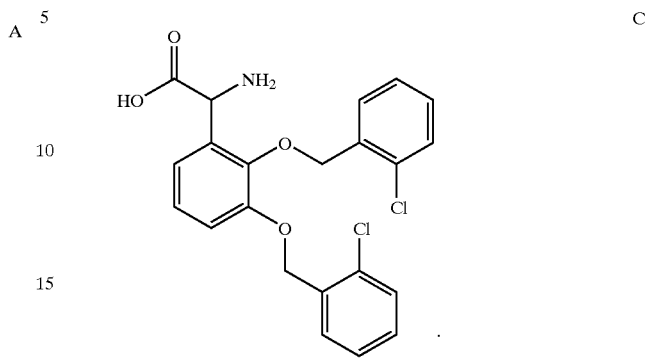

To a stirred solution of Example 1 Part B compound (1.009 g, 2.19 mmol) in CH$_2$Cl$_2$ (20 mL) under argon at room temperature was added a solution prepared from benzotriazole (570 mg, 4.8 mmol) and thionyl chloride (570 mg, 4.8 mmol) in CH$_2$Cl$_2$ (5 mL) over 2 min. The reaction mixture was stirred for 90 min, then diluted with water and extracted twice with CH$_2$Cl$_2$. The extracts were combined, washed once with water, once with 0.5 M NaOH (25 mL) and once with brine, dried (MgSO$_4$) and evaporated. The residuum was immediately dissolved in DMF (8 mL), treated with sodium azide (570 mg, 8.8 mmol) and stirred at room temperature under argon for 1 h. The reaction mixture was quenched with water and extracted twice with Et$_2$O. The extracts were combined, washed twice with water, once with brine dried (MgSO$_4$) and evaporated. Purification by flash chromatography on silica gel provided the title compound as a colorless oil, 657 mg (62% yield). LC/MS gave the correct molecular ion [(M+H)$^+$=486] for the desired compound.

B

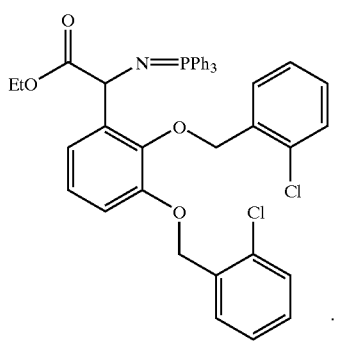

A stirred solution of Part A compound (652 mg, 1.34 mmol) under argon at room temperature in THF (4 mL) was treated with triphenylphosphine (352 mg, 1.34 mmol). After 15 h, the reaction mixture was evaporated and re-evaporated twice from hexanes to give the title compound as a colorless oil, 965 mg (100% yield). LC/MS gave the correct molecular ion [(M+H)$^+$=720] for the desired compound.

C

To a stirred solution of Part B compound (880 mg, 1.22 mmol) in THF (8 mL) at room temperature under argon was added sodium hydroxide solution (2.5 mL, 1 M, 2.5 mmol). After 14 h, the solution was diluted with water and extracted once with CH$_2$Cl$_2$. The aqueous phase was cooled and the resulting precipitate was filtered. The filtrate was lyophilized and the residue was purified by reverse phase preparative HPLC (YMC S5 ODS 20×250 mm column, MeOH/water-TFA elutant) to give the title compound as its trifluoroacetic acid salt, 450 mg (82% yield). LC/MS gave the correct molecular ion [(M+H)$^+$=432] for the desired compound as its free base.

EXAMPLE 13

α-(Acetylamino)-2,3-bis[(2-chlorophenyl)methoxy]benzeneacetic acid

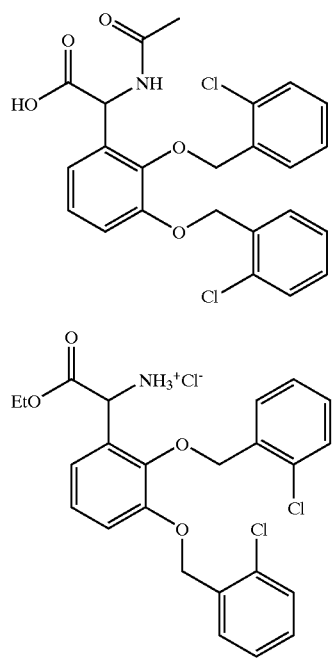

A

A stirred slurry of Example 1 Part A compound (4.00 g, 10.33 mmol) in MeOH (10 mL) saturated with ammonia gas under argon at 40–45° C. was treated with additional ammonia gas for 1 h. The slurry was cooled to 5° C. and trimethylsilylcyanide (2.1 mL, 15.7 mmol) was added over 10 min. The temperature was then raised to 45° C. as a yellow solution formed. After 7 h, the reaction mixture was evaporated, re-dissolved in EtOH (60 mL) and hydrogen chloride gas was used to saturate the solution. After 14 h, the reaction mixture was treated with thionyl chloride (0.8 mL) and warmed to 55° C. for 2 h. The solution was cooled to room temperature, evaporated and the resulting solids triturated in Et$_2$O to give the title compound as an orange solid, usable without further purification.

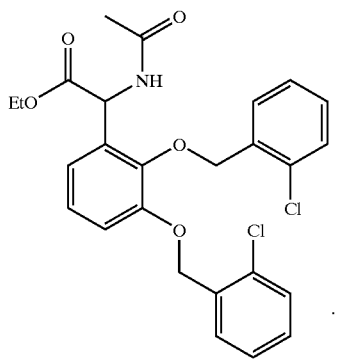

B

To a stirred solution of Part A compound (197 mg, 0.4 mmol) under argon at room temperature in THF (2 mL) was added triethylamine (0.2 mL, 1.6 mmol), DMAP (2 mg, 0.02 mmol) and acetic anhydride (60 µL, 0.6 mmol). After 15 h, the reaction mixture was diluted with EtOAc, washed once with 10% citric acid, dried (MgSO$_4$) and evaporated. Purification by flash chromatography on silica gel provided the title compound as a colorless oil, 167 mg (83% yield). LC/MS gave the correct molecular ion [(M+H)$^+$=502] for the desired compound.

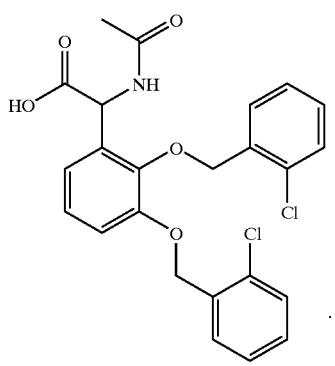

C

To a stirred solution of Part B compound (167 mg, 0.33 mmol) in THF (1 mL) at room temperature under argon was added sodium hydroxide solution (0.5 mL, 1 M, 0.5 mmol). After 14 h, the solution was diluted with water and extracted once with Et$_2$O. The aqueous phase was cooled, acidified to pH 2 with 1 N HCl and the resulting precipitate was filtered, washed with water and air-dried to give the title compound as a white amorphous solid, 104 mg (55% yield). LC/MS gave the correct molecular ion [(M+H)$^+$=474] for the desired compound.

EXAMPLE 14

2,3-Bis[(2-chlorophenyl)methoxy]-α-[(2-methyl-1-oxopropyl)amino]benzeneacetic acid

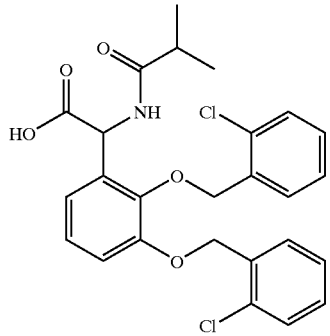

A

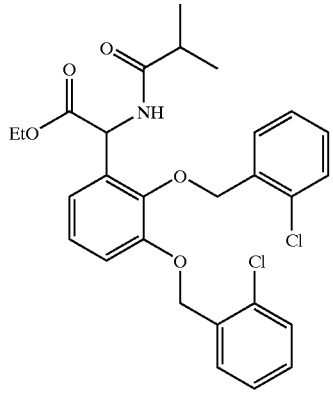

To a stirred solution of Example 13 Part A compound (197 mg, 0.4 mmol) under argon at 0–5° C. in THF (1.5 mL) was added triethylamine (0.2 mL, 1.6 mmol), DMAP (2 mg, 0.02 mmol) and isobutyryl chloride (65 µL, 0.6 mmol). The reaction mixture was allowed to warm to room temperature and after 15 h, it was diluted with EtOAc, washed once with 10% citric acid, dried (MgSO$_4$) and evaporated. Purification by flash chromatography on silica gel provided the title compound as a colorless oil, 156 mg (74% yield). LC/MS gave the correct molecular ion [(M+H)$^+$=530] for the desired compound.

C

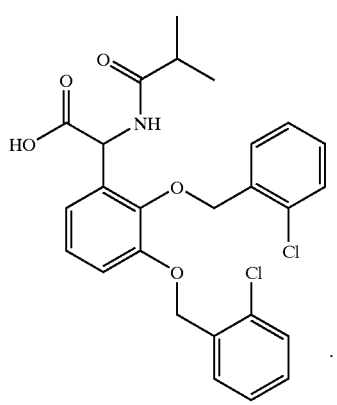

To a stirred solution of Part B compound (155 mg, 0.29 mmol) in THF (1 mL) at room temperature under argon was added sodium hydroxide solution (0.5 mL, 1 M, 0.5 mmol). After 24 h, the solution was diluted with water and extracted once with Et$_2$O. The aqueous phase was cooled, acidified to pH 2 with 1 N HCl and the resulting precipitate was filtered, washed with water and air-dried to give the title compound as a white amorphous solid, 156 mg (100% yield). LC/MS gave the correct molecular ion [(M+H)$^+$=502] for the desired compound.

EXAMPLE 15

α-(Benzoylamino)-2,3-bis[(2-chlorophenyl)methoxy]benzeneacetic acid

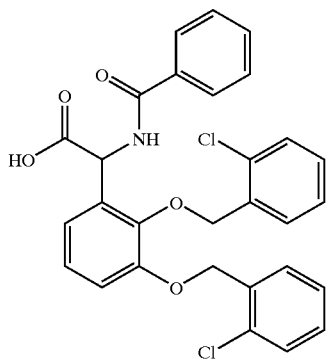

A

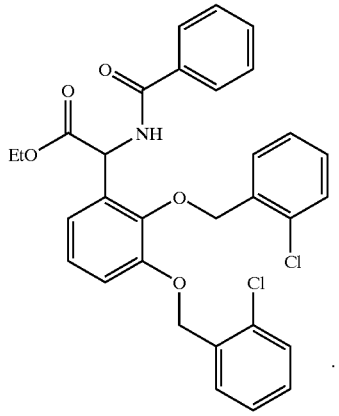

To a stirred solution of Example 13 Part A compound (197 mg, 0.4 mmol) under argon at 0–5° C. in THF (1.5 mL) was added triethylamine (0.2 mL, 1.6 mmol), DMAP (2 mg, 0.02 mmol) and benzoyl chloride (70 μL, 0.6 mmol). The reaction mixture was allowed to warm to room temperature and after 15 h, it was diluted with EtOAc, washed once with 10% citric acid, dried (MgSO$_4$) and evaporated. Purification by flash chromatography on silica gel provided the title compound as a colorless oil, 161 mg (71% yield). LC/MS gave the correct molecular ion [(M+H)$^+$=564] for the desired compound.

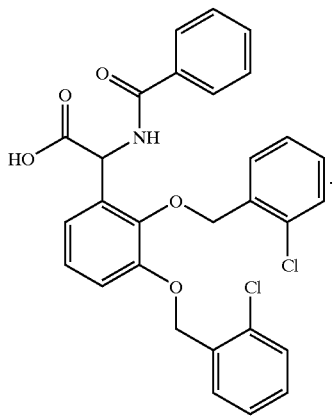

C

To a stirred solution of Part B compound (160 mg, 0.28 mmol) in THF (1 mL) at room temperature under argon was added sodium hydroxide solution (0.5 mL, 1 M, 0.5 mmol). After 24 h, the solution was diluted with water and extracted once with Et$_2$O. The aqueous phase was cooled, acidified to pH 2 with 1 N HCl and the resulting precipitate was filtered, washed with water and air-dried to give the title compound as a tan amorphous solid, 142 mg (95% yield). LC/MS gave the correct molecular ion [(M+H)$^+$=536] for the desired compound.

EXAMPLE 16

2,3-Bis[(2-chlorophenyl)methoxy]-α-[(difluoroacetyl)amino]benzeneacetic acid

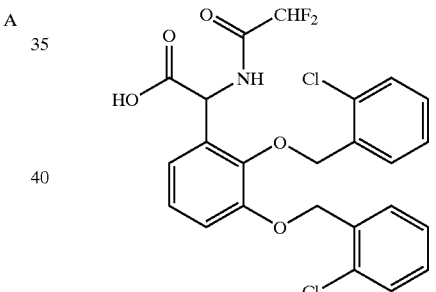

A

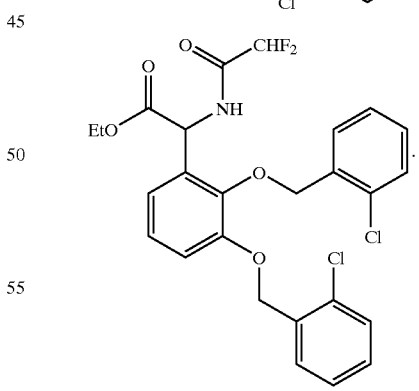

To a stirred solution of Example 13 Part A compound (222 mg, 0.45 mmol) under argon at room temperature in CH$_2$Cl$_2$ (2.5 mL) was added triethylamine (85 μL, 0.6 mmol), HOAt (69 mg, 0.5 mmol) and difluoroacetic acid (48 mg, 0.5 mmol) was added EDAC (96 mg, 0.5 mmol). After 16 h, the reaction mixture was diluted with EtOAc, washed once with 10% citric acid, dried (MgSO$_4$) and evaporated. Purification by flash chromatography on silica gel provided the title compound as a colorless oil, 156 mg (64% yield). LC/MS gave the correct molecular ion [(M+H)$^+$=538] for the desired compound.

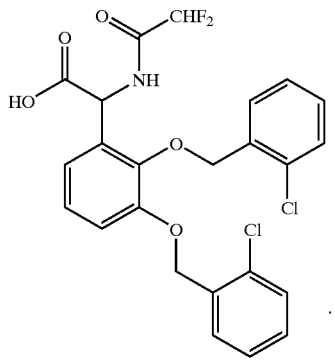

To a stirred solution of Part B compound (153 mg, 0.28 mmol) in THF (1.5 mL) at room temperature under argon was added a solution of lithium hydroxide monohydrate (13 mg, 0.32 mmol) in water (1 mL). After 24 h, the solution was diluted with water and extracted once with Et$_2$O. The aqueous phase was cooled, acidified to pH 2 with 1 N HCl and the resulting precipitate was filtered, washed with water and air-dried to give the title compound as an off-white amorphous solid, 144 mg (100% yield). LC/MS gave the correct molecular ion [(M+H)$^+$=510] for the desired compound.

EXAMPLE 17

α-[(aminoacetyl)amino]-2,3-bis[(2-chlorophenyl)methoxy]benzeneacetic acid hydrochloride

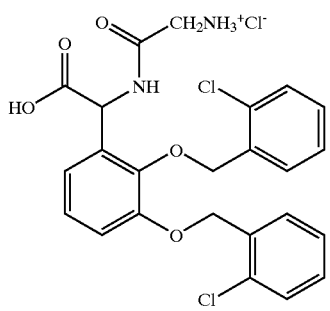

A

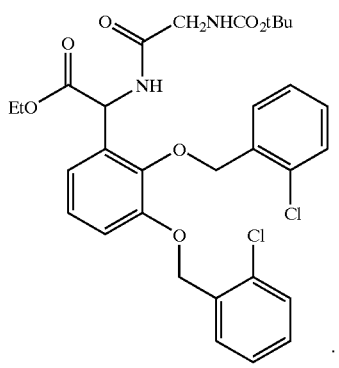

To a stirred solution of N-t-butyloxycarbonyl glycine under argon at −5° C. in THF (2 mL) was added triethylamine (60 μL, 0.5 mmol) and then isobutyl chloroformate (67 μL, 0.52 mL). The resulting slurry was stirred 20 min and a solution of Example 13 Part A compound (222 mg, 0.45 mmol) and triethylamine (70 μL, 0.6 mmol) in THF (1 mL) was added over 1 min. The reaction was allowed to warm to room temperature and stirred. After 1 h, the reaction mixture was diluted with EtOAc, washed once with 10% citric acid, dried (MgSO$_4$) and evaporated. Purification by flash chromatography on silica gel provided the title compound as a colorless oil, 102 mg (37% yield). LC/MS gave the correct molecular ion [(M+H)$^+$=617] for the desired compound.

C

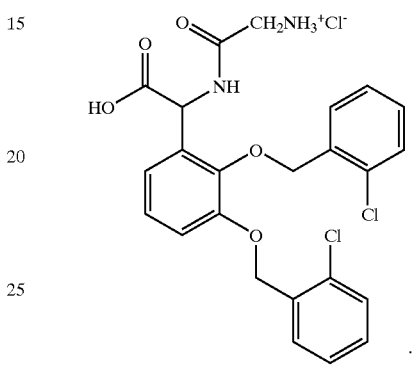

To a stirred solution of Part B compound (102 mg, 0.17 mmol) in THF (1 mL) at room temperature under argon was added sodium hydroxide solution (0.3 mL, 1 M, 0.3 mmol). After 20 h, the reaction mixture was acidified to pH 2 with 1 N HCl and extracted with CH$_2$Cl$_2$. The extract was dried (MgSO$_4$), evaporated and then stirred with 4 N HCl/dioxane (1 mL) for 4 h. The solution was evaporated, the residue triturated with Et$_2$O and collected to provide the title compound as an off-white amorphous solid, 90 mg (100% yield). LC/MS gave the correct molecular ion [(M+H)$^+$=489] for the desired compound.

EXAMPLE 18

2,3-Bis[(2-chlorophenyl)methoxy]-α-[(methoxyacetyl)amino]benzeneacetic acid

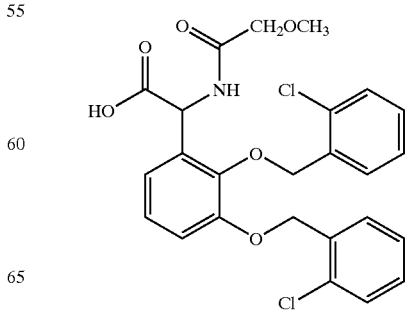

A

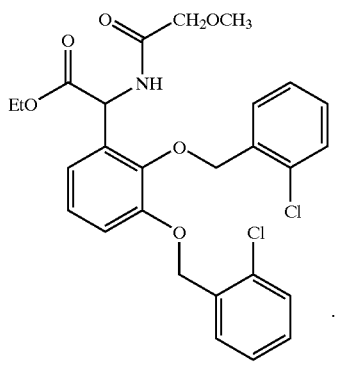

To a stirred solution of Example 13 Part A compound (222 mg, 0.45 mmol) under argon at room temperature in CH$_2$Cl$_2$ (1.5 mL) was added triethylamine (85 μL, 0.6 mmol), HOAt (69 mg, 0.5 mmol) and methoxyacetic acid (46 mg, 0.5 mmol) was added EDAC (96 mg, 0.5 mmol). After 16 h, the reaction mixture was diluted with EtOAc, washed once with 10% citric acid, dried (MgSO$_4$) and evaporated. Purification by flash chromatography on silica gel provided the title compound as a colorless oil, 153 mg (74% yield). LC/MS gave the correct molecular ion [(M+H)$^+$=518] for the desired compound.

C

[structure of Part B / C compound: carboxylic acid analog]

To a stirred solution of Part B compound (153 mg, 0.29 mmol) in THF (2 mL) at room temperature under argon was added a solution of lithium hydroxide monohydrate (13 mg, 0.32 mmol) in water (1 mL). After 24 h, the solution was diluted with water and extracted once with Et$_2$O. The aqueous phase was cooled, acidified to pH 2 with 1 N HCl and the resulting precipitate was filtered, washed with water and air-dried to give the title compound as an off-white amorphous solid, 120 mg (82% yield). LC/MS gave the correct molecular ion [(M+H)$^+$=504] for the desired compound.

EXAMPLE 19

[2,3-Bis[(2-chlorophenyl)methoxy]phenyl] propanedioic acid

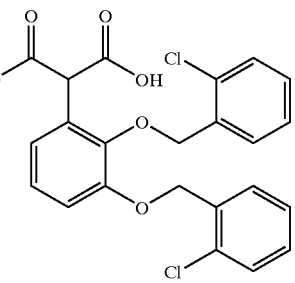

To a stirred solution of diisopropylamine (160 μL, 1.14 mmol) under argon at −5° C. in THF (3 mL) was added n-butyllithium solution (0.43 mL, 2.5 M in hexanes, 1.08 mmol). After 15 min, a solution of Example 5 Part E compound (209 mg, 0.5 mmol) in THF (1 mL) was added over 2 min. After 40 min, dry CO$_2$ gas was bubbled through the solution for 20 min. The reaction mixture was diluted with EtOAc, washed once with 10% citric acid, dried (MgSO$_4$) and evaporated. Purification by reverse phase preparative HPLC (YMC S5 ODS 20×250 mm column, acetonitrile/water–0.1% TFA gradient) provided the title compound as a light yellow oil, 164 mg (71% yield). LC/MS gave the correct molecular ion [(M+H)$^+$=461] for the desired compound.

EXAMPLE 20

[[2,3-Bis[(2-chlorophenyl)methoxy]phenyl]methyl]-α-(hydroxymethyl)benzeneacetic acid

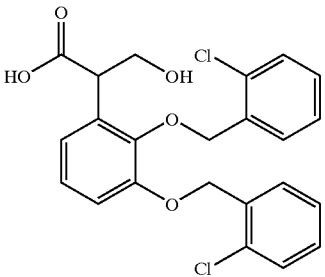

To a stirred solution of diisopropylamine (160 μL, 1.14 mmol) under argon at −5° C. in THF (3 mL) was added n-butyllithium solution (0.43 mL, 2.5 M in hexanes, 1.08 mmol). After 15 min, the reaction mixture was cooled to −78° C. and a solution of Example 5 Part E compound (209 mg, 0.5 mmol) in THF (1 mL) was then added over 2 min. After an additional 15 min, DMPU was added (2 mL) and the solution warmed to 0° C. Formaldehyde gas (by the pyrolysis of paraformaldehyde [300 mg, 10 mmol] at 190° C.) was introduced to the reaction mixture by a gas inlet tube. The reaction mixture was stirred for 1 h, diluted with EtOAc, washed once with 5% potassium hydrogen sulfate, dried (MgSO$_4$) and evaporated. Purification by flash chromatography on silica gel (1:39:360 HOAc/MeOH/CH$_2$Cl$_2$ as elutent) provided the title compound as a white solid, 136 mg (61% yield). LC/MS gave the correct molecular ion [(M+H)$^+$=447] for the desired compound.

EXAMPLE 21

3-[1-(2-Chlorophenyl)ethoxy]-2-[(2-chlorophenyl)methoxy]-α-hydroxybenzeneacetic acid

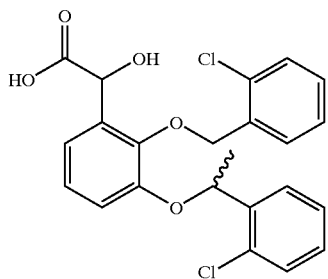

To a stirred solution of diisopropylamine (170 μL, 1.21 mmol) under argon at −5° C. in THF (3 mL) was added n-butyllithium solution (483 μL, 2.5 M in hexanes, 1.21 mmol). After 15 min, the reaction mixture was cooled to −78° C. and a solution of Example 1 Part B compound (248 mg, 0.537 mmol) in THF (1 mL) was then added over 2 min. After an additional 15 min, DMPU was added (2 mL) and then methyl iodide (42 μL, 0.68 mmol). The reaction mixture was stirred for 2 h and then warmed to −40° C. After 14 h, the reaction was quenched with sodium hydroxide solution (1 M), warmed to room temperature and stirred for 1 h. The reaction mixture was acidified with 5% potassium hydrogen sulfate, extracted with CH$_2$Cl$_2$, dried (MgSO$_4$) and evaporated. Purification by reverse phase preparative HPLC (YMC S5 ODS 20×250 mm column, acetonitrile/water−0.1% TFA gradient) provided the title compound, a colorless oil, as a 1:1 mixture of diastereomers, 75 mg (31% yield). LC/MS gave the correct molecular ion [(M+H)$^+$=447] for the desired compound.

EXAMPLE 22

2,3-Bis[(2-chlorophenoxy)methyl]-α-hydroxybenzeneacetic acid

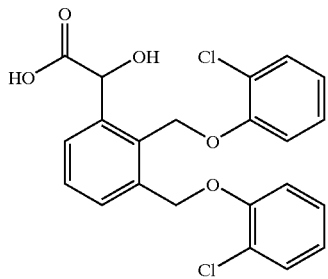

A

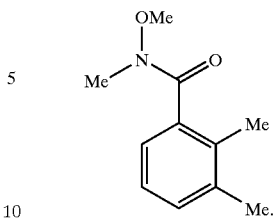

To a stirred solution of 2,3-dimethylbenzoic acid (1.50 g, 10 mmol) in CH$_2$Cl$_2$ (10 mL) under argon at room temperature was added oxalyl chloride solution (8.0 mL, 2 M in CH$_2$Cl$_2$, 16 mmol) and then DMF (0.2 mL). After 2 h, the solution was evaporated and re-evaporated twice from CH$_2$Cl$_2$ and then dissolved in CH$_2$Cl$_2$ (10 mL). This solution was added, over 30 min, to a stirred slurry of N-methoxy-N-methylammonium chloride (1.10 g, 11 mmol), DMAP (5 mg, 0.04 mmol) and triethylamine (3.0 mL, 21.4 mmol) in CH$_2$Cl$_2$ (15 mL) at 10° C. After the addition was complete, the reaction was allowed to warm to room temperature and stirred for 16 h. The reaction mixture was then diluted with CH$_2$Cl$_2$, washed once with 10% citric acid, once with water and once with brine. The organic extract was dried (MgSO$_4$) and evaporated. Purification by flash chromatography on silica gel provided the title compound as a colorless oil, 1.38 g (71% yield). LC/MS gave the correct molecular ion [(M+H)$^+$=194] for the desired compound.

B

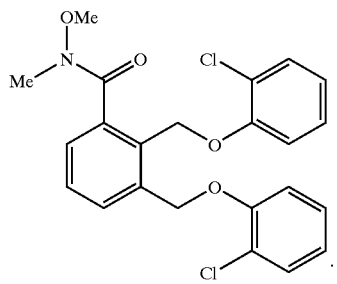

To a stirred solution of part A compound (1.32 g, 6.83 mmol) in carbon tetrachloride (20 mL) under argon was added freshly recrystallized N-bromosuccinimide (3.10 g, 13.7 mmol) and AIBN (50 mg). The reaction mixture was heated to reflux under argon for 3 h and then cooled and filtered. Purification by flash chromatography on silica gel provided predominantly N-methoxy-N-methyl 2,3-bis(bromomethyl) benzamide as a colorless oil, 1.08 g (45% yield).

To a stirred solution of 2-chlorophenol (1.06 mL, 10.2 mmol) in DMF (10 mL) at room temperature under argon was added sodium hydride (60% mineral oil dispersion, 385 mg, 9.6 mmol) over 5 min. The resulting clear solution was stirred 30 min and a solution in DMF (5 mL) of the dibromide prepared above was added and the reaction mixture heated to 65° C. After 1 h, the reaction mixture was quenched with water and extracted three times with Et$_2$O. The extracts were combined and washed twice with water, once with brine, dried (MgSO$_4$) and evaporated. Purification by flash chromatography on silica gel provided the title compound as a light yellow oil, 1.11 g (83% yield). LC/MS gave the correct molecular ion [(M+H)⁺=446] for the desired compound.

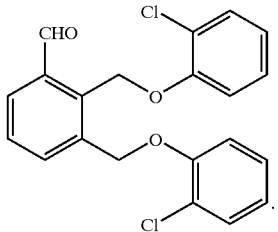
C

To a solution of Part B compound (2.56 g, 5.75 mmol) in THF (30 mL) at −78° C. under argon was added diisobutylaluminum hydride solution (7.6 mL, 1.5 M in toluene, 11.4 mmol) over 10 min. The reaction was stirred for 1 h and then warmed to room temperature and stirred for 2 h. The reaction mixture was then quenched with water (2 mL) and then stirred with potassium sodium tartrate solution (20 mL, 1 M) for 1 h. The mixture was extracted twice with EtOAc, the organic phases combined, dried (MgSO₄) and evaporated. Purification by flash chromatography on silica gel provided the title compound as a white solid, 1.58 g (71% yield), mp 101–103° C. LC/MS gave the correct molecular ion [(M+H)⁺=387] for the desired compound.

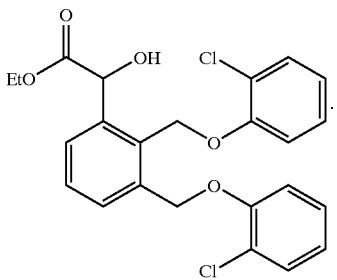
D

By the method of Example 1 Part B, Part C compound (532 mg, 1.37 mmol) was converted to the title compound as an amorphous white solid, 425 mg (67% yield). LC/MS gave the correct molecular ion [(M+H)⁺=461] for the desired compound.

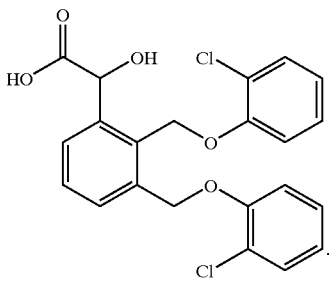
E

By the method of Example 1 Part C, Part D compound (413 mg, 0.90 mmol) was converted to the title compound as a white powder, 410 mg (100% yield). LC/MS gave the correct molecular ion [(M+H)⁺=433] for the desired compound as the protonated acid.

EXAMPLE 23

2,3-Bis[(2-chlorophenyl)methoxy]-α-mercaptobenzeneacetic acid

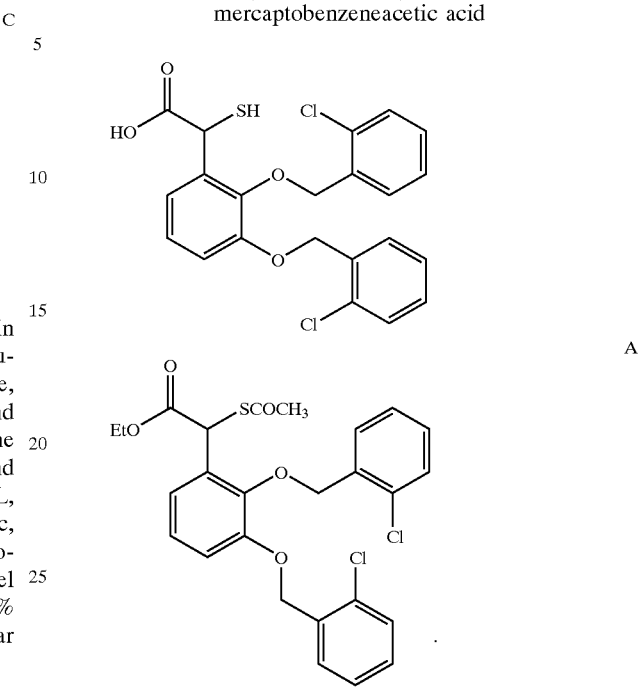

To a stirred solution of Example 1 Part B compound (462 mg, 1.00 mmol) in CH₂Cl₂ (5 mL) under argon at room temperature was added thionyl chloride (80 µL, 1.1 mmol) and then DMF (80 µL, 1.0 mmol) over 2 min. The reaction mixture was stirred for 1 h, then quenched with saturated sodium bicarbonate solution and extracted twice with CH₂Cl₂. The extracts were combined, dried (MgSO₄) and evaporated. The residuum was immediately dissolved in EtOH (5 mL) and added to a solution prepared from thiolacetic acid (0.35 mL, 4.9 mmol) and potassium t-butoxide (539 mg, 4.8 mmol) in EtOH (5 mL). After 16 h, the reaction mixture was quenched with water and extracted three times with EtOAc. The organic extracts were combined, dried (MgSO₄) and evaporated. Purification by flash chromatography on silica gel provided the title compound as a colorless oil, 330 mg (64% yield). LC/MS gave the correct molecular ion [(M+H)⁺=519] for the desired compound.

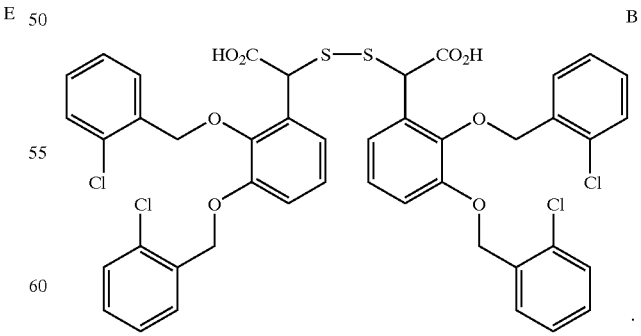
B

To a stirred solution of part A compound (330 mg, 0.64 mmol) in nitrogen-purged THF (5 mL) at room temperature was added sodium hydroxide solution (3.0 mL, 1 M, 3.0 mmol). After 24 h, the reaction was quenched with 10% citric acid and extracted twice with EtOAc. The extracts were combined, dried (MgSO₄) and evaporated to provide predominantly the title compound as a colorless oil, 255 mg (89% yield). LC/MS gave the correct molecular ion [(M+H)⁺=894] for the desired compound.

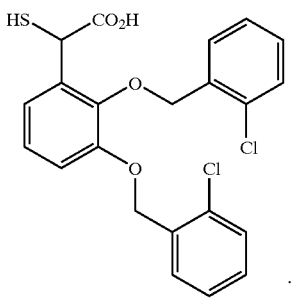

C

To a solution of Part B compound (52 mg, 0.058 mmol) in THF (2 mL) and water (2 mL) at room temperature under argon was added tributylphosphine (50 μL, 0.2 mmol). The reaction was stirred for 5 min and then purified directly by reverse phase preparative HPLC (YMC S5 ODS 20×250 mm column, acetonitrile/water–TFA elutant) to give the title compound as a colorless oil, 32 mg, 62% yield. LC/MS gave the correct molecular ion [(M+H)⁺=449] for the desired compound.

EXAMPLE 24

2,3-Bis[(2-chlorophenyl)methoxy]-α-fluorobenzeneacetic acid

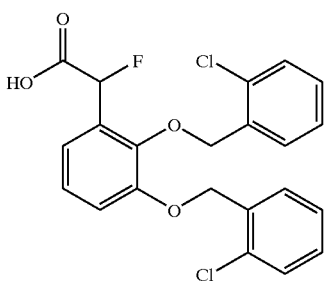

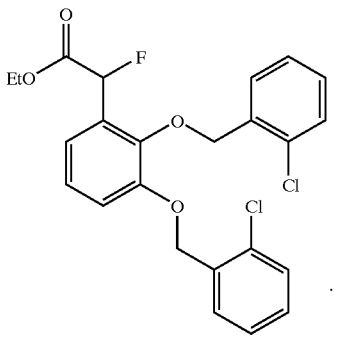

A

To a stirred solution of Example 1 Part B compound (461 mg, 1.00 mmol) in CH₂Cl₂ (10 mL) under argon at 0° C. was added a solution of diethylaminosulfur trifluoride [DAST] (265 μL, 2.0 mmol) in CH₂Cl₂ (5 mL) over 20 min. The reaction mixture was stirred for an additional 45 min, then quenched with saturated sodium bicarbonate solution and extracted twice with CH₂Cl₂. The extracts were combined, dried (MgSO₄) and evaporated. Purification by flash chromatography on silica gel provided the title compound as a light yellow oil, 218 mg (47% yield). LC/MS gave the correct molecular ion [(M+H)⁺=463] for the desired compound.

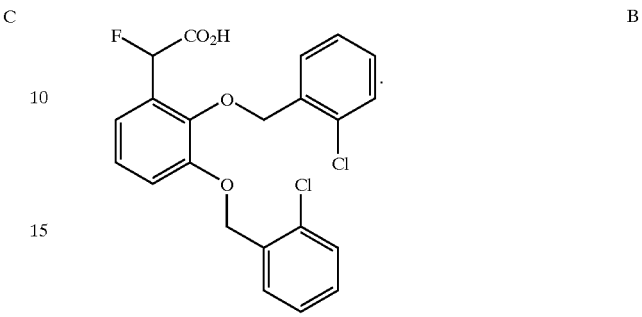

B

To a stirred solution of part A compound (218 mg, 0.47 mmol) in MeOH (2 mL) and THF (2 mL) at room temperature under argon was added sodium hydroxide solution (2.0 mL, 1 M, 2.0 mmol). After 14 h, the reaction was diluted with water and extracted once with ether. The aqueous phase was brought to pH 2 with 5% potassium hydrogen sulfate solution. The resulting solids were collected, washed with water and air-dried to give the title compound as a white solid, 202 mg (98% yield), mp 92–94° C. LC/MS gave the correct molecular ion [(M+H)⁺=435] for the desired compound.

EXAMPLE 25

3-[(2-Chlorophenyl)methoxy]-2-hydroxybenzoic acid ethyl ester

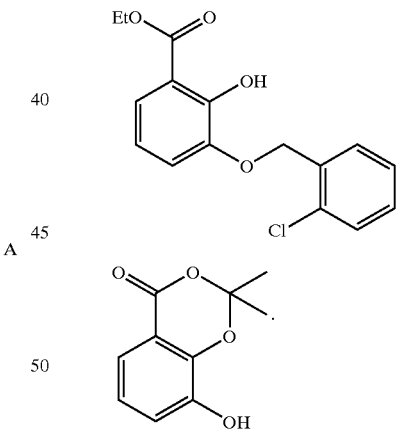

A

To a stirred solution of trifluoroacetic acid (200 mL) and trifluoroacetic anhydride (100 mL) at −4° C. was added 2,3-dihydroxybenzoic acid (20.0 g, 130 mmol) over 5 min. To this slurry was added acetone (34 mL, 460 mmol) over the course of 1 h. After an additional 3 h, the reaction was allowed to warm to room temperature in situ and stirred 4 h. The resulting solution was evaporated and the resulting residue poured into ice water (300 mL). Solid sodium bicarbonate was added portionwise until the solution reached ~pH 9. The gummy residue was extracted into EtOAc (300 mL) and the aqueous phase was extracted twice with EtOAc. The extracts were combined, washed once with brine, dried (Na₂SO₄) and evaporated. Purification by flash chromatography on silica gel provided the title compound 9.87 g (39% yield). LC/MS gave the correct molecular ion [(M+H)⁺=197] for the desired compound.

B

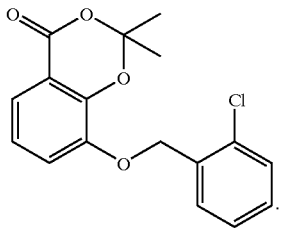

To a stirred solution of part A compound (3.0 g, 15.4 mmol) in DMF (26 mL) at room temperature under argon was added 2-chlorobenzyl chloride (2.3 mL, 18.2 mmol), potassium carbonate (3.2 g, 23 mmol) and tetrabutylammonium iodide (57 mg, 0.15 mmol). The mixture was heated to 50° C. and stirred for 2 h. After cooling to room temperature, the reaction was filtered through Celite® and poured into Et$_2$O (250 mL). The solution was washed three times with water and once with brine. After drying (Na$_2$SO$_4$) and evaporation, the title compound was isolated and used in part C without further purification (5.47 g, >100% yield).

C

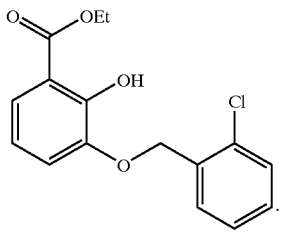

To a stirred solution of part B compound (5.47 g, ~15.4 mmol) in THF (100 mL) at room temperature under argon was added a 25% solution of sodium ethoxide in ethanol (4.5 mL, 16 mmol) and the mixture was stirred at room temperature for 1 h. The mixture was then diluted with water (400 mL) and ethyl acetate (400 mL). The suspension was treated with 50 mL of 1 N hydrochloric acid and the organic fraction was washed with brine, dried (MgSO$_4$) and evaporated to an oil (4.65 g, 85% yield.

EXAMPLE 26

2,3-Bis[(2-chlorophenyl)methoxy]-α-oxobenzeneacetic acid

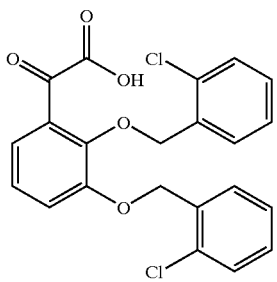

A

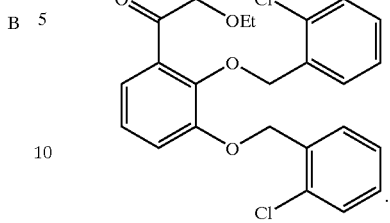

To a stirred solution of Example 1 Part B compound (400 mg, 0.867 mmol) in DMSO (1 mL) at 90° C. was added acetic anhydride (0.1 mL, 1 mmol) over 1 h. After an additional 3 h, the reaction mixture was cooled, diluted with water and extracted three times with ether. The organic extracts were combined, washed with brine, dried (Na$_2$SO$_4$) and evaporated. Purification by flash chromatography on silica gel provided the title compound, 382 mg (96% yield). LC/MS gave the correct molecular ion [(M+Na)⁺=481] for the desired compound.

B

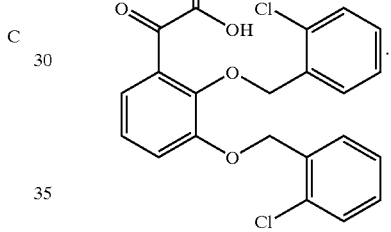

To a stirred solution of Part A compound (67 mg, 0.15 mmol) in THF (0.3 mL) at room temperature under argon was added sodium hydroxide solution (0.3 mL, 1 M, 0.3 mmol). After 18 h, the reaction mixture was diluted with water and extracted three times with ether. The aqueous layer was cooled to 5° C., acidified to pH 3 with 1 M hydrochloric acid and extracted three times with ether. The acidicified organic extracts were combined, dried (Na$_2$SO$_4$) and evaporated to provide the title compound as a white solid, 55 mg (86% yield), mp 116–118° C. LC/MS gave the correct molecular ion [(M+H)⁺=431] for the desired compound.

EXAMPLE 27

2,3-Bis[(2-chlorophenyl)methoxy]-α,α-difluorobenzeneacetic acid

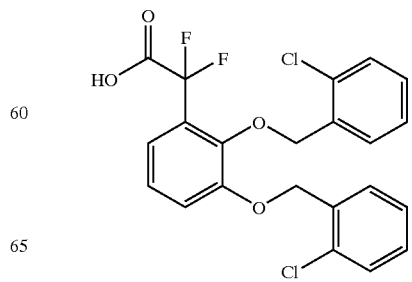

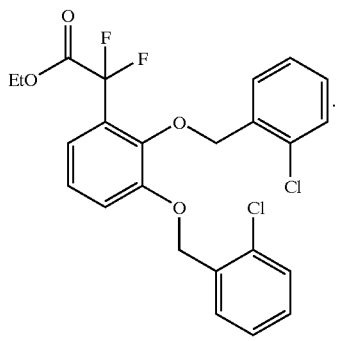

To a stirred solution of Example 26 Part A compound (256 mg, 0.557 mmol) in CH$_2$Cl$_2$ (100 μL) under argon at room temperature was added DAST (160 μL, 1.2 mmol). The reaction mixture was stirred for 22 h, the reaction mixture was quenched with water and extracted three times with CH$_2$Cl$_2$. The organic extracts were combined, dried (MgSO$_4$) and evaporated. Purification by flash chromatography on silica gel provided the title compound as a white solid, 197 mg (74% yield), mp 55–57° C. LC/MS gave the correct molecular ion [(M+H)$^+$=481] for the desired compound.

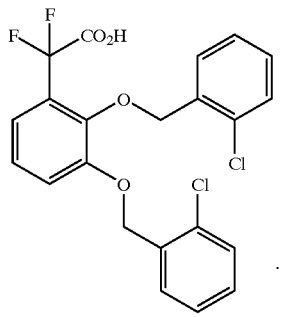

To a stirred solution of part A compound (195 mg, 0.41 mmol) in THF (2 mL) at room temperature under argon was added sodium hydroxide solution (0.6 mL, 1 M, 0.6 mmol). After 15 h, the reaction was diluted with water and extracted once with ether. The aqueous phase was brought to pH 2 with 5% potassium hydrogen sulfate solution. The resulting solids were collected, washed with water and air-dried to give the title compound as a white solid, 168 mg (92% yield), mp 113–115° C. LC/MS gave the correct molecular ion [(M+H)$^+$=453] for the desired compound.

EXAMPLES 28–336

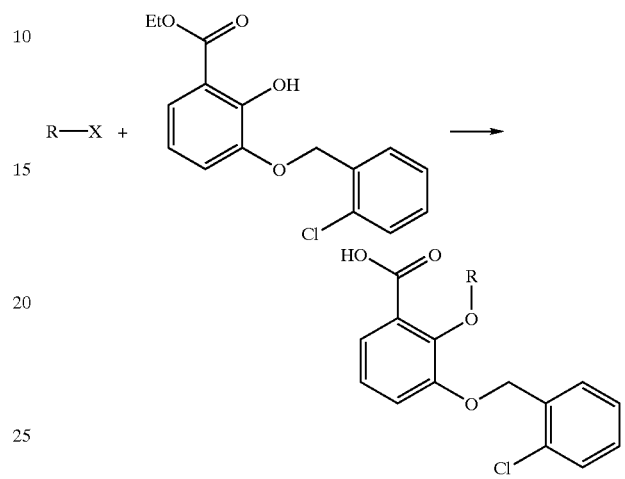

Sealable reaction vessels were each charged with potassium carbonate (32 mg, 0.23 mmol), tetrabutylammonium iodide (~1 mg) and DMF (244 μL). A solution of Example 25 Part C compound (489 μL, 0.2 M in DMF, 0.0978 mmol) and of R-X (0.147 mmol, 0.2 M in THF) was added and the reaction vessels were agitated and heated to 60° C. After 14 h, the reactions were cooled to room temperature and EtOH (2 mL) was added to each reaction, followed by a solution of sodium hydroxide in ethanol (733 μL, 0.3 M, 0.2 mmol). The reactions were heated again at 60° C. for 5 h and cooled to room temperature. The contents of each reaction vessel were diluted with MeOH (~2 mL) and purified by reverse phase preparative HPLC (YMC S5 ODS 20×100 mm column, MeOH/water-TFA elutant) to give the title compound. Mass spectrometric and HPLC data were collected for all compounds.

Following the above procedure, the following compounds of the invention were prepared:

| Ex. | CAS Name | Elemental formula | Mass Spec. m/z | ion type inferred |
|---|---|---|---|---|
| 28 | 2-[(2-Bromophenyl)methoxy]-3-[(2-chlorophenyl)methoxy]benzoic acid | C21 H16 Br Cl O4 | 466 | [M + NH$_4$] |
| 29 | 3-[(2-Chlorophenyl)methoxy]-2-[(2-methylphenyl)methoxy]benzoic acid | C22 H19 Cl O4 | 400 | [M + NH$_4$] |
| 30 | 3-[(2-Chlorophenyl)methoxy]-2-[(3-methylphenyl)methoxy]benzoic acid | C22 H19 Cl O4 | 400 | [M + NH$_4$] |
| 31 | 2-[(4-Bromophenyl)methoxy]-3-[(2-chlorophenyl)methoxy]benzoic acid | C21 H16 Br Cl O4 | 466 | [M + NH$_4$] |
| 32 | 3-[(2-Chlorophenyl)methoxy]-2-[[4-(1,1-dimethylethyl)phenyl]methoxy]benzoic acid | C25 H25 Cl O4 | 442 | [M + NH$_4$] |

-continued

| Ex. | CAS Name | Elemental formula | Mass Spec. m/z | ion type inferred |
|---|---|---|---|---|
| 33 | 3-[(2-Chlorophenyl)methoxy]-2-[(4-methylphenyl)methoxy]benzoic acid | C22 H19 Cl O4 | 400 | [M + NH4] |
| 34 | 3-[(2-Chlorophenyl)methoxy]-2-[(2-fluorophenyl)methoxy]benzoic acid | C21 H16 Cl F O4 | 404 | [M + NH4] |
| 35 | 3-[(2-Chlorophenyl)methoxy]-2-[(2,6-difluorophenyl)methoxy]benzoic acid | C21 H15 Cl F2 O4 | 422 | [M + NH4] |
| 36 | 3-[(2-Chlorophenyl)methoxy]-2-[(3-fluorophenyl)methoxy]benzoic acid | C21 H16 Cl F O4 | 404 | [M + NH4] |
| 37 | 3-[(2-Chlorophenyl)methoxy]-2-[(4-fluorophenyl)methoxy]benzoic acid | C21 H16 Cl F O4 | 404 | [M + NH4] |
| 38 | 3-[(2-Chlorophenyl)methoxy]-2-[[3-(trifluoromethyl)phenyl]methoxy]benzoic acid | C22 H16 Cl F3 O4 | 454 | [M + NH4] |
| 39 | 3-[(2-Chlorophenyl)methoxy]-2-[[4-(trifluoromethyl)phenyl]methoxy]benzoic acid | C22 H16 Cl F3 O4 | 454 | [M + NH4] |
| 40 | 3-[(2-Chlorophenyl)methoxy]-2-[(2,6-dichlorophenyl)methoxy]benzoic acid | C21 H15 Cl3 O4 | 454 | [M + NH4] |
| 41 | 2-[(3-Chlorophenyl)methoxy]-3-[(2-chlorophenyl)methoxy]benzoic acid | C21 H16 Cl2 O4 | 420 | [M + NH4] |
| 42 | 3-[(2-Chlorophenyl)methoxy]-2-[(2,4-dichlorophenyl)methoxy]benzoic acid | C21 H15 Cl3 O4 | 454 | [M + NH4] |
| 43 | 2-[(2-Chloro-6-fluorophenyl)methoxy]-3-[(2-chlorophenyl)methoxy]benzoic acid | C21 H15 Cl2 F O4 | 438 | [M + NH4] |
| 44 | 3-[(2-Chlorophenyl)methoxy]-2-[(2,4,6-trimethylphenyl)methoxy]benzoic acid | C24 H23 Cl O4 | 428 | [M + NH4] |
| 45 | 3-[(2-Chlorophenyl)methoxy]-2-[(2,5-dimethylphenyl)methoxy]benzoic acid | C23 H21 Cl O4 | 414 | [M + NH4] |
| 46 | 3-[(2-Chlorophenyl)methoxy]-2-[(3,4-dichlorophenyl)methoxy]benzoic acid | C21 H15 Cl3 O4 | 454 | [M + NH4] |
| 47 | 3-[(2-Chlorophenyl)methoxy]-2-[(3-methoxyphenyl)methoxy]benzoic acid | C22 H19 Cl O5 | 416 | [M + NH4] |
| 48 | 3-[(2-Chlorophenyl)methoxy]-2-[(4-methoxyphenyl)methoxy]benzoic acid | C22 H19 Cl O5 | 416 | [M + NH4] |
| 49 | 3-[(2-Chlorophenyl)methoxy]-2-[[4-(phenylmethoxy)phenyl]methoxy]benzoic acid | C28 H23 Cl O5 | 492 | [M + NH4] |
| 50 | 2-([1,1'-Biphenyl]-4-ylmethoxy)-3-[(2-chlorophenyl)methoxy]benzoic acid | C27 H21 Cl O4 | 462 | [M + NH4] |
| 51 | 3-[(2-Chlorophenyl)methoxy]-2-[(2-cyanophenyl)methoxy]benzoic acid | C22 H16 Cl N O4 | 411 | [M + NH4] |
| 52 | 3-[(2-Chlorophenyl)methoxy]-2-[(3-cyanophenyl)methoxy]benzoic acid | C22 H16 Cl N O4 | 411 | [M + NH4] |
| 53 | 3-[(2-Chlorophenyl)methoxy]-2-[(4-cyanophenyl)methoxy]benzoic acid | C22 H16 Cl N O4 | 411 | [M + NH4] |
| 54 | 3-[(2-Chlorophenyl)methoxy]-2-(1-naphthalenylmethoxy)benzoic acid | C25 H19 Cl O4 | 436 | [M + NH4] |
| 55 | 3-[(2-Chlorophenyl)methoxy]-2-[(2-methyl-1-naphthalenyl)methoxy]benzoic acid | C26 H21 Cl O4 | 450 | [M + NH4] |
| 56 | 3-[(2-Chlorophenyl)methoxy]-2-(2-naphthalenylmethoxy)benzoic acid | C25 H19 Cl O4 | 436 | [M + NH4] |
| 57 | 2-[[3,4-Bis(phenylmethoxy)phenyl]methoxy]-3-[(2-chlorophenyl)methoxy]benzoic acid | C35 H29 Cl O6 | 598 | [M + NH4] |

-continued

| Ex. | CAS Name | Elemental formula | Mass Spec. m/z | ion type inferred |
|---|---|---|---|---|
| 58 | 2-[(6-Chloro-1,3-benzodioxol-5-yl)methoxy]-3-[(2-chlorophenyl)methoxy]benzoic acid | C22 H16 Cl2 O6 | 464 | [M + NH$_4$] |
| 59 | 3-[(2-Chlorophenyl)methoxy]-2-[(2-methyl-3-nitrophenyl)methoxy]benzoic acid | C22 H18 Cl N O6 | 445 | [M + NH$_4$] |
| 60 | 3-[(2-Chlorophenyl)methoxy]-2-[(2-nitrophenyl)methoxy]benzoic acid | C21 H16 Cl N O6 | 431 | [M + NH$_4$] |
| 61 | 3-[(2-Chlorophenyl)methoxy]-2-[(4-chloro-2-nitrophenyl)methoxy]benzoic acid | C21 H15 Cl2 N O6 | 446 | [M − H] |
| 62 | 3-[(2-Chlorophenyl)methoxy]-2-[(3-nitrophenyl)methoxy]benzoic acid | C21 H16 Cl N O6 | 431 | [M + NH$_4$] |
| 63 | 3-[(2-Chlorophenyl)methoxy]-2-[(2-methoxy-5-nitrophenyl)methoxy]benzoic acid | C22 H18 Cl N O7 | 461 | [M + NH$_4$] |
| 64 | 3-[(2-Chlorophenyl)methoxy]-2-[(5-methyl-2-nitrophenyl)methoxy]benzoic acid | C22 H18 Cl N O6 | 445 | [M + NH$_4$] |
| 65 | 3-[(2-Chlorophenyl)methoxy]-2-[(4-nitrophenyl)methoxy]benzoic acid | C21 H16 Cl N O6 | 412 | [M − H] |
| 66 | 3-[(2-Chlorophenyl)methoxy]-2-[[2-[(phenylsulfonyl)methyl]phenyl]methoxy]benzoic acid | C28 H23 Cl O6 S | 540 | [M + NH$_4$] |
| 67 | 3-[(2-Chlorophenyl)methoxy]-2-[(3,4-difluorophenyl)methoxy]benzoic acid | C21 H15 Cl F2 O4 | 403 | [M − H] |
| 68 | 3-[(2-Chlorophenyl)methoxy]-2-[(2,5-difluorophenyl)methoxy]benzoic acid | C21 H15 Cl F2 O4 | 422 | [M + NH$_4$] |
| 69 | 2-[[3,5-Bis(trifluoromethyl)phenyl]methoxy]-3-[(2-chlorophenyl)methoxy]benzoic acid | C23 H15 Cl F6 O4 | 522 | [M + NH$_4$] |
| 70 | 3-[(2-Chlorophenyl)methoxy]-2-[(3,5-difluorophenyl)methoxy]benzoic acid | C21 H15 Cl F2 O4 | 422 | [M + NH$_4$] |
| 71 | 3-[(2-Chlorophenyl)methoxy]-2-[(2,4-difluorophenyl)methoxy]benzoic acid | C21 H15 Cl F2 O4 | 422 | [M + NH$_4$] |
| 72 | 3-[(2-Chlorophenyl)methoxy]-2-[(3,5-dimethylphenyl)methoxy]benzoic acid | C23 H21 Cl O4 | 414 | [M + NH$_4$] |
| 73 | 3-[(2-Chlorophenyl)methoxy]-2-[(2,3,5,6-tetramethylphenyl)methoxy]benzoic acid | C25 H25 Cl O4 | 442 | [M + NH$_4$] |
| 74 | 3-[(2-Chlorophenyl)methoxy]-2-[(2,4-dimethylphenyl)methoxy]benzoic acid | C23 H21 Cl O4 | 395 | [M − H] |
| 75 | 3-[(2-Chlorophenyl)methoxy]-2-[[4-(1-methylethyl)phenyl]methoxy]benzoic acid | C24 H23 Cl O4 | 409 | [M − H] |
| 76 | 3-[(2-Chlorophenyl)methoxy]-2-[(3-iodophenyl)methoxy]benzoic acid | C21 H16 Cl I O4 | 512 | [M + NH$_4$] |
| 77 | 2-[(4-Carboxyphenyl)methoxy]-3-[(2-chlorophenyl)methoxy]benzoic acid | C22 H17 Cl O6 | 411 | [M − H] |
| 78 | 3-[(2-Chlorophenyl)methoxy]-2-[(2,3-dichlorophenyl)methoxy]benzoic acid | C21 H15 Cl3 O4 | 435 | [M − H] |
| 79 | 3-[(2-Chlorophenyl)methoxy]-2-[(2,5-dichlorophenyl)methoxy]benzoic acid | C21 H15 Cl3 O4 | 454 | [M + NH$_4$] |
| 80 | 3-[(2-Chlorophenyl)methoxy]-2-[(4-ethylphenyl)methoxy]benzoic acid | C23 H21 Cl O4 | 395 | [M − H] |
| 81 | 2-[(4-Chlorophenyl)methoxy]-3-[(2-chlorophenyl)methoxy]benzoic acid | C21 H16 Cl2 O4 | 420 | [M + NH$_4$] |

-continued

| Ex. | CAS Name | Elemental formula | Mass Spec. m/z | ion type inferred |
|---|---|---|---|---|
| 82 | 2-[(3-Bromophenyl)methoxy]-3-[(2-chlorophenyl)methoxy]benzoic acid | C21 H16 Br Cl O4 | 466 | [M + NH$_4$] |
| 83 | 3-[(2-Chlorophenyl)methoxy]-2-[(3-phenoxyphenyl)methoxy]benzoic acid | C27 H21 Cl O5 | 478 | [M + NH$_4$] |
| 84 | 3-[(2-Chlorophenyl)methoxy]-2-[(2-fluoro-3-methylphenyl)methoxy]benzoic acid | C22 H18 Cl F O4 | 418 | [M + NH$_4$] |
| 85 | 3-[(2-Chlorophenyl)methoxy]-2-[(2,3-difluorophenyl)methoxy]benzoic acid | C21 H15 Cl F2 O4 | 422 | [M + NH$_4$] |
| 86 | 2-[(3-Chloro-2-fluorophenyl)methoxy]-3-[(2-chlorophenyl)methoxy]benzoic acid | C21 H15 Cl2 F O4 | 438 | [M + NH$_4$] |
| 87 | 3-[(2-Chlorophenyl)methoxy]-2-[(9,10-dihydro-9,10-dioxo-2-anthracenyl)methoxy]benzoic acid | C29 H19 Cl O6 | 516 | [M + NH$_4$] |
| 88 | 3-[(2-Chlorophenyl)methoxy]-2-[(4-methyl-3-nitrophenyl)methoxy]benzoic acid | C22 H18 Cl N O6 | 445 | [M + NH$_4$] |
| 89 | 2-[(3-Benzoylphenyl)methoxy]-3-[(2-chlorophenyl)methoxy]benzoic acid | C28 H21 Cl O5 | 490 | [M + NH$_4$] |
| 90 | 3-[(2-Chlorophenyl)methoxy]-2-[(3,5-dibromophenyl)methoxy]benzoic acid | C21 H15 Br2 Cl O4 | 544 | [M + NH$_4$] |
| 91 | 3-[(2-Chlorophenyl)methoxy]-2-[(2-methoxyphenyl)methoxy]benzoic acid | C22 H19 Cl O5 | 416 | [M + NH$_4$] |
| 92 | 3-[(2-Chlorophenyl)methoxy]-2-[(3,5-dichlorophenyl)methoxy]benzoic acid | C21 H15 Cl3 O4 | 454 | [M + NH$_4$] |
| 93 | 3-[(2-Chlorophenyl)methoxy]-2-[[2-fluoro-5-(trifluoromethyl)phenyl]methoxy]benzoic acid | C22 H15 Cl F4 O4 | 472 | [M + NH$_4$] |
| 94 | 3-[(2-Chlorophenyl)methoxy]-2-[[3-fluoro-5-(trifluoromethyl)phenyl]methoxy]benzoic acid | C22 H15 Cl F4 O4 | 472 | [M + NH$_4$] |
| 95 | 3-[(2-Chlorophenyl)methoxy]-2-[[4-fluoro-2-(trifluoromethyl)phenyl]methoxy]benzoic acid | C22 H15 Cl F4 O4 | 472 | [M + NH$_4$] |
| 96 | 3-[(2-Chlorophenyl)methoxy]-2-[[4-fluoro-3-(trifluoromethyl)phenyl]methoxy]benzoic acid | C22 H15 Cl F4 O4 | 472 | [M + NH$_4$] |
| 97 | 3-[(2-Chlorophenyl)methoxy]-2-[(2,3,6-trifluorophenyl)methoxy]benzoic acid | C21 H14 Cl F3 O4 | 440 | [M + NH$_4$] |
| 98 | 3-[(2-Chlorophenyl)methoxy]-2-[(2,4,5-trifluorophenyl)methoxy]benzoic acid | C21 H14 Cl F3 O4 | 440 | [M + NH$_4$] |
| 99 | 3-[(2-Chlorophenyl)methoxy]-2-[(2,4,6-trifluorophenyl)methoxy]benzoic acid | C21 H14 Cl F3 O4 | 440 | [M + NH$_4$] |
| 100 | 3-[(2-Chlorophenyl)methoxy]-2-[[4-(trifluoromethoxy)phenyl]methoxy]benzoic acid | C22 H16 Cl F3 O5 | 470 | [M + NH$_4$] |
| 101 | 3-[(2-Chlorophenyl)methoxy]-2-[[3-(trifluoromethoxy)phenyl]methoxy]benzoic acid | C22 H16 Cl F3 O5 | 470 | [M + NH$_4$] |
| 102 | 3-[(2-Chlorophenyl)methoxy]-2-[(3,5-dimethoxyphenyl)methoxy]benzoic acid | C23 H21 Cl O6 | 446 | [M + NH$_4$] |
| 103 | 2-([1,1'-Biphenyl]-2-ylmethoxy)-3-[(2-chlorophenyl)methoxy]benzoic acid | C27 H21 Cl O4 | 462 | [M + NH$_4$] |
| 104 | 3-[(2-Chlorophenyl)methoxy]-2-[[4-(methylsulfonyl)phenyl]methoxy]benzoic acid | C22 H19 Cl O6 S | 464 | [M + NH$_4$] |
| 105 | 3-[(2-Chlorophenyl)methoxy]-2-[(4,5-dimethoxy-2-nitrophenyl)methoxy]benzoic acid | C23 H20 Cl N O8 | 491 | [M + NH$_4$] |
| 106 | 3-[(2-Chlorophenyl)methoxy]-2-[(4-iodophenyl)methoxy]benzoic acid | C21 H16 Cl I O4 | 512 | [M + NH$_4$] |

-continued

| Ex. | CAS Name | Elemental formula | Mass Spec. m/z | ion type inferred |
|---|---|---|---|---|
| 107 | 2-[(2-Bromophenyl)methoxy]-3-[(2,4-dichlorophenyl)methoxy]benzoic acid | C21 H15 Br Cl2 O4 | 499 | [M + NH4] |
| 108 | 3-[(2,4-Dichlorophenyl)methoxy]-2-[(2-methylphenyl)methoxy]benzoic acid | C22 H18 Cl2 O4 | 453 | [M + NH4] |
| 109 | 3-[(2,4-Dichlorophenyl)methoxy]-2-[(3-methylphenyl)methoxy]benzoic acid | C22 H18 Cl2 O4 | 434 | [M + NH4] |
| 110 | 2-[(4-Bromophenyl)methoxy]-3-[(2,4-dichlorophenyl)methoxy]benzoic acid | C21 H15 Br Cl2 O4 | 498 | [M + NH4] |
| 111 | 3-[(2,4-Dichlorophenyl)methoxy]-2-[[4-(1,1-dimethylethyl)phenyl]methoxy]benzoic acid | C25 H24 Cl2 O4 | 476 | [M + NH4] |
| 112 | 3-[(2,4-Dichlorophenyl)methoxy]-2-[(4-methylphenyl)methoxy]benzoic acid | C22 H18 Cl2 O4 | 434 | [M + NH4] |
| 113 | 3-[(2,4-Dichlorophenyl)methoxy]-2-[(2-fluorophenyl)methoxy]benzoic acid | C21 H15 Cl2 F O4 | 438 | [M + NH4] |
| 114 | 3-[(2,4-Dichlorophenyl)methoxy]-2-[(2,6-difluorophenyl)methoxy]benzoic acid | C21 H14 Cl2 F2 O4 | 456 | [M + NH4] |
| 115 | 3-[(2,4-Dichlorophenyl)methoxy]-2-[(3-fluorophenyl)methoxy]benzoic acid | C21 H15 Cl2 F O4 | 438 | [M + NH4] |
| 116 | 3-[(2,4-Dichlorophenyl)methoxy]-2-[(4-fluorophenyl)methoxy]benzoic acid | C21 H15 Cl2 F O4 | 438 | [M + NH4] |
| 117 | 3-[(2,4-Dichlorophenyl)methoxy]-2-[[3-(trifluoromethyl)phenyl]methoxy]benzoic acid | C22 H15 Cl2 F3 O4 | 488 | [M + NH4] |
| 118 | 3-[(2,4-Dichlorophenyl)methoxy]-2-[[4-(trifluoromethyl)phenyl]methoxy]benzoic acid | C22 H15 Cl2 F3 O4 | 488 | [M + NH4] |
| 119 | 2-[(2,6-Dichlorophenyl)methoxy]-3-[(2,4-dichlorophenyl)methoxy]benzoic acid | C21 H14 Cl4 O4 | 488 | [M + NH4] |
| 120 | 2-[(3-Chlorophenyl)methoxy]-3-[(2,4-dichlorophenyl)methoxy]benzoic acid | C21 H15 Cl3 O4 | 454 | [M + NH4] |
| 121 | 2-[(2-Chlorophenyl)methoxy]-3-[(2,4-dichlorophenyl)methoxy]benzoic acid | C21 H15 Cl3 O4 | 454 | [M + NH4] |
| 122 | 2-[(2-Chloro-6-fluorophenyl)methoxy]-3-[(2,4-dichlorophenyl)methoxy]benzoic acid | C21 H14 Cl3 F O4 | 472 | [M + NH4] |
| 123 | 3-[(2,4-Dichlorophenyl)methoxy]-2-[(2,5-dimethylphenyl)methoxy]benzoic acid | C23 H20 Cl2 O4 | 448 | [M + NH4] |
| 124 | 2-[(3,4-Dichlorophenyl)methoxy]-3-[(2,4-dichlorophenyl)methoxy]benzoic acid | C21 H14 Cl4 O4 | 488 | [M + NH4] |
| 125 | 2-([1,1'-Biphenyl]-4-ylmethoxy)-3-[(2,4-dichlorophenyl)methoxy]benzoic acid | C27 H20 Cl2 O4 | 496 | [M + NH4] |
| 126 | 2-[(2-Cyanophenyl)methoxy]-3-[(2,4-dichlorophenyl)methoxy]benzoic acid | C22 H15 Cl2 N O4 | 445 | [M + NH4] |
| 127 | 3-[(2,4-Dichlorophenyl)methoxy]-2-(1-naphthalenylmethoxy)benzoic acid | C25 H18 Cl2 O4 | 470 | [M + NH4] |
| 128 | 3-[(2,4-Dichlorophenyl)methoxy]-2-[(2-methyl-1-naphthalenyl)methoxy]benzoic acid | C26 H20 Cl2 O4 | 484 | [M + NH4] |
| 129 | 3-[(2,4-Dichlorophenyl)methoxy]-2-(2-naphthalenylmethoxy)benzoic acid | C25 H18 Cl2 O4 | 470 | [M + NH4] |
| 130 | 2-[(6-Chloro-1,3-benzodioxol-5-yl)methoxy]-3-[(2,4-dichlorophenyl)methoxy]benzoic acid | C22 H15 Cl3 O6 | 498 | [M + NH4] |

-continued

| Ex. | CAS Name | Elemental formula | Mass Spec. m/z | ion type inferred |
|---|---|---|---|---|
| 131 | 3-[(2,4-Dichlorophenyl)methoxy]-2-[(2-methyl-3-nitrophenyl)methoxy]benzoic acid | C22 H17 Cl2 N O6 | 479 | [M + NH$_4$] |
| 132 | 3-[(2,4-Dichlorophenyl)methoxy]-2-[(3-nitrophenyl)methoxy]benzoic acid | C21 H15 Cl2 N O6 | 465 | [M + NH$_4$] |
| 133 | 3-[(2,4-Dichlorophenyl)methoxy]-2-[(2-methoxy-5-nitrophenyl)methoxy]benzoic acid | C22 H17 Cl2 N O7 | 495 | [M + NH$_4$] |
| 134 | 3-[(2,4-Dichlorophenyl)methoxy]-2-[[2-[(phenylsulfonyl)methyl]phenyl]methoxy]benzoic acid | C28 H22 Cl2 O6 S | 574 | [M + NH$_4$] |
| 135 | 3-[(2,4-Dichlorophenyl)methoxy]-2-[(3,4-difluorophenyl)methoxy]benzoic acid | C21 H14 Cl2 F2 O4 | 456 | [M + NH$_4$] |
| 136 | 3-[(2,4-Dichlorophenyl)methoxy]-2-[(2,5-difluorophenyl)methoxy]benzoic acid | C21 H14 Cl2 F2 O4 | 456 | [M + NH$_4$] |
| 137 | 2-[[3,5-Bis(trifluoromethyl)phenyl]methoxy]-3-[(2,4-dichlorophenyl)methoxy]benzoic acid | C23 H14 Cl2 F6 O4 | 556 | [M + NH$_4$] |
| 138 | 3-[(2,4-Dichlorophenyl)methoxy]-2-[(3,5-difluorophenyl)methoxy]benzoic acid | C21 H14 Cl2 F2 O4 | 456 | [M + NH$_4$] |
| 139 | 3-[(2,4-Dichlorophenyl)methoxy]-2-[(2,4-difluorophenyl)methoxy]benzoic acid | C21 H14 Cl2 F2 O4 | 456 | [M + NH$_4$] |
| 140 | 3-[(2,4-Dichlorophenyl)methoxy]-2-[(3,5-dimethylphenyl)methoxy]benzoic acid | C23 H20 Cl2 O4 | 448 | [M + NH$_4$] |
| 141 | 3-[(2,4-Dichlorophenyl)methoxy]-2-[[2-(trifluoromethyl)phenyl]methoxy]benzoic acid | C22 H15 Cl2 F3 O4 | 488 | [M + NH$_4$] |
| 142 | 3-[(2,4-Dichlorophenyl)methoxy]-2-[(2,4-dimethylphenyl)methoxy]benzoic acid | C23 H20 Cl2 O4 | 448 | [M + NH$_4$] |
| 143 | 3-[(2,4-Dichlorophenyl)methoxy]-2-[(3-iodophenyl)methoxy]benzoic acid | C21 H15 Cl2 I O4 | 546 | [M + NH$_4$] |
| 144 | 2-[(2,3-Dichlorophenyl)methoxy]-3-[(2,4-dichlorophenyl)methoxy]benzoic acid | C21 H14 Cl4 O4 | 488 | [M + NH$_4$] |
| 145 | 2-[(2,5-Dichlorophenyl)methoxy]-3-[(2,4-dichlorophenyl)methoxy]benzoic acid | C21 H14 Cl4 O4 | 488 | [M + NH$_4$] |
| 146 | 3-[(2,4-Dichlorophenyl)methoxy]-2-[(4-ethylphenyl)methoxy]benzoic acid | C23 H20 Cl2 O4 | 448 | [M + NH$_4$] |
| 147 | 2-[(4-Chlorophenyl)methoxy]-3-[(2,4-dichlorophenyl)methoxy]benzoic acid | C21 H15 Cl3 O4 | 454 | [M + NH$_4$] |
| 148 | 2-[(3-Bromophenyl)methoxy]-3-[(2,4-dichlorophenyl)methoxy]benzoic acid | C21 H15 Br Cl2 O4 | 498 | [M + NH$_4$] |
| 149 | 3-[(2,4-Dichlorophenyl)methoxy]-2-[(3-phenoxyphenyl)methoxy]benzoic acid | C27 H20 Cl2 O5 | 512 | [M + NH$_4$] |
| 150 | 3-[(2,4-Dichlorophenyl)methoxy]-2-[(2-fluoro-3-methylphenyl)methoxy]benzoic acid | C22 H17 Cl2 F O4 | 452 | [M + NH$_4$] |
| 151 | 3-[(2,4-Dichlorophenyl)methoxy]-2-[(2,3-difluorophenyl)methoxy]benzoic acid | C21 H14 Cl2 F2 O4 | 456 | [M + NH$_4$] |
| 152 | 2-[(3-Chloro-2-fluorophenyl)methoxy]-3-[(2,4-dichlorophenyl)methoxy]benzoic acid | C21 H14 Cl3 F O4 | 472 | [M + NH$_4$] |
| 153 | 3-[(2,4-Dichlorophenyl)methoxy]-2-[(4-methyl-3-nitrophenyl)methoxy]benzoic acid | C22 H17 Cl2 N O6 | 479 | [M + NH$_4$] |
| 154 | 2-[(3-Benzoylphenyl)methoxy]-3-[(2,4-dichlorophenyl)methoxy]benzoic acid | C28 H20 Cl2 O5 | 524 | [M + NH$_4$] |

-continued

| Ex. | CAS Name | Elemental formula | Mass Spec. m/z | ion type inferred |
|---|---|---|---|---|
| 155 | 2-[(3,5-Dibromophenyl)methoxy]-3-[(2,4-dichlorophenyl)methoxy]benzoic acid | C21 H14 Br2 Cl2 O4 | 576 | [M + NH$_4$] |
| 156 | 2-[(6-Chloro-4H-1,3-benzodioxin-8-yl)methoxy]-3-[(2,4-dichlorophenyl)methoxy]benzoic acid | C23 H17 Cl3 O6 | 512 | [M + NH$_4$] |
| 157 | 2-[(3,5-Dichlorophenyl)methoxy]-3-[(2,4-dichlorophenyl)methoxy]benzoic acid | C21 H14 Cl4 O4 | 488 | [M + NH$_4$] |
| 158 | 3-[(2,4-Dichlorophenyl)methoxy]-2-[[2-fluoro-5-(trifluoromethyl)phenyl]methoxy]benzoic acid | C22 H14 Cl2 F4 O4 | 506 | [M + NH$_4$] |
| 159 | 3-[(2,4-Dichlorophenyl)methoxy]-2-[[3-fluoro-5-(trifluoromethyl)phenyl]methoxy]benzoic acid | C22 H14 Cl2 F4 O4 | 506 | [M + NH$_4$] |
| 160 | 3-[(2,4-Dichlorophenyl)methoxy]-2-[[4-fluoro-2-(trifluoromethyl)phenyl]methoxy]benzoic acid | C22 H14 Cl2 F4 O4 | 506 | [M + NH$_4$] |
| 161 | 3-[(2,4-Dichlorophenyl)methoxy]-2-[[4-fluoro-3-(trifluoromethyl)phenyl]methoxy]benzoic acid | C22 H14 Cl2 F4 O4 | 506 | [M + NH$_4$] |
| 162 | 3-[(2,4-Dichlorophenyl)methoxy]-2-[(2,3,6-trifluorophenyl)methoxy]benzoic acid | C21 H13 Cl2 F3 O4 | 474 | [M + NH$_4$] |
| 163 | 3-[(2,4-Dichlorophenyl)methoxy]-2-[(2,4,5-trifluorophenyl)methoxy]benzoic acid | C21 H13 Cl2 F3 O4 | 474 | [M + NH$_4$] |
| 164 | 3-[(2,4-Dichlorophenyl)methoxy]-2-[(2,4,6-trifluorophenyl)methoxy]benzoic acid | C21 H13 Cl2 F3 O4 | 474 | [M + NH$_4$] |
| 165 | 3-[(2,4-Dichlorophenyl)methoxy]-2-[[4-(trifluoromethoxy)phenyl]methoxy]benzoic acid | C22 H15 Cl2 F3 O5 | 504 | [M + NH$_4$] |
| 166 | 3-[(2,4-Dichlorophenyl)methoxy]-2-[[3-(trifluoromethoxy)phenyl]methoxy]benzoic acid | C22 H15 Cl2 F3 O5 | 504 | [M + NH$_4$] |
| 167 | 3-[(2,4-Dichlorophenyl)methoxy]-2-[(3,5-dimethoxyphenyl)methoxy]benzoic acid | C23 H20 Cl2 O6 | 480 | [M + NH$_4$] |
| 168 | 2-([1,1'-Biphenyl]-2-ylmethoxy)-3-[(2,4-dichlorophenyl)methoxy]benzoic acid | C27 H20 Cl2 O4 | 496 | [M + NH$_4$] |
| 169 | 3-[(2,4-Dichlorophenyl)methoxy]-2-[[4-(methylsulfonyl)phenyl]methoxy]benzoic acid | C22 H18 Cl2 O6 S | 498 | [M + NH$_4$] |
| 170 | 3-[(2,4-Dichlorophenyl)methoxy]-2-[(4-iodophenyl)methoxy]benzoic acid | C21 H15 Cl2 I O4 | 546 | [M + NH$_4$] |
| 171 | 3-[(2,4-Dichlorophenyl)methoxy]-2-[(3-methoxyphenyl)methoxy]benzoic acid | C22 H18 Cl2 O5 | 450 | [M + NH$_4$] |
| 172 | 3-[(2-Bromophenyl)methoxy]-2-(1-phenylethoxy)benzoic acid | C22 H19 Br O4 | 444 | [M + NH$_4$] |
| 173 | 2,3-Bis[(2-bromophenyl)methoxy]benzoic acid | C21 H16 Br2 O4 | 508 | [M + NH$_4$] |
| 174 | 3-[(2-Bromophenyl)methoxy]-2-[(2-methylphenyl)methoxy]benzoic acid | C22 H19 Br O4 | 444 | [M + NH$_4$] |
| 175 | 3-[(2-Bromophenyl)methoxy]-2-[(3-methylphenyl)methoxy]benzoic acid | C22 H19 Br O4 | 444 | [M + NH$_4$] |
| 176 | 2-[(4-Bromophenyl)methoxy]-3-[(2-bromophenyl)methoxy]benzoic acid | C21 H16 Br2 O4 | 508 | [M + NH$_4$] |
| 177 | 3-[(2-Bromophenyl)methoxy]-2-[[4-(1,1-dimethylethyl)phenyl]methoxy]benzoic acid | C25 H25 Br O4 | 486 | [M + NH$_4$] |
| 178 | 3-[(2-Bromophenyl)methoxy]-2-[(4-methylphenyl)methoxy]benzoic acid | C22 H19 Br O4 | 444 | [M + NH$_4$] |
| 179 | 3-[(2-Bromophenyl)methoxy]-2-[(2-fluorophenyl)methoxy]benzoic acid | C21 H16 Br F O4 | 448 | [M + NH$_4$] |
| 180 | 3-[(2-Bromophenyl)methoxy]-2-[(2,6-difluorophenyl)methoxy]benzoic acid | C21 H15 Br F2 O4 | 466 | [M + NH$_4$] |

-continued

| Ex. | CAS Name | Elemental formula | Mass Spec. m/z | ion type inferred |
|---|---|---|---|---|
| 181 | 3-[(2-Bromophenyl)methoxy]-2-[(4-fluorophenyl)methoxy]benzoic acid | C21 H16 Br F O4 | 448 | [M + NH4] |
| 182 | 3-[(2-Bromophenyl)methoxy]-2-[[4-(trifluoromethyl)phenyl]methoxy]benzoic acid | C22 H16 Br F3 O4 | 498 | [M + NH4] |
| 183 | 3-[(2-Bromophenyl)methoxy]-2-[(2,6-dichlorophenyl)methoxy]benzoic acid | C21 H15 Br Cl2 O4 | 498 | [M + NH4] |
| 184 | 3-[(2-Bromophenyl)methoxy]-2-[(3-chlorophenyl)methoxy]benzoic acid | C21 H16 Br Cl O4 | 464 | [M + NH4] |
| 185 | 3-[(2-Bromophenyl)methoxy]-2-[(2-chlorophenyl)methoxy]benzoic acid | C21 H16 Br Cl O4 | 464 | [M + NH4] |
| 186 | 3-[(2-Bromophenyl)methoxy]-2-[(2,4-dichlorophenyl)methoxy]benzoic acid | C21 H15 Br Cl2 O4 | 498 | [M + NH4] |
| 187 | 3-[(2-Bromophenyl)methoxy]-2-[(2-chloro-6-fluorophenyl)methoxy]benzoic acid | C21 H15 Br Cl F O4 | 482 | [M + NH4] |
| 188 | 3-[(2-Bromophenyl)methoxy]-2-[(2-iodophenyl)methoxy]benzoic acid | C21 H16 Br I O4 | 556 | [M + NH4] |
| 189 | 3-[(2-Bromophenyl)methoxy]-2-[(2,4,6-trimethylphenyl)methoxy]benzoic acid | C24 H23 Br O4 | 472 | [M + NH4] |
| 190 | 3-[(2-Bromophenyl)methoxy]-2-[(2,5-dimethylphenyl)methoxy]benzoic acid | C23 H21 Br O4 | 458 | [M + NH4] |
| 191 | 3-[(2-Bromophenyl)methoxy]-2-[(3,4-dichlorophenyl)methoxy]benzoic acid | C21 H15 Br Cl2 O4 | 498 | [M + NH4] |
| 192 | 2-([1,1'-Biphenyl]-4-ylmethoxy)-3-[(2-bromophenyl)methoxy]benzoic acid | C27 H21 Br O4 | 506 | [M + NH4] |
| 193 | 3-[(2-Bromophenyl)methoxy]-2-(1-naphthalenylmethoxy)benzoic acid | C25 H19 Br O4 | 480 | [M + NH4] |
| 194 | 3-[(2-Bromophenyl)methoxy]-2-(2-naphthalenylmethoxy)benzoic acid | C25 H19 Br O4 | 480 | [M + NH4] |
| 195 | 2-[[3,4-Bis(phenylmethoxy)phenyl]methoxy]-3-[(2-bromophenyl)methoxy]benzoic acid | C35 H29 Br O6 | 642 | [M + NH4] |
| 196 | 3-[(2-Bromophenyl)methoxy]-2-[(6-chloro-1,3-benzodioxol-5-yl)methoxy]benzoic acid | C22 H16 Br Cl O6 | 508 | [M + NH4] |
| 197 | 3-[(2-Bromophenyl)methoxy]-2-[(3-nitrophenyl)methoxy]benzoic acid | C21 H16 Br N O6 | 475 | [M + NH4] |
| 198 | 3-[(2-Bromophenyl)methoxy]-2-[(2-methoxy-5-nitrophenyl)methoxy]benzoic acid | C22 H18 Br N O7 | 505 | [M + NH4] |
| 199 | 3-[(2-Bromophenyl)methoxy]-2-[(3,4-difluorophenyl)methoxy]benzoic acid | C21 H15 Br F2 O4 | 466 | [M + NH4] |
| 200 | 3-[(2-Bromophenyl)methoxy]-2-[(2,5-difluorophenyl)methoxy]benzoic acid | C21 H15 Br F2 O4 | 466 | [M + NH4] |
| 201 | 2-[[3,5-Bis(trifluoromethyl)phenyl]methoxy]-3-[(2-bromophenyl)methoxy]benzoic acid | C23 H15 Br F6 O4 | 566 | [M + NH4] |
| 202 | 3-[(2-Bromophenyl)methoxy]-2-[(3,5-difluorophenyl)methoxy]benzoic acid | C21 H15 Br F2 O4 | 466 | [M + NH4] |
| 203 | 3-[(2-Bromophenyl)methoxy]-2-[(3,5-dimethylphenyl)methoxy]benzoic acid | C23 H21 Br O4 | 446 | [M + NH4] |
| 204 | 3-[(2-Bromophenyl)methoxy]-2-[[2-(trifluoromethyl)phenyl]methoxy]benzoic acid | C22 H16 Br F3 O4 | 498 | [M + NH4] |

-continued

| Ex. | CAS Name | Elemental formula | Mass Spec. m/z | ion type inferred |
|---|---|---|---|---|
| 205 | 3-[(2-Bromophenyl)methoxy]-2-[(3-iodophenyl)methoxy]benzoic acid | C21 H16 Br I O4 | 556 | [M + NH$_4$] |
| 206 | 3-[(2-Bromophenyl)methoxy]-2-[(2,3-dichlorophenyl)methoxy]benzoic acid | C21 H15 Br Cl2 O4 | 498 | [M + NH$_4$] |
| 207 | 3-[(2-Bromophenyl)methoxy]-2-[(2,5-dichlorophenyl)methoxy]benzoic acid | C21 H15 Br Cl2 O4 | 498 | [M + NH$_4$] |
| 208 | 3-[(2-Bromophenyl)methoxy]-2-[(4-ethylphenyl)methoxy]benzoic acid | C23 H21 Br O4 | 458 | [M + NH$_4$] |
| 209 | 3-[(2-Bromophenyl)methoxy]-2-[(4-chlorophenyl)methoxy]benzoic acid | C21 H16 Br Cl O4 | 464 | [M + NH$_4$] |
| 210 | 2-[(3-Bromophenyl)methoxy]-3-[(2-bromophenyl)methoxy]benzoic acid | C21 H16 Br2 O4 | 508 | [M + NH$_4$] |
| 211 | 3-[(2-Bromophenyl)methoxy]-2-[(3-phenoxyphenyl)methoxy]benzoic acid | C27 H21 Br O5 | 522 | [M + NH$_4$] |
| 212 | 3-[(2-Bromophenyl)methoxy]-2-[(2-fluoro-3-methylphenyl)methoxy]benzoic acid | C22 H18 Br F O4 | 462 | [M + NH$_4$] |
| 213 | 3-[(2-Bromophenyl)methoxy]-2-[(2,3-difluorophenyl)methoxy]benzoic acid | C21 H15 Br F2 O4 | 466 | [M + NH$_4$] |
| 214 | 3-[(2-Bromophenyl)methoxy]-2-[(3-chloro-2-fluorophenyl)methoxy]benzoic acid | C21 H15 Br Cl F O4 | 482 | [M + NH$_4$] |
| 215 | 3-[(2-Bromophenyl)methoxy]-2-[(4-methyl-3-nitrophenyl)methoxy]benzoic acid | C22 H18 Br N O6 | 489 | [M + NH$_4$] |
| 216 | 2-[(3-Benzoylphenyl)methoxy]-3-[(2-bromophenyl)methoxy]benzoic acid | C28 H21 Br O5 | 534 | [M + NH$_4$] |
| 217 | 3-[(2-Bromophenyl)methoxy]-2-[(3,5-dibromophenyl)methoxy]benzoic acid | C21 H15 Br3 O4 | 586 | [M + NH$_4$] |
| 218 | 3-[(2-Bromophenyl)methoxy]-2-[(6-chloro-4H-1,3-benzodioxin-8-yl)methoxy]benzoic acid | C23 H18 Br Cl O6 | 522 | [M + NH$_4$] |
| 219 | 3-[(2-Bromophenyl)methoxy]-2-[[2-fluoro-5-(trifluoromethyl)phenyl]methoxy]benzoic acid | C22 H15 Br F4 O4 | 516 | [M + NH$_4$] |
| 220 | 3-[(2-Bromophenyl)methoxy]-2-[[3-fluoro-5-(trifluoromethyl)phenyl]methoxy]benzoic acid | C22 H15 Br F4 O4 | 516 | [M + NH$_4$] |
| 221 | 3-[(2-Bromophenyl)methoxy]-2-[[4-fluoro-2-(trifluoromethyl)phenyl]methoxy]benzoic acid | C22 H15 Br F4 O4 | 516 | [M + NH$_4$] |
| 222 | 3-[(2-Bromophenyl)methoxy]-2-[[4-fluoro-3-(trifluoromethyl)phenyl]methoxy]benzoic acid | C22 H15 Br F4 O4 | 516 | [M + NH$_4$] |
| 223 | 3-[(2-Bromophenyl)methoxy]-2-[(2,3,6-trifluorophenyl)methoxy]benzoic acid | C21 H14 Br F3 O4 | 484 | [M + NH$_4$] |
| 224 | 3-[(2-Bromophenyl)methoxy]-2-[(2,4,5-trifluorophenyl)methoxy]benzoic acid | C21 H14 Br F3 O4 | 484 | [M + NH$_4$] |
| 225 | 3-[(2-Bromophenyl)methoxy]-2-[(2,4,6-trifluorophenyl)methoxy]benzoic acid | C21 H14 Br F3 O4 | 484 | [M + NH$_4$] |
| 226 | 3-[(2-Bromophenyl)methoxy]-2-[[4-(trifluoromethoxy)phenyl]methoxy]benzoic acid | C22 H16 Br F3 O5 | 514 | [M + NH$_4$] |
| 227 | 3-[(2-Bromophenyl)methoxy]-2-[[3-(trifluoromethoxy)phenyl]methoxy]benzoic acid | C22 H16 Br F3 O5 | 514 | [M + NH$_4$] |
| 228 | 3-[(2-Bromophenyl)methoxy]-2-[(3,5-dimethoxyphenyl)methoxy]benzoic acid | C23 H21 Br O6 | 490 | [M + NH$_4$] |
| 229 | 2-([1,1'-Biphenyl]-2-ylmethoxy)-3-[(2-bromophenyl)methoxy]benzoic acid | C27 H21 Br O4 | 506 | [M + NH$_4$] |

| Ex. | CAS Name | Elemental formula | Mass Spec. m/z | ion type inferred |
|---|---|---|---|---|
| 230 | 3-[(2-Bromophenyl)methoxy]-2-[[4-(methylsulfonyl)phenyl]methoxy]benzoic acid | C22 H19 Br O6 S | 508 | [M + NH₄] |
| 231 | 3-[(2-Bromophenyl)methoxy]-2-[(4-iodophenyl)methoxy]benzoic acid | C21 H16 Br I O4 | 556 | [M + NH₄] |
| 232 | 3-[(2-Bromophenyl)methoxy]-2-[(3-methoxyphenyl)methoxy]benzoic acid | C22 H19 Br O5 | 460 | [M + NH₄] |
| 233 | 3-[(2-Bromophenyl)methoxy]-2-(2-methylpropoxy)benzoic acid | C18 H19 Br O4 | 396 | [M + NH₄] |
| 234 | 3-[(2-Bromophenyl)methoxy]-2-ethoxybenzoic acid | C16 H15 Br O4 | 368 | [M + NH₄] |
| 235 | 3-[(2-Bromophenyl)methoxy]-2-butoxybenzoic acid | C18 H19 Br O4 | 396 | [M + NH₄] |
| 236 | 3-[(2-Bromophenyl)methoxy]-2-(hexyloxy)benzoic acid | C20 H23 Br O4 | 424 | [M + NH₄] |
| 237 | 3-[(2-Bromophenyl)methoxy]-2-(octyloxy)benzoic acid | C22 H27 Br O4 | 452 | [M + NH₄] |
| 238 | 3-[(2-Bromophenyl)methoxy]-2-(cyclohexylmethoxy)benzoic acid | C21 H23 Br O4 | 436 | [M + NH₄] |
| 239 | 3-[(3-Chlorophenyl)methoxy]-2-(phenylmethoxy)benzoic acid | C21 H17 Cl O4 | 386 | [M + NH₄] |
| 240 | 2-[(2-Bromophenyl)methoxy]-3-[(3-chlorophenyl)methoxy]benzoic acid | C21 H16 Br Cl O4 | 464 | [M + NH₄] |
| 241 | 3-[(3-Chlorophenyl)methoxy]-2-[(2-methylphenyl)methoxy]benzoic acid | C22 H19 Cl O4 | 400 | [M + NH₄] |
| 242 | 3-[(3-Chlorophenyl)methoxy]-2-[(3-methylphenyl)methoxy]benzoic acid | C22 H19 Cl O4 | 400 | [M + NH₄] |
| 243 | 2-[(4-Bromophenyl)methoxy]-3-[(3-chlorophenyl)methoxy]benzoic acid | C21 H16 Br Cl O4 | 464 | [M + NH₄] |
| 244 | 3-[(3-Chlorophenyl)methoxy]-2-[[4-(1,1-dimethylethyl)phenyl]methoxy]benzoic acid | C25 H25 Cl O4 | 442 | [M + NH₄] |
| 245 | 3-[(3-Chlorophenyl)methoxy]-2-[(4-methylphenyl)methoxy]benzoic acid | C22 H19 Cl O4 | 400 | [M + NH₄] |
| 246 | 3-[(3-Chlorophenyl)methoxy]-2-[(2-fluorophenyl)methoxy]benzoic acid | C21 H16 Cl F O4 | 404 | [M + NH₄] |
| 247 | 3-[(3-Chlorophenyl)methoxy]-2-[(2,6-difluorophenyl)methoxy]benzoic acid | C21 H15 Cl F2 O4 | 422 | [M + NH₄] |
| 248 | 3-[(3-Chlorophenyl)methoxy]-2-[(3-fluorophenyl)methoxy]benzoic acid | C21 H16 Cl F O4 | 404 | [M + NH₄] |
| 249 | 3-[(3-Chlorophenyl)methoxy]-2-[(4-fluorophenyl)methoxy]benzoic acid | C21 H16 Cl F O4 | 404 | [M + NH₄] |
| 250 | 3-[(3-Chlorophenyl)methoxy]-2-[[3-(trifluoromethyl)phenyl]methoxy]benzoic acid | C22 H16 Cl F3 O4 | 454 | [M + NH₄] |
| 251 | 3-[(3-Chlorophenyl)methoxy]-2-[[4-(trifluoromethyl)phenyl]methoxy]benzoic acid | C22 H16 Cl F3 O4 | 454 | [M + NH₄] |
| 252 | 3-[(3-Chlorophenyl)methoxy]-2-[(2,6-dichlorophenyl)methoxy]benzoic acid | C21 H15 Cl3 O4 | 454 | [M + NH₄] |
| 253 | 2-[(2-Chlorophenyl)methoxy]-3-[(3-chlorophenyl)methoxy]benzoic acid | C21 H16 Cl2 O4 | 420 | [M + NH₄] |
| 254 | 3-[(3-Chlorophenyl)methoxy]-2-[(2,4-dichlorophenyl)methoxy]benzoic acid | C21 H15 Cl3 O4 | 454 | [M + NH₄] |
| 255 | 2-[(2-Chloro-6-fluorophenyl)methoxy]-3-[(3-chlorophenyl)methoxy]benzoic acid | C21 H15 Cl2 F O4 | 438 | [M + NH₄] |
| 256 | 3-[(3-Chlorophenyl)methoxy]-2-[(2-iodophenyl)methoxy]benzoic acid | C21 H16 Cl I O4 | 512 | [M + NH₄] |

-continued

| Ex. | CAS Name | Elemental formula | Mass Spec. m/z | ion type inferred |
|---|---|---|---|---|
| 257 | 3-[(3-Chlorophenyl)methoxy]-2-[(2,5-dimethylphenyl)methoxy]benzoic acid | C23 H21 Cl O4 | 414 | [M + NH$_4$] |
| 258 | 3-[(3-Chlorophenyl)methoxy]-2-[(3,4-dichlorophenyl)methoxy]benzoic acid | C21 H15 Cl3 O4 | 454 | [M + NH$_4$] |
| 259 | 3-[(3-Chlorophenyl)methoxy]-2-[[4-(phenylmethoxy)phenyl]methoxy]benzoic acid | C28 H23 Cl O5 | 492 | [M + NH$_4$] |
| 260 | 2-([1,1'-Biphenyl]-4-ylmethoxy)-3-[(3-chlorophenyl)methoxy]benzoic acid | C27 H21 Cl O4 | 462 | [M + NH$_4$] |
| 261 | 3-[(3-Chlorophenyl)methoxy]-2-[(2-cyanophenyl)methoxy]benzoic acid | C22 H16 Cl N O4 | 411 | [M + NH$_4$] |
| 262 | 3-[(3-Chlorophenyl)methoxy]-2-(1-naphthalenylmethoxy)benzoic acid | C25 H19 Cl O4 | 436 | [M + NH$_4$] |
| 263 | 3-[(3-Chlorophenyl)methoxy]-2-[(2-methyl-1-naphthalenyl)methoxy]benzoic acid | C26 H21 Cl O4 | 450 | [M + NH$_4$] |
| 264 | 3-[(3-Chlorophenyl)methoxy]-2-(2-naphthalenylmethoxy)benzoic acid | C25 H19 Cl O4 | 436 | [M + NH$_4$] |
| 265 | 2-[(6-Chloro-1,3-benzodioxol-5-yl)methoxy]-3-[(3-chlorophenyl)methoxy]benzoic acid | C22 H16 Cl2 O6 | 464 | [M + NH$_4$] |
| 266 | 3-[(3-Chlorophenyl)methoxy]-2-[(2-methyl-3-nitrophenyl)methoxy]benzoic acid | C22 H18 Cl N O6 | 444 | [M + NH$_4$] |
| 267 | 3-[(3-Chlorophenyl)methoxy]-2-[(3-nitrophenyl)methoxy]benzoic acid | C21 H16 Cl N O6 | 431 | [M + NH$_4$] |
| 268 | 3-[(3-Chlorophenyl)methoxy]-2-[(2-methoxy-5-nitrophenyl)methoxy]benzoic acid | C22 H18 Cl N O7 | 461 | [M + NH$_4$] |
| 269 | 3-[(3-Chlorophenyl)methoxy]-2-[[2-[(phenylsulfonyl)methyl]phenyl]methoxy]benzoic acid | C28 H23 Cl O6 S | 540 | [M + NH$_4$] |
| 270 | 3-[(3-Chlorophenyl)methoxy]-2-[(2,5-difluorophenyl)methoxy]benzoic acid | C21 H15 Cl F2 O4 | 422 | [M + NH$_4$] |
| 271 | 3-[(3-Chlorophenyl)methoxy]-2-[(3,5-difluorophenyl)methoxy]benzoic acid | C21 H15 Cl F2 O4 | 422 | [M + NH$_4$] |
| 272 | 3-[(3-Chlorophenyl)methoxy]-2-[(3,5-dimethylphenyl)methoxy]benzoic acid | C23 H21 Cl O4 | 414 | [M + NH$_4$] |
| 273 | 3-[(3-Chlorophenyl)methoxy]-2-[[2-(trifluoromethyl)phenyl]methoxy]benzoic acid | C22 H16 Cl F3 O4 | 454 | [M + NH$_4$] |
| 274 | 3-[(3-Chlorophenyl)methoxy]-2-[(3-iodophenyl)methoxy]benzoic acid | C21 H16 Cl I O4 | 512 | [M + NH$_4$] |
| 275 | 3-[(3-Chlorophenyl)methoxy]-2-[(2,3-dichlorophenyl)methoxy]benzoic acid | C21 H15 Cl3 O4 | 454 | [M + NH$_4$] |
| 276 | 3-[(3-Chlorophenyl)methoxy]-2-[(2,5-dichlorophenyl)methoxy]benzoic acid | C21 H15 Cl3 O4 | 454 | [M + NH$_4$] |
| 277 | 2-[(4-Chlorophenyl)methoxy]-3-[(3-chlorophenyl)methoxy]benzoic acid | C21 H16 Cl2 O4 | 420 | [M + NH$_4$] |
| 278 | 2-[(3-Bromophenyl)methoxy]-3-[(3-chlorophenyl)methoxy]benzoic acid | C21 H16 Br Cl O4 | 464 | [M + NH$_4$] |
| 279 | 3-[(3-Chlorophenyl)methoxy]-2-[(3-phenoxyphenyl)methoxy]benzoic acid | C27 H21 Cl O5 | 478 | [M + NH$_4$] |
| 280 | 3-[(3-Chlorophenyl)methoxy]-2-[(2-fluoro-3-methylphenyl)methoxy]benzoic acid | C22 H18 Cl F O4 | 418 | [M + NH$_4$] |
| 281 | 3-[(3-Chlorophenyl)methoxy]-2-[(2,3-difluorophenyl)methoxy]benzoic acid | C21 H15 Cl F2 O4 | 422 | [M + NH$_4$] |

-continued

| Ex. | CAS Name | Elemental formula | Mass Spec. m/z | ion type inferred |
|---|---|---|---|---|
| 282 | 2-[(3-Chloro-2-fluorophenyl)methoxy]-3-[(3-chlorophenyl)methoxy]benzoic acid | C21 H15 Cl2 F O4 | 438 | [M + NH$_4$] |
| 283 | 3-[(3-Chlorophenyl)methoxy]-2-[(4-methyl-3-nitrophenyl)methoxy]benzoic acid | C22 H18 Cl N O6 | 444 | [M + NH$_4$] |
| 284 | 2-[(3-Benzoylphenyl)methoxy]-3-[(3-chlorophenyl)methoxy]benzoic acid | C28 H21 Cl O5 | 490 | [M + NH$_4$] |
| 285 | 3-[(3-Chlorophenyl)methoxy]-2-[(3,5-dibromophenyl)methoxy]benzoic acid | C21 H15 Br2 Cl O4 | 542 | [M + NH$_4$] |
| 286 | 2-[(6-Chloro-4H-1,3-benzodioxin-8-yl)methoxy]-3-[(3-chlorophenyl)methoxy]benzoic acid | C23 H18 Cl2 O6 | 478 | [M + NH$_4$] |
| 287 | 3-[(3-Chlorophenyl)methoxy]-2-[(2-methoxyphenyl)methoxy]benzoic acid | C22 H19 Cl O5 | 416 | [M + NH$_4$] |
| 288 | 3-[(3-Chlorophenyl)methoxy]-2-[[2-fluoro-5-(trifluoromethyl)phenyl]methoxy]benzoic acid | C22 H15 Cl F4 O4 | 472 | [M + NH$_4$] |
| 289 | 3-[(3-Chlorophenyl)methoxy]-2-[[3-fluoro-5-(trifluoromethyl)phenyl]methoxy]benzoic acid | C22 H15 Cl F4 O4 | 472 | [M + NH$_4$] |
| 290 | 3-[(3-Chlorophenyl)methoxy]-2-[[4-fluoro-2-(trifluoromethyl)phenyl]methoxy]benzoic acid | C22 H15 Cl F4 O4 | 472 | [M + NH$_4$] |
| 291 | 3-[(3-Chlorophenyl)methoxy]-2-[[4-fluoro-3-(trifluoromethyl)phenyl]methoxy]benzoic acid | C22 H15 Cl F4 O4 | 472 | [M + NH$_4$] |
| 292 | 3-[(3-Chlorophenyl)methoxy]-2-[(2,3,6-trifluorophenyl)methoxy]benzoic acid | C21 H14 Cl F3 O4 | 440 | [M + NH$_4$] |
| 293 | 3-[(3-Chlorophenyl)methoxy]-2-[(2,4,5-trifluorophenyl)methoxy]benzoic acid | C21 H14 Cl F3 O4 | 440 | [M + NH$_4$] |
| 294 | 3-[(3-Chlorophenyl)methoxy]-2-[(2,4,6-trifluorophenyl)methoxy]benzoic acid | C21 H14 Cl F3 O4 | 440 | [M + NH$_4$] |
| 295 | 3-[(3-Chlorophenyl)methoxy]-2-[[4-(trifluoromethoxy)phenyl]methoxy]benzoic acid | C22 H16 Cl F3 O5 | 470 | [M + NH$_4$] |
| 296 | 3-[(3-Chlorophenyl)methoxy]-2-[[3-(trifluoromethoxy)phenyl]methoxy]benzoic acid | C22 H16 Cl F3 O5 | 470 | [M + NH$_4$] |
| 297 | 3-[(3-Chlorophenyl)methoxy]-2-[(3,5-dimethoxyphenyl)methoxy]benzoic acid | C23 H21 Cl O6 | 446 | [M + NH$_4$] |
| 298 | 2-([1,1'-Biphenyl]-2-ylmethoxy)-3-[(3-chlorophenyl)methoxy]benzoic acid | C27 H21 Cl O4 | 462 | [M + NH$_4$] |
| 299 | 3-[(3-Chlorophenyl)methoxy]-2-[[4-(methylsulfonyl)phenyl]methoxy]benzoic acid | C22 H19 Cl O6 S | 464 | [M + NH$_4$] |
| 300 | 3-[(3-Chlorophenyl)methoxy]-2-[(3-methoxyphenyl)methoxy]benzoic acid | C22 H19 Cl O5 | 416 | [M + NH$_4$] |
| 301 | 3-[(3-Chlorophenyl)methoxy]-2-(2-methylpropoxy)benzoic acid | C18 H19 Cl O4 | 352 | [M + NH$_4$] |
| 302 | 2-Butoxy-3-[(3-chlorophenyl)methoxy]benzoic acid | C18 H19 Cl O4 | 352 | [M + NH$_4$] |
| 303 | 3-[(3-Chlorophenyl)methoxy]-2-(hexyloxy)benzoic acid | C20 H23 Cl O4 | 380 | [M + NH$_4$] |
| 304 | 2-[(2-Bromophenyl)methoxy]-3-[(4-chlorophenyl)methoxy]benzoic acid | C21 H16 Br Cl O4 | 464 | [M + NH$_4$] |
| 305 | 2-[(4-Bromophenyl)methoxy]-3-[(4-chlorophenyl)methoxy]benzoic acid | C21 H16 Br Cl O4 | 464 | [M + NH$_4$] |
| 306 | 3-[(4-Chlorophenyl)methoxy]-2-[[4-(1,1-dimethylethyl)phenyl]methoxy]benzoic acid | C25 H25 Cl O4 | 442 | [M + NH$_4$] |
| 307 | 3-[(4-Chlorophenyl)methoxy]-2-[(4-methylphenyl)methoxy]benzoic acid | C22 H19 Cl O4 | 400 | [M + NH$_4$] |

-continued

| Ex. | CAS Name | Elemental formula | Mass Spec. m/z | ion type inferred |
|---|---|---|---|---|
| 308 | 3-[(4-Chlorophenyl)methoxy]-2-[(2-fluorophenyl)methoxy]benzoic acid | C21 H16 Cl F O4 | 404 | [M + NH$_4$] |
| 309 | 3-[(4-Chlorophenyl)methoxy]-2-[(2,6-difluorophenyl)methoxy]benzoic acid | C21 H15 Cl F2 O4 | 422 | [M + NH$_4$] |
| 310 | 3-[(4-Chlorophenyl)methoxy]-2-[(3-fluorophenyl)methoxy]benzoic acid | C21 H16 Cl F O4 | 404 | [M + NH$_4$] |
| 311 | 3-[(4-Chlorophenyl)methoxy]-2-[(4-fluorophenyl)methoxy]benzoic acid | C21 H16 Cl F O4 | 404 | [M + NH$_4$] |
| 312 | 3-[(4-Chlorophenyl)methoxy]-2-[[3-(trifluoromethyl)phenyl]methoxy]benzoic acid | C22 H16 Cl F3 O4 | 454 | [M + NH$_4$] |
| 313 | 3-[(4-Chlorophenyl)methoxy]-2-[[4-(trifluoromethyl)phenyl]methoxy]benzoic acid | C22 H16 Cl F3 O4 | 454 | [M + NH$_4$] |
| 314 | 3-[(4-Chlorophenyl)methoxy]-2-[(2,6-dichlorophenyl)methoxy]benzoic acid | C21 H15 Cl3 O4 | 454 | [M + NH$_4$] |
| 315 | 2-[(3-Chlorophenyl)methoxy]-3-[(4-chlorophenyl)methoxy]benzoic acid | C21 H16 Cl2 O4 | 420 | [M + NH$_4$] |
| 316 | 2-[(2-Chloro-6-fluorophenyl)methoxy]-3-[(4-chlorophenyl)methoxy]benzoic acid | C21 H15 Cl2 F O4 | 438 | [M + NH$_4$] |
| 317 | 3-[(4-Chlorophenyl)methoxy]-2-[(2-iodophenyl)methoxy]benzoic acid | C21 H16 Cl I O4 | 512 | [M + NH$_4$] |
| 318 | 3-[(4-Chlorophenyl)methoxy]-2-[(2,5-dimethylphenyl)methoxy]benzoic acid | C23 H21 Cl O4 | 514 | [M + NH$_4$] |
| 319 | 3-[(4-Chlorophenyl)methoxy]-2-[(3,4-dichlorophenyl)methoxy]benzoic acid | C21 H15 Cl3 O4 | 454 | [M + NH$_4$] |
| 320 | 2-([1,1'-Biphenyl]-4-ylmethoxy)-3-[(4-chlorophenyl)methoxy]benzoic acid | C27 H21 Cl O4 | 462 | [M + NH$_4$] |
| 321 | 3-[(4-Chlorophenyl)methoxy]-2-(1-naphthalenylmethoxy)benzoic acid | C25 H19 Cl O4 | 436 | [M + NH$_4$] |
| 322 | 2-[(2-Chlorophenyl)methoxy]-3-[(4-chlorophenyl)methoxy]benzoic acid | C21 H16 Cl2 O4 | 420 | [M + NH$_4$] |
| 323 | 3-[(4-Chlorophenyl)methoxy]-2-(2-naphthalenylmethoxy)benzoic acid | C25 H19 Cl O4 | 436 | [M + NH$_4$] |
| 324 | 3-[(4-Chlorophenyl)methoxy]-2-[(2-methyl-3-nitrophenyl)methoxy]benzoic acid | C22 H18 Cl N O6 | 445 | [M + NH$_4$] |
| 325 | 3-[(4-Chlorophenyl)methoxy]-2-[(2,5-difluorophenyl)methoxy]benzoic acid | C21 H15 Cl F2 O4 | 422 | [M + NH$_4$] |
| 326 | 2-[[3,5-Bis(trifluoromethyl)phenyl]methoxy]-3-[(4-chlorophenyl)methoxy]benzoic acid | C23 H15 Cl F6 O4 | 522 | [M + NH$_4$] |
| 327 | 3-[(4-Chlorophenyl)methoxy]-2-[[2-(trifluoromethyl)phenyl]methoxy]benzoic acid | C22 H16 Cl F3 O4 | 454 | [M + NH$_4$] |
| 328 | 3-[(4-Chlorophenyl)methoxy]-2-[(2,3-dichlorophenyl)methoxy]benzoic acid | C21 H15 Cl3 O4 | 454 | [M + NH$_4$] |
| 329 | 3-[(4-Chlorophenyl)methoxy]-2-[(2,5-dichlorophenyl)methoxy]benzoic acid | C21 H15 Cl3 O4 | 454 | [M + NH$_4$] |
| 330 | 2-[(6-Chloro-4H-1,3-benzodioxin-8-yl)methoxy]-3-[(4-chlorophenyl)methoxy]benzoic acid | C23 H18 Cl2 O6 | 478 | [M + NH$_4$] |
| 331 | 3-[(4-Chlorophenyl)methoxy]-2-[(2,3,6-trifluorophenyl)methoxy]benzoic acid | C21 H14 Cl F3 O4 | 440 | [M + NH$_4$] |

-continued

| Ex. | CAS Name | Elemental formula | Mass Spec. m/z | ion type inferred |
|---|---|---|---|---|
| 332 | 3-[(4-Chlorophenyl)methoxy]-2-[[3-(trifluoromethoxy)phenyl]methoxy]benzoic acid | C22 H16 Cl F3 O5 | 470 | [M + NH$_4$] |
| 333 | 3-[(4-Chlorophenyl)methoxy]-2-[(3,5-dimethoxyphenyl)methoxy]benzoic acid | C23 H21 Cl O6 | 446 | [M + NH$_4$] |
| 334 | 2-Butoxy-3-[(4-chlorophenyl)methoxy]benzoic acid | C18 H19 Cl O4 | 352 | [M + NH$_4$] |
| 335 | 3-[(4-Chlorophenyl)methoxy]-2-(hexyloxy)benzoic acid | C20 H23 Cl O4 | 380 | [M + NH$_4$] |
| 336 | 3-[(4-Chlorophenyl)methoxy]-2-(cyclohexylmethoxy)benzoic acid | C21 H23 Cl O4 | 392 | [M + NH$_4$] |

EXAMPLE 337

2,3-Bis[(2-chlorophenyl)methoxy]-α-methoxybenzeneacetic acid

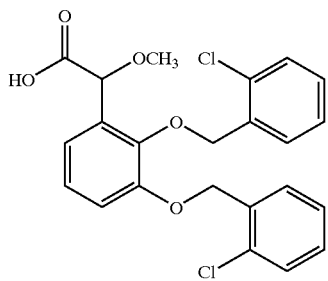

A

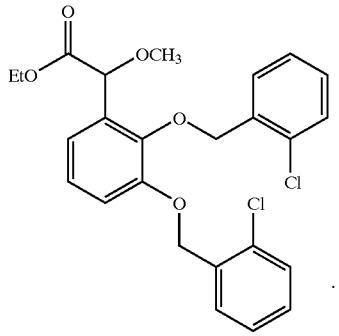

To a stirred solution of Example 1 Part B compound (112 mg, 0.243 mmol) in DME (1 mL) under argon at room temperature was added sodium hydride (60% mineral oil dispersion, 9.7 mg, 0.24 mmol). After 30 min, methyl iodide (15 µL, 0.24 mmol) was added, the reaction mixture was stirred for 18 h and then diluted with saturated ammonium chloride solution. The mixture was extracted three times with Et$_2$O. The organic extracts were combined, washed once with water, once with brine, dried (MgSO$_4$) and evaporated. Purification by flash chromatography on silica gel provided the title compound as a colorless oil, 67 mg (58% yield). LC/MS gave the correct molecular ion [(M+H)$^+$=475] for the desired compound.

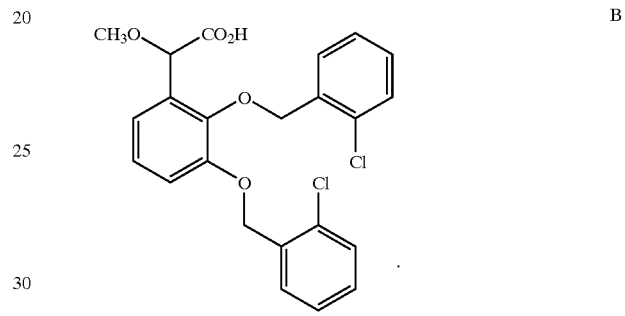

B

To a stirred solution of part A compound (65 mg, 0.14 mmol) in THF (1 mL) at room temperature under argon was added sodium hydroxide solution (1.0 mL, 1 M, 1.0 mmol). After 15 h, the reaction was diluted with water and extracted once with ether. The aqueous phase was brought to pH 2 with 1 M hydrochloric acid and extracted three times with Et$_2$O. The acidified organic extracts were combined, washed with water, brine, dried (Na$_2$SO$_4$) and evaporated to give the title compound as a colorless oil, 49 mg (80% yield). LC/MS gave the correct molecular ion [(M+H)$^+$=447] for the desired compound.

EXAMPLE 338

(E)-2,3-Bis[(2-chlorophenyl)methoxy]-α-(hydroxyimino)benzeneacetic acid and (Z)-2,3-Bis[(2-chlorophenyl)methoxy]-α-(hydroxyimino)benzeneacetic acid

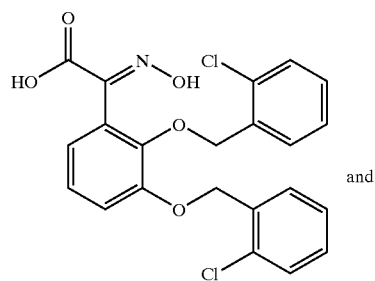

and

-continued

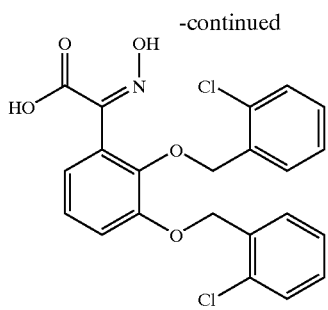

A

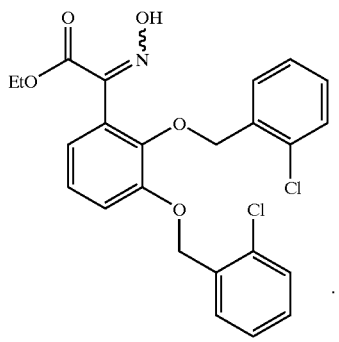

To a stirred solution of Example 26 Part B compound (105 mg, 0.23 mmol) in EtOH (1 mL) under argon at room temperature was added sodium acetate (20.6 mg, 0.25 mmol) and hydroxylamine hydrochloride (17.3 mg, 0.25 mmol). The reaction mixture was heated to reflux for 3 h, cooled, diluted with EtOH and filtered. The filtrate was evaporated and water (5 mL) was added to give a gummy solid. The solid was dissolved in Et$_2$O, washed with water, brine, dried (Na$_2$SO$_4$) and evaporated title compound as a 5:4 mixture of geometric isomers, colorless oil, 100 mg (93% yield). LC/MS gave the correct molecular ion [(M+H)$^+$=474] for the desired compound.

B

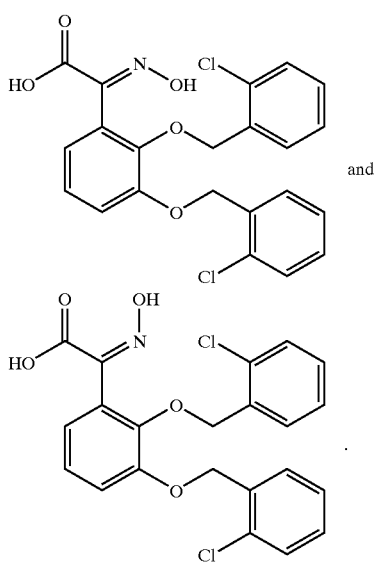

To a stirred solution of part A compound (100 mg, 0.22 mmol) in THF (1 mL) at room temperature under argon was added sodium hydroxide solution (1.0 mL, 1 M, 1.0 mmol). After 15 h, the reaction was diluted with water and extracted once with ether. The aqueous phase was brought to pH 2 with 1 M hydrochloric acid and extracted three times with Et$_2$O. The acidified organic extracts were combined, washed with water, brine, dried (Na$_2$SO$_4$) and evaporated. Purification by reverse phase HPLC (YMC S5 ODS 20×250 mm column, acetonitrile/ water–0.1% TFA gradient) gave the title compounds as separate white amorphous solids, both geometric isomers of the oxime. LC/MS gave the correct molecular ion [(M+H)$^+$=446] for each of the desired compounds.

EXAMPLE 339

(E)-2,3-Bis[(2-chlorophenyl)methoxy]-α-(methoxyimino)benzeneacetic acid and (Z)-2,3-Bis[(2-chlorophenyl)methoxy]-α-(methoxyimino)benzeneacetic acid

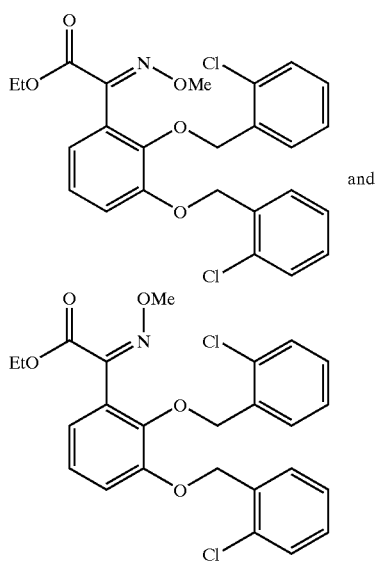

To a stirred solution of Example 26 Part B compound (105 mg, 0.23 mmol) in EtOH (1 mL) under argon at room temperature was added sodium acetate (20.6 mg, 0.25 mmol) and methoxylamine hydrochloride (20.8 mg, 0.25 mmol). The reaction mixture was heated to reflux for 17 h, and additional portions of sodium acetate and methoxylamine hydrochloride were added and the reaction refluxed for an additional 5 h. The mixture was cooled, diluted with EtOH and filtered. The filtrate was evaporated and water (5 mL) was added to give a gummy solid. The solid was dissolved in Et$_2$O, washed with water, brine, dried (Na$_2$SO$_4$) and evaporated. Purification by flash chromatography on silica gel provided the title compounds: Isomer A (first eluting) as colorless oil, 49 mg (44% yield) and Isomer B as a colorless oil, 34 mg, 34%. LC/MS gave the correct molecular ion [(M+H)$^+$=478] for each of the desired compounds.

EXAMPLE 340

(E or Z)-2,3-Bis[(2-chlorophenyl)methoxy]-α-(methoxyimino)benzeneacetic acid

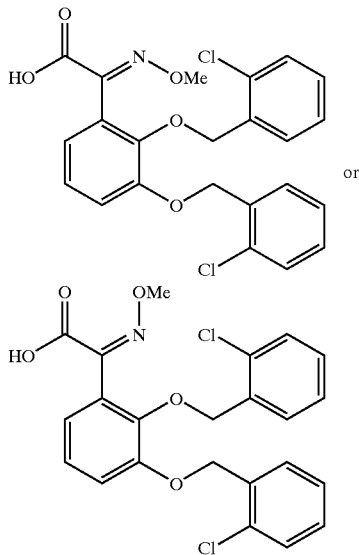

or

To a stirred solution of Example 339 (Isomer A) compound (49 mg, 0.1 mmol) in THF (1 mL) at room temperature under argon was added sodium hydroxide solution (1.0 mL, 1 M, 1.0 mmol). The reaction was heated to 50° C. After 16 h, the reaction was diluted with water and extracted once with ether. The aqueous phase was brought to pH 2 with 1 M hydrochloric acid and extracted three times with Et₂O. The acidified organic extracts were combined, washed with water, brine, dried (Na₂SO₄) and evaporated to provide the title compound as a white solid, 37 mg, (80% yield), mp 140–141° C. LC/MS gave the correct molecular ion [(M+H)⁺=460] for the desired compound.

EXAMPLE 341

(E or Z)-2,3-Bis[(2-chlorophenyl)methoxy]-α-(methoxyimino)benzeneacetic acid

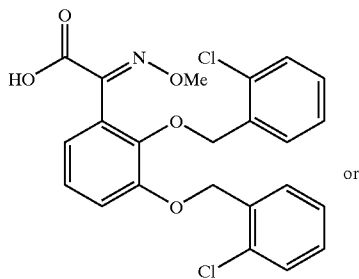

or

-continued

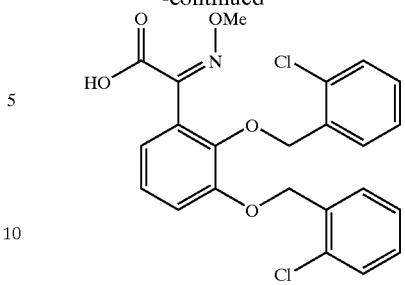

To a stirred solution of Example 339 (Isomer B) compound (37 mg, 0.075 mmol) in THF (1 mL) at room temperature under argon was added sodium hydroxide solution (1.0 mL, 1 M, 1.0 mmol). The reaction was heated to 50° C. After 16 h, the reaction was diluted with water and extracted once with ether. The aqueous phase was brought to pH 2 with 1 M hydrochloric acid and extracted three times with Et₂O. The acidified organic extracts were combined, washed with water, brine, dried (Na₂SO₄) and evaporated to provide the title compound as a white solid, 32 mg, (91% yield), mp 97–99° C. LC/MS gave the correct molecular ion [(M+H)⁺=460] for the desired compound.

EXAMPLE 342

3-[(2-chlorophenyl)methoxy]-2-(cyclohexylmethoxy)-α-hydroxybenzeneacetic acid

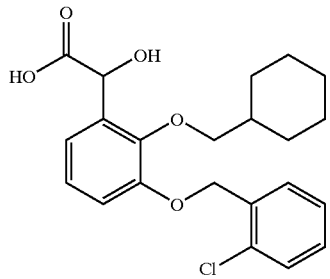

A

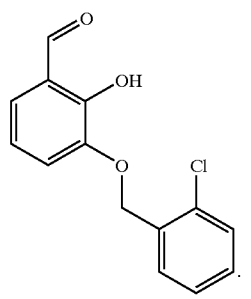

To a stirred slurry of sodium hydride (60% mineral oil dispersion, 3.68 g, 92 mmol) in DMSO (40 mL) at room temperature under argon was added a solution of 2,3-dihydroxybenzaldehyde (5.53 g, 40.0 mmol) in DMSO (20 mL). After 1 h, a solution of 2-chlorobenzylchloride (5.05 mL, 40.0 mmol) in DMSO (10 mL) was added, the reaction mixture was stirred for 60 h and then diluted with water. The mixture was extracted three times with Et₂O. The organic extracts were combined, washed once with water, once with brine, dried (Na₂SO₄) and evaporated. Purification by flash chromatography on silica gel provided the title compound, 5.6 g (53% yield). LC/MS gave the correct molecular ion [(M+H)⁺=263] for the desired compound.

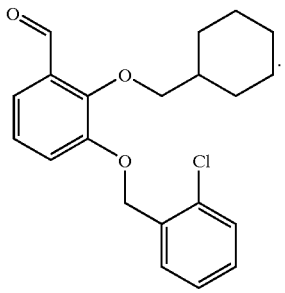

B

To a stirred solution of part A compound (1.31 g, 5.00 mmol) in EtOH (15 mL) at room temperature under argon was added potassium carbonate (1.04 g, 7.5 mmol) and then cyclohexylmethyl bromide (0.98 mL, 7.0 mmol). After 16 h at reflux, the reaction was diluted with water, extracted with CH₂Cl₂, dried (Na₂SO₄) and evaporated. Purification by flash chromatography gave the title compound as a colorless oil, 400 mg (22% yield). LC/MS gave the correct molecular ion [(M+H)⁺=359] for the desired compound.

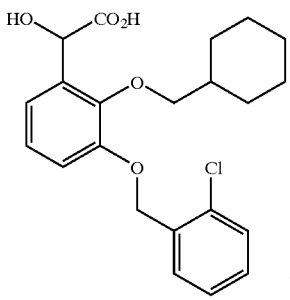

C

By the method of Example 1, Part B compound (340 mg, 0.95 mmol) was converted to the title compound as a white amorphous solid, 170 mg, 47% yield. LC/MS gave the correct molecular ion [(M+H)⁺=405] for the desired compound.

EXAMPLE 343

3-[(2-chlorophenyl)methoxy]-α-hydroxy-2-[(2-methoxyphenyl)methoxy]benzeneacetic acid

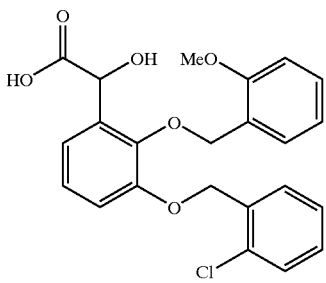

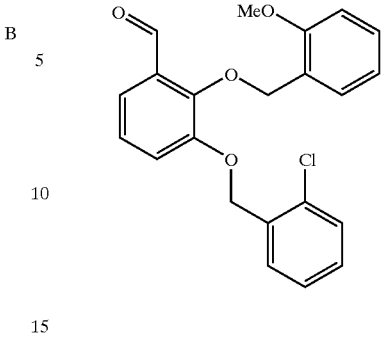

A

By the method of Example 342 Part B, but using 2-methoxybenzyl chloride in place of cyclohexylmethyl bromide, the title compound was prepared. LC/MS gave the correct molecular ion [(M+H)⁺=383] for the desired compound.

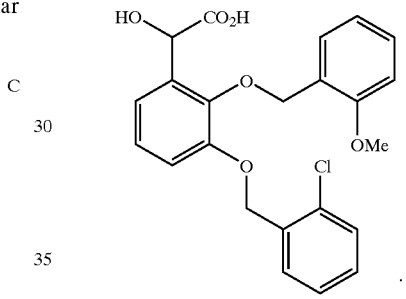

B

By the method of Example 1, Part A compound (110 mg, 0.29 mmol) was converted to the title compound as a white amorphous solid. LC/MS gave the correct molecular ion [(M+H)⁺=429] for the desired compound.

EXAMPLE 344

3-[(2-Chlorophenyl)methoxy]-α-hydroxy-2-(4-pyridinylmethoxy)benzeneacetic acid

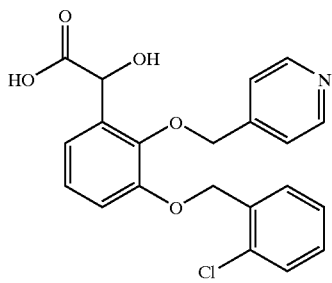

-continued

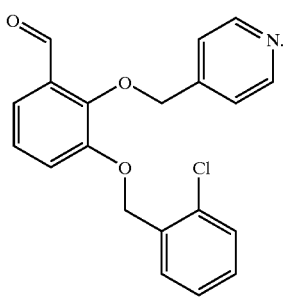

By the method of Example 342 Part B, but using the free base of 4-picolyl chloride in place of cyclohexylmethyl bromide, the title compound was prepared. LC/MS gave the correct molecular ion [(M+H)$^+$=354] for the desired compound.

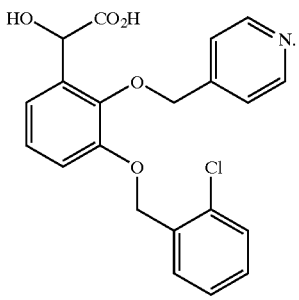

By the method of Example 1, Part A compound (581 mg, 1.54 mmol) was converted to the title compound as a white solid, mp 181–183° C. LC/MS gave the correct molecular ion [(M+H)$^+$=400] for the desired compound.

EXAMPLE 345

2,3-Bis[(3,5-dichlorophenyl)methoxy]benzoic acid

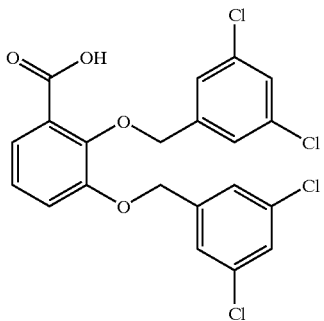

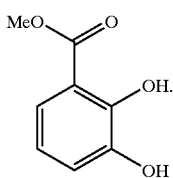

A

A solution of 2,3-dihydroxybenzoic acid (3.00 g, 19.46 mmol) and 96% sulfuric acid (3 mL, 55 mmol) in methanol (60 mL) at room temperature under argon was stirred for 1 h. The reaction mixture was heated to reflux for 16 h, then cooled, concentrated to half the volume and poured into water (150 mL) and ethyl acetate (150 mL). The organic fraction was washed with water, aqueous NaHCO$_3$ solution, dried (MgSO$_4$) and concentrated to give the title compound as a white solid (2.90 g, 89%). mp 77–78° C. LC/MS gave the correct molecular ion [(M–H)$^-$=167] for the desired compound.

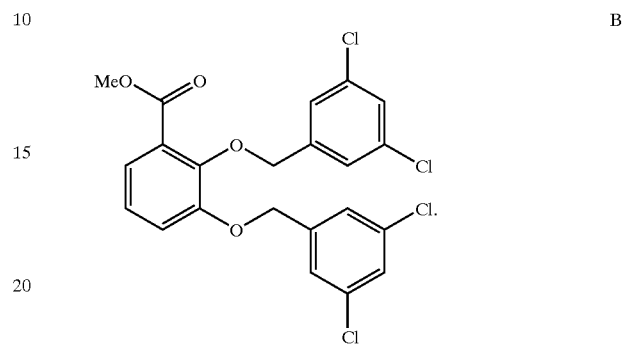

B

To a stirred solution of part A compound (0.17 g, 1.00 mmol) in DMF (13 mL) at room temperature under argon was added K$_2$CO$_3$ (1.10 g, 8.00 mmol), tetrabutylammonium iodide (0.05 g, 0.14 mmol) and 3,5-dichlorobenzyl chloride (0.78 g, 4.00 mmol). The mixture was stirred at RT for 0.5 h and then at 60° C. for 1.5 h. The mixture was cooled, filtered through a pad of Celite and poured into diethyl ether. The ether fraction was washed with brine, dried over MgSO$_4$ and concentrated. The title compound was then crystallized from 1:9 THF/methanol to give the title compound as a white solid (0.25 g, 51%), mp 150–151° C.

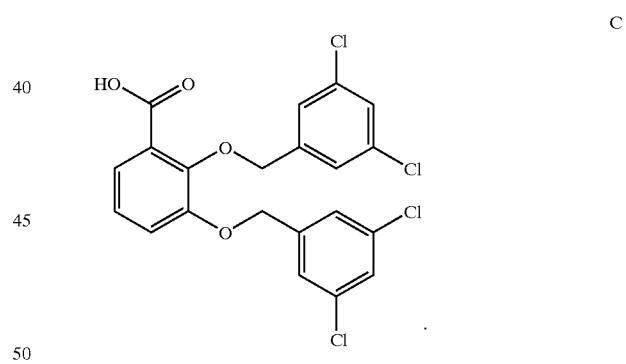

C

A solution of part B compound (0.12 g, 0.25 mmol) in a THF:methanol (3 mL:0.5 mL) solution was stirred at room temperature under argon, as 10 M NaOH solution (0.05 mL, 0.5 mmol) was added. After 4 h, the reaction mixture was concentrated and diluted with water (5 mL). The mixture was acidified to pH=1 with 1N HCl and the white solid collected (0.10 g, 85%). LC/MS gave the correct molecular ion [(M–H)$^-$=471$^-$] for the title compound. mp 219–220° C.

EXAMPLES 346–352

The following compounds were prepared according to the methods outlined in Example A, utilizing 2,4-dichlorobenzyl chloride, 2-chlorobenzyl chloride, 3-chlorobenzyl chloride, 4-chlorobenzyl chloride, 3,5-bis(trifluoromethyl)benzyl chloride, 2,5-dimethylbenzyl chloride, and 3,5-dimethylbenzyl chloride.

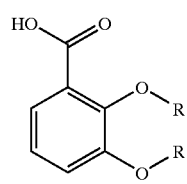

| Ex. | R | m.p. (° C.) | m/z (−ions) | Name |
|---|---|---|---|---|
| 346 | 2,4-dichlorobenzyl | 168–169 | M-H 471⁻ | 2,3-Bis[(2,4-dichlorophenyl)methoxy]benzoic acid |
| 347 | 2-chlorobenzyl | 156–157 | M-H 401⁻ | 2,3-Bis[(2-chlorophenyl)methoxy]benzoic acid |
| 348 | 3-chlorobenzyl | 126–127 | M-H 401⁻ | 2,3-Bis[(3-chlorophenyl)methoxy]benzoic acid |
| 349 | 4-chlorobenzyl | 174–175 | M-H 401⁻ | 2,3-Bis[(4-chlorophenyl)methoxy]benzoic acid |
| 350 | 3,5-bis(trifluoromethyl)benzyl | 156–158 | M-H 605⁻ | 2,3-Bis[[3,5-bis(trifluoromethyl)phenyl]methoxy]benzoic acid |
| 351 | 2,5-dimethylbenzyl | 114–116 | M-H 389⁻ | 2,3-Bis[(2,5-dimethylphenyl)methoxy]benzoic acid |
| 352 | 3,5-dimethylbenzyl | 117–118 | M-H 389⁻ | 2,3-Bis[(3,5-dimethylphenyl)methoxy]benzoic acid |

EXAMPLE 353

2-[(2,4-Dichlorophenyl)methoxy]-3-(phenylmethoxy)benzoic acid

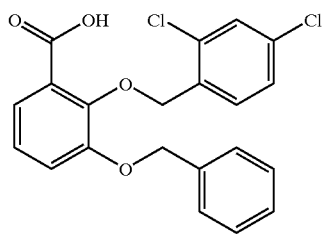

A

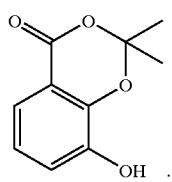

For preparation of part A compound, see example 25 part A.

B

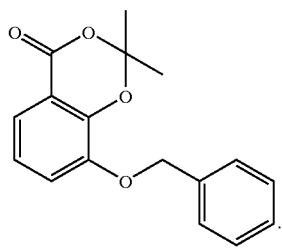

To a stirred solution of part A compound (0.19 g, 1.00 mmol) in DMF (5 mL) at room temperature under argon was added $K_2CO_3$ (0.27 g, 2.00 mmol) and benzyl bromide (0.14 mL, 1.20 mmol). The mixture was stirred at RT for 0.5 h and then at 60° C. for 4 h. The mixture was cooled, filtered through a pad of celite and poured into diethyl ether. The ether fraction was washed with brine, dried over $MgSO_4$ and concentrated. The crude compound was triturated with hot hexane to give the title compound (0.20 g, 70%) as an off white solid. MS gave the correct molecular ion $[(M+H)^+=285+]$ for the desired compound.

C

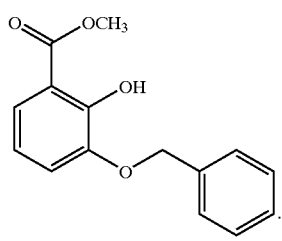

To a stirred solution of part B compound (0.14 g, 0.50 mmol) in THF (10 mL) at room temperature under argon was added a 25% solution of sodium methoxide in methanol (0.15 mL, 0.69 mmol) and the mixture was stirred at RT for 1 h. The mixture was diluted with water (50 mL) and ethyl acetate (50 mL). The suspension was treated with 2 mL of 1 N HCl solution and the organic fraction was washed with HCl solution, brine, dried over $MgSO_4$ and concentrated to an oil (0.13 g, 96%). MS gave the correct molecular ion $[(M+H)^+=259+]$ for the desired compound.

D

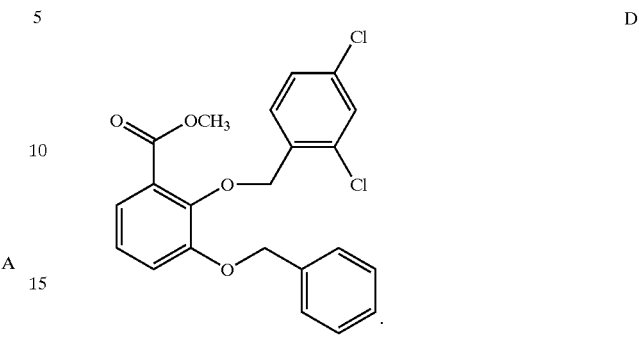

To a stirred solution of part C compound (0.05 g, 0.20 mmol) in DMF (2 mL) at room temperature under argon was added $K_2CO_3$ (0.11 g, 0.80 mmol), tetrabutylammonium iodide (3 mg, catalyst) and 2,4-dichlorobenzyl chloride (0.06 mL, 0.40 mmol). The mixture was stirred at RT for 0.5 h and then at 60° C. for 4 h. The mixture was cooled, filtered through a pad of celite and poured into diethyl ether. The ether fraction was washed with brine, dried over $MgSO_4$ and concentrated. The crude compound was crystallized from hot hexane to give the title compound (0.06 g, 72%) as a white solid. MS gave the correct molecular ion $[(M+H)^+=417+]$ for the desired compound.

E

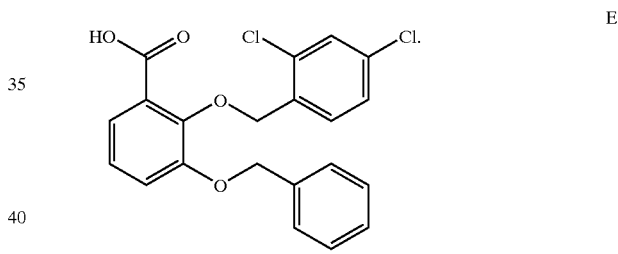

A solution of part D compound (0.05 g, 0.12 mmol) in a THF:methanol (1 mL:1 mL) solution was stirred at room temperature under argon, as 10 M NaOH solution (0.1 mL, 1.00 mmol) was added. After 4 h, the reaction mixture was concentrated and diluted with water (5 mL). The mixture was acidified to pH=1 with 1N HCl and the white solid collected (0.03 g, 60%). LC/MS gave the correct molecular ion $[(M-H)^-=401^-]$ for the title compound. mp 140–142° C.

EXAMPLE 354

3-[(2,4-Dichlorophenyl)methoxy]-2-(phenylmethoxy)benzoic acid

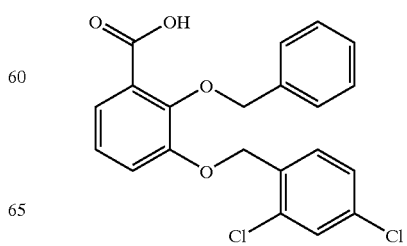

-continued

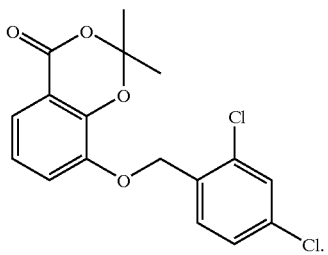
A

To a stirred solution of Example 25 part A compound (0.19 g, 1.00 mmol) in DMF (5 mL) at room temperature under argon was added K$_2$CO$_3$ (0.28 g, 2.00 mmol), tetrabutylammonium iodide (17 mg, catalyst) and 2,4-dichlorobenzyl chloride (0.17 mL, 1.20 mmol). The mixture was stirred at RT for 0.5 h and then at 60° C. for 4 h. The mixture was cooled, filtered through a pad of celite and poured into diethyl ether. The ether fraction was washed with brine, dried over MgSO$_4$ and concentrated. The crude compound was triturated with hexane to give the title compound (0.23 g, 65%) as a white solid. MS gave the correct molecular ion [(M+H)$^+$=353+] for the desired compound.

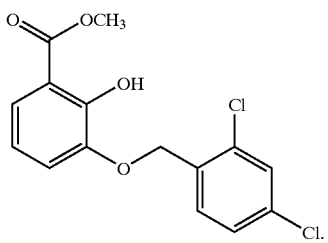
B

To a stirred solution of part A compound (0.18 g, 0.50 mmol) in THF (10 mL) at room temperature under argon was added a 25% solution of sodium methoxide in methanol (0.15 mL, 0.65 mmol) and the mixture was stirred at RT for 1 h. The mixture was diluted with water (50 mL) and ethyl acetate (50 mL). The suspension was treated with 2 mL of 1 N HCl solution and the organic fraction was washed with HCl solution, brine, dried over MgSO$_4$ and concentrated to an off white solid (0.15 g, 92%). MS gave the correct molecular ion [(M+H)$^+$=327+] for the desired compound.

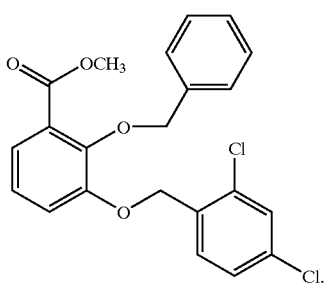
C

To a stirred solution of part B compound (0.10 g, 0.30 mmol) in DMF (3 mL) at room temperature under argon was added K$_2$CO$_3$ (0.17 g, 1.20 mmol), and benzyl bromide (0.07 mL, 0.60 mmol). The mixture was stirred at RT for 0.5 h and then at 60° C. for 4 h. The mixture was cooled, filtered through a pad of celite and poured into diethyl ether. The ether fraction was washed with brine, dried over MgSO$_4$ and concentrated. The crude compound was purified by flash column chromatography on silica gel with ethyl acetate:hexane 7:93 to give the title compound (0.11 g, 93%) as a white solid. mp 166–168° C.

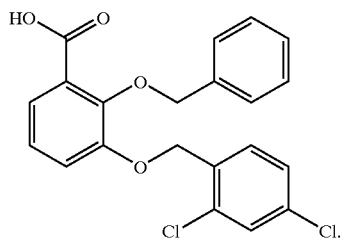
D

A solution of part C compound (0.03 g, 0.07 mmol) in a THF:methanol (1 mL:1 mL) solution was stirred at room temperature under argon, as 10 M NaOH solution (0.06 mL, 0.60 mmol) was added. After 4 h, the reaction mixture was concentrated and diluted with water (5 mL). The mixture was acidified to pH=1 with 1N HCl and the white solid collected (0.02 g, 71%). LC/MS gave the correct molecular ion [(M–H)$^-$=401$^-$] for the title compound. mp 151–153° C.

EXAMPLE 355

5-Bromo-2,3-bis[(2-chlorophenyl)methoxy]benzoic acid

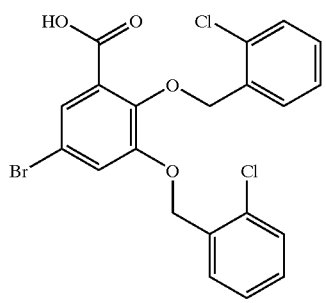

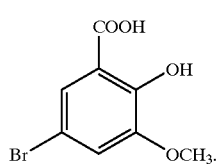
A

A solution of 5-bromo-2-hydroxy-3-methoxybenzaldehyde (1.03 g, 4.33 mmol) and sulfamic acid (563 mg, 5.78 mmol) in THF:H$_2$O (1:2, 15.9 mL) was treated dropwise with a solution of sodium hypochlorite (519 mg, 4.59 mmol) in water (2.6 mL) and the resulting orange solution stirred at room temperature for 3.0 h. The mixture was treated with 5 % KHSO$_4$ (6.6 mL), extracted with EtOAc (2×70 mL) and the organic phase was washed with brine (14 mL), dried (MgSO$_4$) and concentrated to give a light brown solid. Trituration of the crude product with CH$_2$Cl$_2$:hexane (1:1, 10 mL) and hexane (10 mL) gave the title compound as a light brown solid (753 mg, 70%), mp 195–198° C. LC/MS gave the correct molecular ion [(M–H)$^-$=245] for the desired compound.

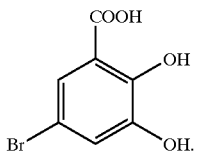
B

A cooled (0° C.) solution of part A compound (753 mg, 3.05 mmol) in dry CH$_2$Cl$_2$ (9.0 mL) was treated with 1.0 M BBr$_3$/CH$_2$Cl$_2$ (6.2 mL, 6.1 mmol), stirred at 0° C. for 3.0 h then allowed to come up to room temperature overnight (J. Med. Chem. 1995, 38, 4937–4943). The reaction mixture was quenched by the dropwise addition of water (19 mL), stirred for 30 min then extracted with EtOAc (3×100 mL). The extracts were washed with water (3×20 mL), brine (20 mL) and dried (MgSO$_4$) to give the title compound as a light brown solid (626 mg, 88%), mp 211–213° C. LC/MS gave the correct molecular ion [(M–H)$^-$=231] for the desired compound.

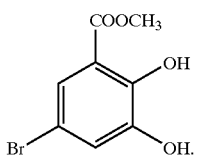
C

A mixture of thionyl chloride (0.35 mL, 4.8 mmol) and methanol (5.4 mL) was stirred at room temperature for 30 min then treated with part B compound (600 mg, 2.57 mmol). The reaction mixture was stirred at room temperature for 2.0 hr. refluxed for 7.0 hr, cooled and concentrated to a brown solid. Purification by column chromatography (2.5×25 cm column, 1:4 EtOAc/hexane, then 1:1 EtOAc) gave the title compound (500 mg, 78%).

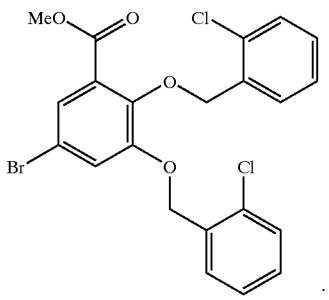
D

To a mixture of part C compound (205 mg, 0.83 mmol), potassium carbonate (900 g, 6.64 mmol) and Bu$_4$NI (cat) in dry DMF (3.4 mL) was added 2-chlorobenzylchloride (0.42 mL, 3.32 mmol). The reaction mixture was heated at 60° C. for 4 hr and partitioned between water (25 mL) and Et$_2$O (3×60 mL). The organic extracts were washed with water (3×25 mL) and brine (25 mL) and dried (MgSO$_4$) to give a syrup. Purification by flash chromatography (2.5×25 cm column, 1:9 EtOAc/hexane) gave the title compound as a white solid (392 mg, 95%), mp 100–101° C.

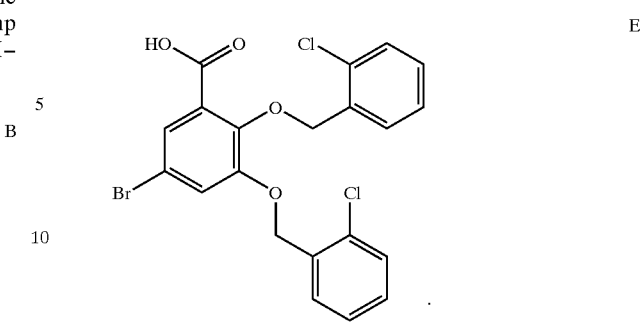
E

A solution of part D compound (387 mg, 0.78 mmol) in THF:CH$_3$OH (1:1, 3.0 mL) was treated with 10.0 N sodium hydroxide (0.17 mL, 1.7 mmol) and stirred at room temperature for 18 h. The mixture was concentrated and the solids obtained were suspended in water (5.0 mL), acidified to pH 1 with 1.0 N hydrochloric acid (2.1 mL) and extracted with EtOAc (2×60 mL). The organic phase was washed with water (3×5.0 mL) and brine (5.0 mL), dried (MgSO$_4$) and concentrated to give a white solid. Trituration of the solid with CH$_2$Cl$_2$ (4.0 mL) and hexane (25 mL) gave the title compound as a white solid (346 mg, 92%), mp 186–187° C. LC/MS gave the correct molecular ion [(M–H)$^-$=479] for the desired compound.

EXAMPLE 356

5-Bromo-2,3-bis(phenylmethoxy)benzoic acid

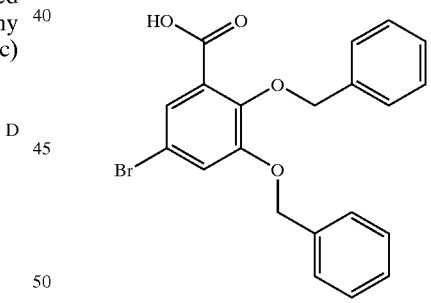

Example 356 was prepared by the method of Example 355. The title compound was obtained as a white solid (128 mg, 94%), mp 151–153° C. LC/MS gave the correct molecular ion [(M+H)$^+$=413] for the desired compound.

EXAMPLES 357–372

The following compounds were prepared according to the methods outlined in Example 345.

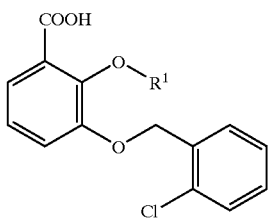

| Ex. | R¹ | MS | m.p. (° C.) | Name |
|---|---|---|---|---|
| 357 | 3-methylphenyl-CH₂– | 383 [M-H] | 107–109 | 3-[(2-Chlorophenyl)methoxy]-2-[(3-methylphenyl)methoxy]benzoic acid |
| 358 | 3-fluorophenyl-CH₂– | 387 [M-H] | 152–154 | 3-[(2-Chlorophenyl)methoxy]-2-[(3-fluorophenyl)methoxy]benzoic acid |
| 359 | 3-trifluoromethylphenyl-CH₂– | 437 [M-H] | 128–129 | 3-[(2-Chlorophenyl)methoxy]-2-[[3-trifluoromethyl)phenyl]methoxy]benzoic acid |
| 360 | 4-(phenylmethoxy)phenyl-CH₂– | 473 [M-H] | 107–109 | 3-[(2-Chlorophenyl)methoxy]-2-[[4-(phenylmethoxy)phenyl]methoxy]benzoic acid |
| 361 | 3,5-dimethylphenyl-CH₂– | 397 [M-H] | 122–123 | 3-[(2-Chlorophenyl)methoxy]-2-[(3,5-dimethylphenyl)methoxy]benzoic acid |
| 362 | 2-methoxyphenyl-CH₂– | 399 [M-H] | 110–112 | 3-[(2-Chlorophenyl)methoxy]-2-[(2-methoxyphenyl)methoxy]benzoic acid |
| 363 | 2-pyridinyl-CH₂– | 370 [M-H] | 168–170 | 3-[(2-Chlorophenyl)methoxy]-2-[(2-pyridinylmethoxy)benzoic acid |
| 364 | 4-pyridinyl-CH₂– | 370 [M-H] | 157–159 | 3-[(2-Chlorophenyl)methoxy]-2-[(4-pyridinylmethoxy)benzoic acid |

-continued

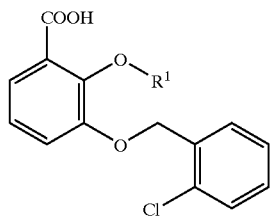

| Ex. | R¹ | MS | m.p. (° C.) | Name |
|---|---|---|---|---|
| 365 | (3-pyridinylmethyl) | 370 [M-H] | 181–182 | 3-[(2-Chlorophenyl)methoxy]-2-[(3-pyridinylmethoxy)benzoic acid |
| 366 | (2-chloro-3-pyridinylmethyl) | 404 [M-H] | 183–184 | 3-[(2-Chlorophenyl)methoxy]-2-[(2-chloro-3-pyridinyl)methoxy)benzoic acid |
| 367 | (1-oxido-2-pyridinylmethyl) | 386 [M-H] | 189–191 | 3-[(2-Chlorophenyl)methoxy]-2-[(1-oxido-2-pyridinyl)methoxy]benzoic acid |
| 368 | (1-oxido-3-pyridinylmethyl) | 386 [M-H] | 177–179 | 3-[(2-Chlorophenyl)methoxy]-2-[(1-oxido-3-pyridinyl)methoxy]benzoic acid |
| 369 | (1-oxido-4-pyridinylmethyl) | 386 [M-H] | 186–188 | 3-[(2-Chlorophenyl)methoxy]-2-[(1-oxido-4-pyridinyl)methoxy]benzoic acid |
| 370 | (2-chloro-1-oxido-3-pyridinylmethyl) | 420 [M-H] | 145–148 | 3-[(2-Chlorophenyl)methoxy]-2-[(2-chloro-1-oxido-3-pyridinyl)methoxy]benzoic acid |
| 371 | (1H-benzimidazol-2-ylmethyl) | 409 [M-H] | 197–201 | 2-(1H-Benzimidazol-2-ylmethoxy)-3-[(2-chlorophenyl)methoxyl]benzoic acid, monohydrochloride |
| 372 | (1-methyl-1H-benzimidazol-2-ylmethyl) | 423 [M-H] | 179–182 | 3-[(2-Chlorophenyl)methoxy]-2-[(1-methyl-1H-benzimidazol]-2-yl)methoxy]benzoic acid |

EXAMPLE 373

6-Bromo-2,3-bis[[(2-chlorophenyl)methoxy]benzoic acid

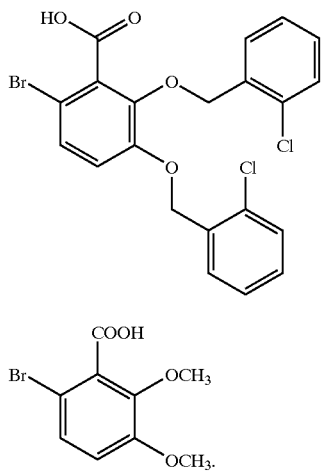

A

A cooled (0° C.) solution of 2,3-dimethoxybenzoic acid (1.0 g, 5.5 mmol) in 1.4 M NaOH (8.63 mL, 12.1 mmol) was treated portionwise with N-bromosuccinimide (1.185 g, 6.59 mmol), brought to room temperature and stirred for 48.0 hr (Tet. Lett, 1993, 34 (6), 931–934). The mixture was quenched with 5% NaHSO$_3$ solution (30 mL), acidified with 12 N hydrochloric acid to pH 1 and extracted with Et$_2$O (2×50 mL). The organic phase was washed with H$_2$O (3×10 mL) and brine (10 mL), dried (MgSO$_4$) and concentrated to give the title compound as a syrup (1.43 g, 100%).

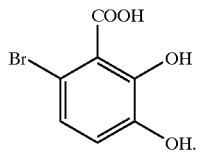

B

A cooled (0° C.) solution of part A compound (1.43 g, 5.49 mmol) in dry dichloromethane (6.0 mL) was treated with 1.0 M BBr$_3$/CH$_2$Cl$_2$ (11.0 mL, 11.0 mmol), stirred at 0° C. for 3.0 h then allowed to come up to room temperature overnight (J. Med. Chem. 1995, 38, 4937–4943). The reaction mixture was quenched by the dropwise addition of water (35 mL) followed by 1.0 N hydrochloric acid (70 mL), stirred for 15 min then extracted with EtOAc (3×100 mL). The extracts were washed with water (2×50 mL), brine (25 mL) and dried (MgSO$_4$) to give the title compound as a solid (1.163 g, 91%). LC/MS gave the correct molecular ion [(M−H)$^-$=231] for the desired compound.

C

A mixture of thionyl chloride (0.60 mL, 8.2 mmol) and methanol (10.0 mL) was stirred at room temperature for 30 min then treated with part B compound (1.15 g, 4.94 mmol). The reaction mixture was stirred at room temperature for 1 h, refluxed for 7 h, cooled and concentrated to a brown solid. Purification by column chromatography (2.5×25 cm column, 1:9 EtOAc/hexane, then 1:4 EtOAc/hexane) gave the title compound (550 mg, 45%). LC/MS gave the correct molecular ion [(M−H)$^-$=245] for the desired compound.

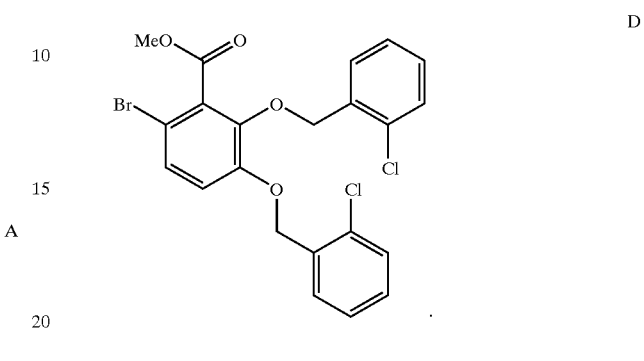

D

To a mixture of part C compound (200 mg, 0.83 mmol), potassium carbonate (900 mg, 6.64 mmol) and Bu$_4$NI (cat) in dry DMF (3.4 mL) was added 2-chlorobenzyl chloride (0.42 mL, 3.32 mmol) (J. Med. Chem. 1997, 40, 105–111). The reaction mixture was heated at 60° C. for 4 h and partitioned between water (25 mL) and Et$_2$O (3×60 mL). The organic extracts were washed with water (3×25 mL) and brine (25 mL) and dried (MgSO$_4$) to give a syrup. Purification by flash chromatography (2.5×25 cm column, 1:9 EtOAc/hexane) gave the title compound as a clear thick syrup (421 mg, 100%).

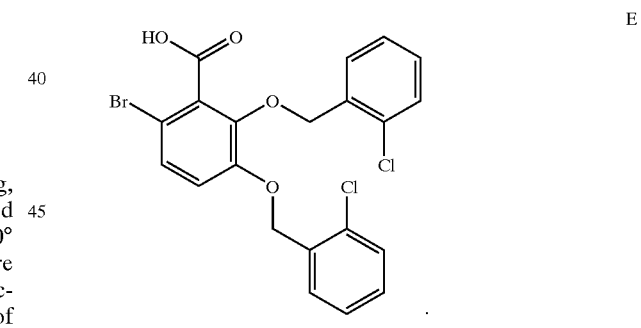

E

A solution of part D compound (421 mg, 0.83 mmol) in 1:1:1 THF/CH$_3$OH/H$_2$O (11 mL) was treated with 10.0 N sodium hydroxide (0.58 mL, 5.8 mmol) and stirred at room temperature for 24 h and then refluxed for 48 h. The mixture was concentrated and the solids obtained were suspended in water (6.0 mL), acidified to pH 1.0 with 1.0 N hydrochloric acid and extracted with EtOAc (2×65 mL). The organic phase was washed with water (3×6.0 mL) and brine (6.0 mL), dried (MgSO$_4$) and concentrated to give a white solid. Trituration of the solid with CH$_2$Cl$_2$ (5 mL) and hexane (25 mL) gave the title compound as a white solid (335 mg, 94%), mp 156–158° C. LC/MS gave the correct molecular ion [(M−H)$^-$=479] for the desired compound.

EXAMPLE 374

6-Bromo-2,3-bis(phenylmethoxy)benzoic acid

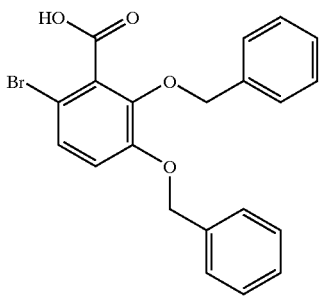

Example 374 was prepared using the method of Example 373. The title compound was obtained as a white solid (65 mg, 65%), mp 164–166° C. LC/MS gave the correct molecular ion [(M+H)$^+$=415] for the desired compound.

EXAMPLE 375

2-(Benzoylamino)-3-(phenylmethoxy)benzoic acid

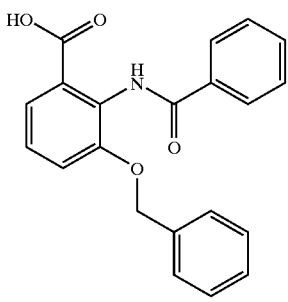

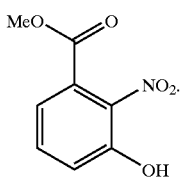

To a stirred mixture of methanol (55 mL) and thionyl chloride (3.19 mL, 43.7 mmol) was added 3-hydroxy-2-nitrobenzoic acid (5.0 g, 27.3 mmol). The reaction mixture was stirred at room temperature for 2 h, refluxed for 7 h then evaporated. Purification by flash chromatography (2.5×10 cm column, 1:3 EtOAc/hexane) gave the title compound as a light yellow solid (5.03 g, 93% yield), mp 114–116° C. LC/MS gave the correct molecular ion [(M–H)$^-$=196] for the desired compound.

B

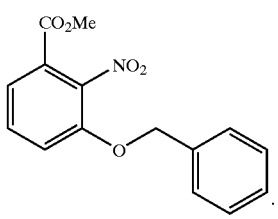

A mixture of part A compound (1.0 g, 5.07 mmol) and potassium carbonate (700 mg, 5.07 mmol) in dry DMF (10 mL) was treated with benzyl bromide (992 mg, 5.8 mmol) and heated at 100° C. for 2 h. The mixture was concentrated and partitioned between EtOAc (3×50 mL) and water (10 mL). The organic phase was washed with H$_2$O (3×10 mL) and brine (10 mL), dried (MgSO$_4$) and evaporated. Purification by flash chromatography (2.5×25 cm column, 1:4 EtOAc/hexane) provided the title compound as a white solid (1.32 g, 91% yield), mp 96–98° C.

C

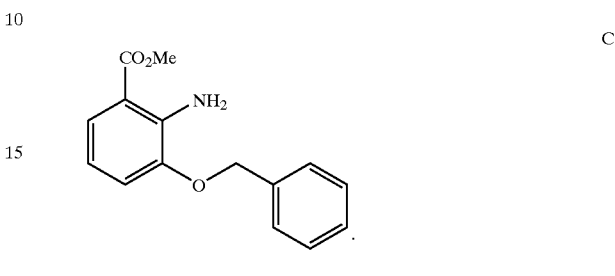

A solution of part B compound (6.12 g, 21.3 mmol) in glacial HOAc (120 mL) was cooled to 0° C., treated with zinc powder (13.71 g, 210 mmol), brought to room temperature and stirred for 2 h (J. Med. Chem. 1997, 40, 105–111). The mixture was filtered, washing the powder with glacial HOAc (25 mL), and the reddish-brown solution concentrated and re-evaporated several times with toluene. The crude product was partitioned between water (40 mL) and CH$_2$Cl$_2$ (2×150 mL) followed by extraction with EtOAc (150 mL). The organic extracts were washed with water (2×40 mL) and brine (40 mL), dried (MgSO$_4$) and concentrated to a syrup. Purification by flash chromatography (2.5×10 cm column, 1:9 EtOAc/hexane, then 1:4 EtOAc/hexane) gave the desired compound as a white solid (3.36 g, 87%), mp 81–82° C. LC/MS gave the correct molecular ion [(M+H)$^+$=258] for the title compound.

D

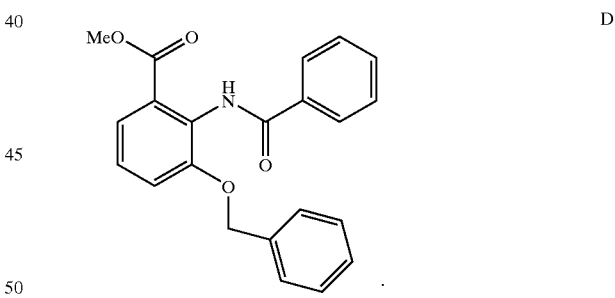

To a solution of part C compound (300 mg, 1.17 mmol) in dry CH$_2$Cl$_2$ (6.0 mL) was added dry pyridine (119 mg, 1.5 mmol) followed by a solution of benzoyl chloride (181 mg, 1.29 mmol) in dry CH$_2$Cl$_2$ (6.0 mL) (J. Med. Chem 1994, 37, 4251–4257). The reaction mixture was stirred at room temperature for 19 h, diluted with CH$_2$Cl$_2$ (13 mL) and washed with 1.0 N hydrochloric acid (2.0 mL). The aqueous phase was back-extracted with CH$_2$Cl$_2$ (25 mL) and the organic fractions were washed with 5% sodium bicarbonate solution (2.0 mL), water (2×2.0 mL) and brine (2.0 mL), dried (MgSO$_4$) and concentrated to a white solid. Purification by flash chromatography (2.5×25 cm column, 1:9 EtOAc/Hexane, then 1:4 EtOAc/Hexane) gave the title compound as a white solid (357 mg, 85%), mp 126–128° C.

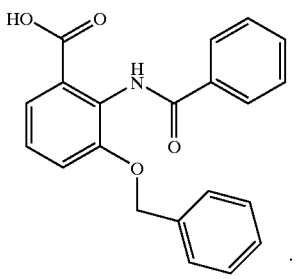

E

A solution of part D compound (100 mg, 0.28 mmol) in dry CH$_3$OH (5.0 mL) was treated with 1.0 N sodium hydroxide solution (0.8 mL) and stirred at room temperature for 5.0 h, then heated to reflux for 30 min. The solution was concentrated and the crude product dissolved in water (2.0 mL), acidified to pH 1 with 1.0 N hydrochloric acid (0.9 mL) and extracted with EtOAc (3×10 mL). The organic extracts were washed with water (3×2 mL) and brine (2 mL), dried (MgSO$_4$) and concentrated to give the title compound as a white solid (96.9 mg, 100%), mp 167–168° C. LC/MS gave the correct molecular ion [(M+H)$^+$=348 ] for the desired compound.

EXAMPLES 376–391

The following compounds were prepared according to the methods outlined in Example 375.

| Ex. | R$^1$ | R$^2$ | m/z [M-H]$^-$ | m.p. (° C.) | Name |
|---|---|---|---|---|---|
| 376 | (4-methylphenyl)sulfonylamino | phenylmethyl | 398 | 153–155 | 2-[[(4-Methylphenyl)sulfonyl]amino]-3-(phenylmethoxy)benzoic acid |
| 377 | N-methylbenzoylamino | phenylmethyl | 362 | 184–186 | 2-(Benzoylmethylamino)-3-(phenylmethoxy)benzoic acid |
| 378 | (3-chlorobenzoyl)amino | phenylmethyl | 382 | 161–163 | 2-[(3-Chlorobenzoyl)amino]-3-(phenylmethoxy)benzoic acid |
| 379 | (4-chlorobenzoyl)amino | phenylmethyl | 382 | 170–172 | 2-[(4-Chlorobenzoyl)amino]-3-(phenylmethoxy)benzoic acid |
| 380 | N-benzyl-benzoylamino | phenylmethyl | 438 | 161–163 | 2-[Benzoyl(phenylmethyl)amino]-3-(phenylmethoxy)benzoic acid |

-continued

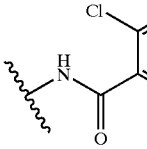

| Ex. | R¹ | R² | m/z [M-H]⁻ | m.p. (° C.) | Name |
|---|---|---|---|---|---|
| 381 | 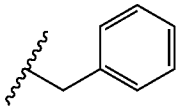 | 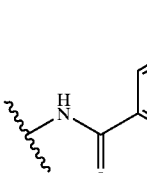 | 414 | 208–210 | 2-[(2,4-Dichlorobenzoyl)amino]-3-(phenylmethoxy)benzoic acid |
| 382 | 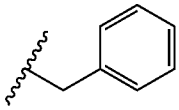 | 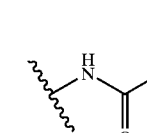 | 414 | 202–204 | 2-[(3,5-Dichlorobenzoyl)amino]-3-(phenylmethoxy)benzoic acid |
| 383 | 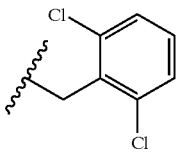 | 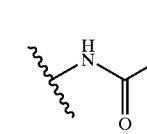 | 414 | 145–147 | 2-(Benzoylamino)-3-(2,6-dichlorophenyl)methoxy]benzoic acid |
| 384 | 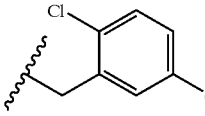 | 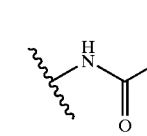 | 414 | 187–189 | 2-(Benzoylamino)-3-(2,5-dichlorophenyl)methoxy]benzoic acid |
| 385 | 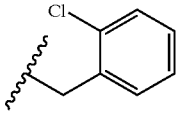 | 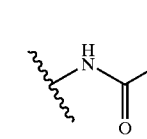 | 382 | 180–182 | 2-(Benzoylamino)-3-[(2-chlorophenyl)methoxy]benzoic acid |
| 386 | 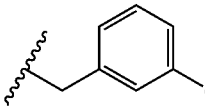 | 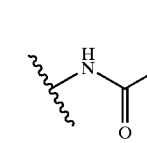 | 382 | 90–92 | 2-(Benzoylamino)-3-(3-chlorophenyl)methoxy]benzoic acid |
| 387 | 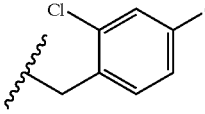 | 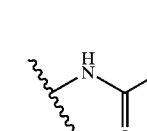 | 414 | 182–184 | 2-(Benzoylamino)-3-[(2,4-dichlorophenyl)methoxy]benzoic acid |
| 388 | 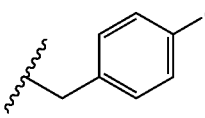 | | 382 | 142–144 | 2-(Benzoylamino)-3-[(4-chlorophenyl)methoxy]benzoic acid |

-continued

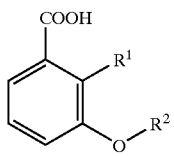

| Ex. | R¹ | R² | m/z [M-H]⁻ | m.p. (° C.) | Name |
|---|---|---|---|---|---|
| 389 | ![2-chlorobenzoylamino] | ![2-chlorophenylmethoxy] | 416 | 225–227 | 2-[(2-Chlorobenzoyl)amino]-3-[(2-chlorophenyl)methoxy]benzoic acid |
| 390 | ![cyclohexylcarbonylamino] | ![2-chlorophenylmethoxy] | 388 | 196–198 | 3-[(2-Chlorophenyl)methoxy]-2-[(cyclohexylcarbonyl)amino]benzoic acid |
| 391 | ![2-chlorophenylsulfonylamino] | ![2-chlorophenylmethoxy] | 451 | 171–174 | 3-[(2-Chlorophenyl)methoxy]-2-[[2-chlorophenyl)sulfonyl]amino]benzoic acid |

EXAMPLE 392

3-[(2-Chlorobenzoyl)amino]-2-[(2-chlorophenyl)methoxy]benzoic acid

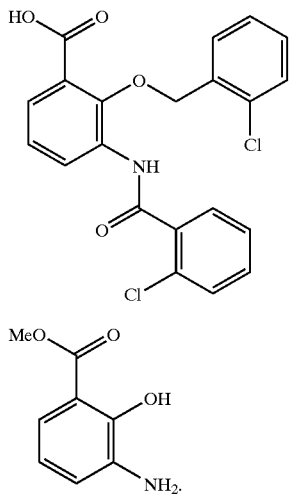

A mixture of thionyl chloride (1.15 mL, 15.8 mmol) and methanol (20.0 mL) was stirred at room temperature for 30 min then treated with 3-amino-2-hydroxybenzoic acid (1.5 g, 9.79 mmol). The reaction mixture was stirred at room temperature for 2 h, refluxed for 20 h, cooled and concentrated. The crude product was partitioned between EtOAc (100 mL) and 5% NAHCO₃ solution (65 mL), back-extracting the aqueous phase with EtOAc (4×100 mL). The organic phase was washed with water (2×20 mL) and brine (20 mL), dried (MgSO₄), filtered and concentrated to give a dark red solid (381 mg, 19%).

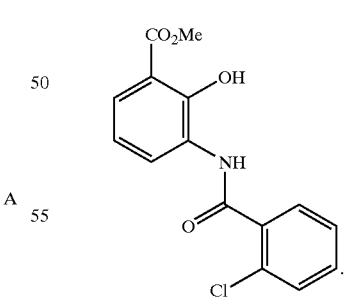

To a solution of part A compound (381 mg, 1.9 mmol) and dry pyridine (0.18 mL) in dry CH₂Cl₂ (11.0 mL) was added 2-chlorobenzoylchloride (0.29 mL, 2.18 mmol) (J. Med. Chem. 1994, 37, 4251–4257). The reaction mixture was stirred at room temperature for 24 h and then partitioned between 1.0 N hydrochloric acid (3.0 mL) and CH₂Cl₂

(2×25 mL). The organic phase was washed with water (2×3.0 mL) and brine (3 mL), dried (MgSO₄) and concentrated to give a semi-solid. Purification by flash chromatography (2.5×25 cm column, 1:9 EtOAc/hexane) gave the title compound as an off-white solid (569 mg, 99%). LC/MS gave the correct molecular ion [(M+H)$^+$=306] for the desired compound.

C

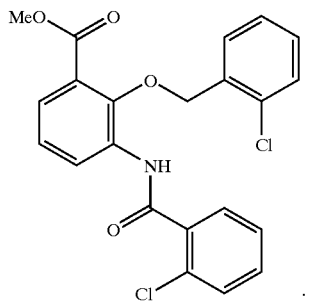

A mixture of part B compound (100 mg, 0.33 mmol), potassium carbonate (92 mg, 0.66 mmol) and Bu₄NI (~5 mg) in dry dimethyformamide (1.5 mL) was treated with 2-chlorobenzylchloride (0.05 mL, 0.43 mmol) and stirred at 60° C. for 3 h. The mixture was concentrated and the slurry partitioned between water (2.0 mL) and EtOAc (2×20 mL). The organic phase was washed with water (2×2.0 mL) and brine (2 mL), dried (MgSO₄) and concentrated to give a syrup. Purification by flash chromatography (2.5×25 cm column, 1:9 EtOAc/Hexane) gave the title compound as a clear syrup (125 mg, 88%).

D

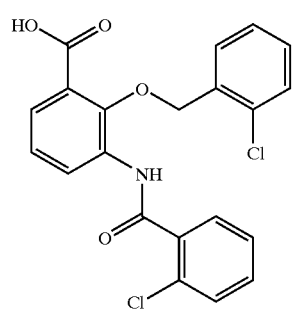

A solution of part C compound (125 mg, 0.29 mmol) in CH₃OH (4.7 mL) was treated with 1.0 N sodium hydroxide solution (0.8 mL, 0.8 mmol) and refluxed for 2 h. The mixture was concentrated and the solids were dissolved in water (2.0 mL), acidified with 1.0 N hydrochloric acid (0.89 mL) to pH 1 and partitioned between water (2 mL) and EtOAc (2×50 mL). The organic phase was washed with water (2×4.0 mL) and brine (4.0 mL), dried (MgSO₄) and concentrated to give the title compound as a white solid (125 mg, 100%), mp 182–183° C. LC/MS gave the correct molecular ion [(M+H)$^+$=418] for the desired compound.

EXAMPLE 393

3-[(2-Chlorobenzoyl)amino]-2-[(4-methoxyphenyl)methoxy]benzoic acid

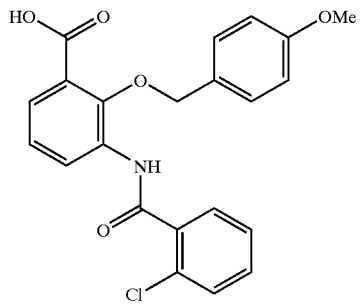

Example 393 was prepared by the method of Example 392. The title compound was obtained as a white solid (47 mg, 88%), mp 115–117° C. This compound was acid-labile and an LC/MS or HPLC could not be obtained.

EXAMPLES 394–571

The compounds of examples 394–571 were prepared as part of a solid-phase library run using the following procedure.

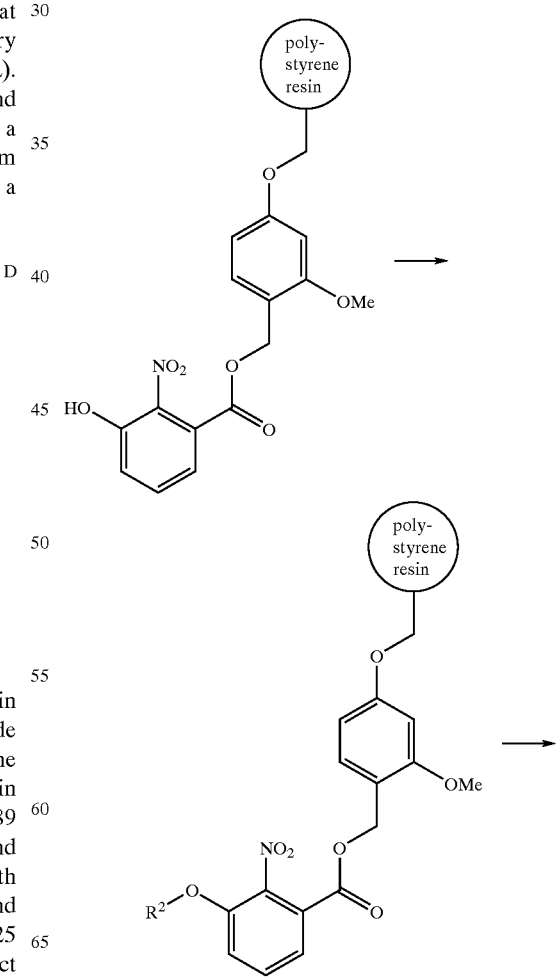

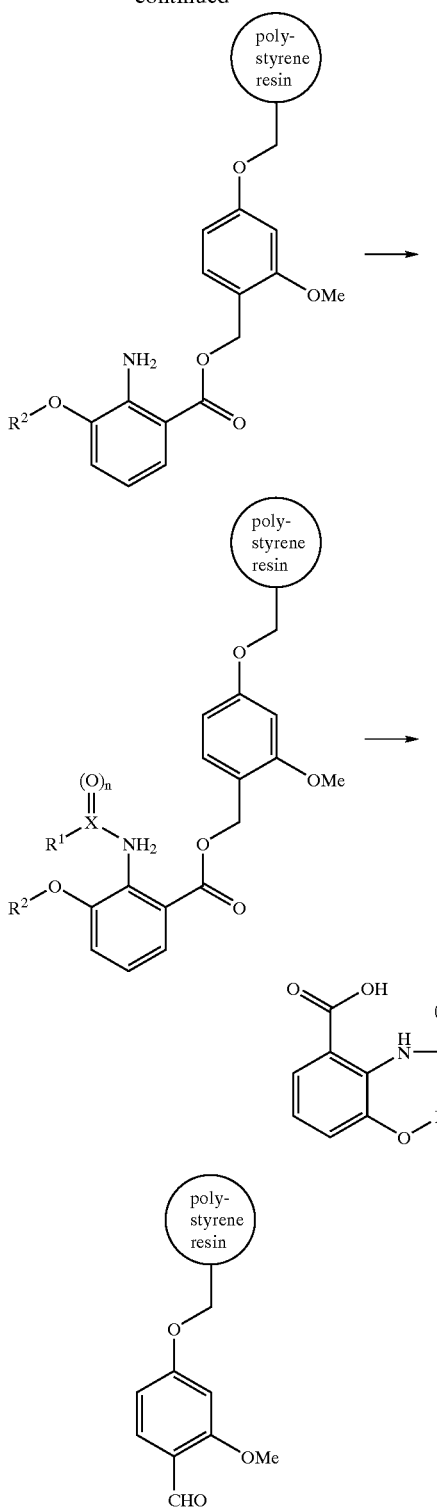

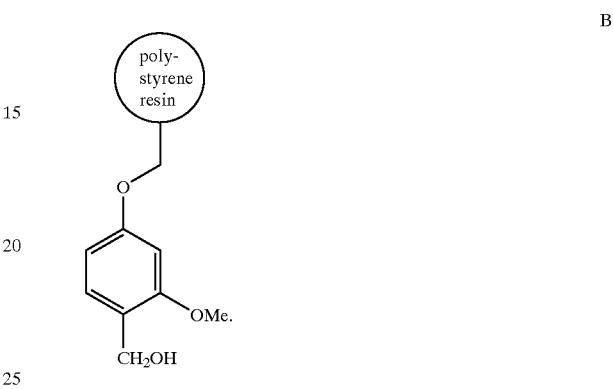

To a stirred suspension of sodium hydride (60% mineral oil dispersion, 10.5 g, 0.263 mol) in DMF (100 mL) at 4° C. was added a solution of 2-methoxy-4-hydroxy-benzaldehyde (40.0 g, 0.263 mol) in DMF (200 mL) over 2 h. The reaction mixture was warmed to room temperature and stirred for 1 h, whereupon tetrabutylammonium iodide (13.0 g, 35.2 mmol) and Merrifield polystyrene resin (100 g, 1.24 mmol chloride/g, 124 mmol) was added in two batches. The reaction mixture was heated to 61° C. for 19 h. The resulting solid was collected and washed with the following sequence: five times with 1:1 DMF-water, five times with DMF, once with DMF-water, once with DMF, three times with THF, once with methanol and once with THF. The solids were dried in vacuum at room temperature to constant weight to give the title compound (117.1 g). Elemental analysis showed a residual chloride content of 0.15% by weight. The calculated loading was 1.084 mmol/g.

B

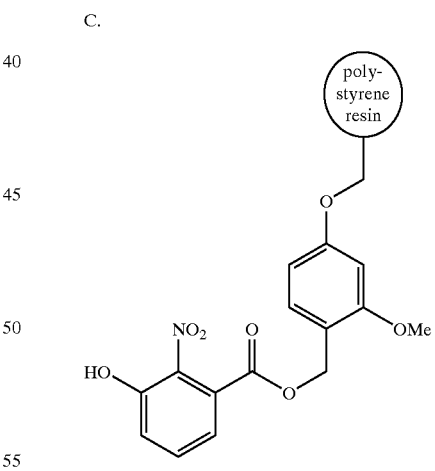

To an agitated suspension (at 150 rpm) of Part A resin (53.3 g, 57.6 mmol) in THF (150 mL) and ethanol (150 mL) at room temperature was added solid sodium borohydride (11.48 g, 317 mmol). After 20 h, the resulting solid was collected and washed with the following sequence: four times with 1:1 DMF-water, three times with DMF, four times with 1:19 acetic acid/THF, twice with THF and four times with dichloromethane. The solids were dried in vacuum at room temperature to constant weight to give the title compound (52.35 g).

C.

To a solution of triphenylphosphine (45.3 g, 173 mmol) in $CH_2Cl_2$ (200 mL) at 4° C. was added triphosgene (46.6 g, 173 mmol) portionwise over 30 min. After an additional 10 min, the reaction mixture was warmed to room temperature and stirred for 30 min. The reaction mixture was evaporated re-evaporated once from $CH_2Cl_2$ and the resulting solid redissolved in $CH_2Cl_2$ (90 mL). This solution was added to an agitated suspension (at 150 rpm) of Part B resin (35.0 g, 37.9 mmol) in $CH_2Cl_2$ (150 mL). After 3 h, the resulting solid was collected and washed twice with anhydrous DMF.

The washed solid was suspended in DMF (200 mL) and 3-hydroxy-2-nitro-benzoic acid (17.0 g, 92.8 mmol), sodium bicarbonate (11.23 g, 139 mmol) and tetra-n-butylammonium iodide (1.4 g, 3.8 mmol) were added and the mixture agitated at 150 rpm. After 40 h, the solid was collected and washed five times with 1:1 DMF/water followed by DMF, then four times with THF and four times with $CH_2Cl_2$. Drying in vacuum at room temperature to constant weight gave the title compound (38.83 g).

D.

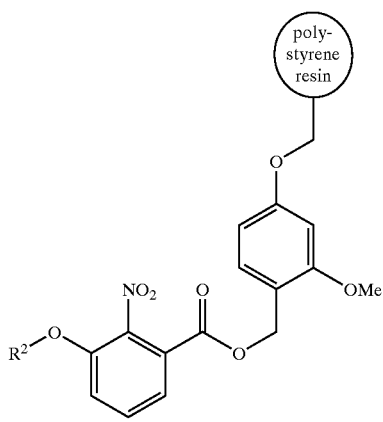

A suspension of Part C resin (1.0 g, 0.91 mmol), finely ground potassium carbonate (1.26 g, 9.1 mmol), tetrabutylammonium iodide (100 mg, 0.9 mmol) and $R^2$—X (4.6 mmol) in DMF (11.5 mL) at 68° C. was agitated at 300 rpm. After 33 h, the solid was washed four times with 1:1 DMF/water, then four times with DMF and four times with THF (15 mL portions). Drying in vacuum at room temperature to constant weight gave the title compounds. The following $R^2$—X were included: (1-bromoethyl)benzene, benzyl bromide, 2-bromobenzyl bromide, α-bromo-o-xylene, α-bromo-m-xylene, α-bromo-p-xylene, 4-bromobenzyl bromide, 4-(trifluoromethyl) benzyl bromide, 3-chlorobenzyl bromide, 2-chlorobenzyl chloride, 2,4-dichlorobenzyl chloride, 4-methoxybenzyl chloride, 4-benzyloxybenzyl chloride, 4-biphenylmethyl chloride, 2-chloroacetophenone, 2,2',4'-trichloroacetophenone, 1-iodobutane, bromomethylcyclo-hexane, 1-(chloromethyl) naphthalene, 2-(bromomethyl) naphthalene, 2,4'-dichloroacetophenone, 4-chlorobenzyl bromide, 3-phenoxybenzyl chloride and 3-methoxybenzyl bromide.

E.

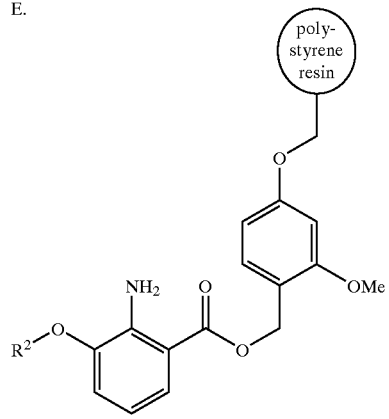

A suspension of Part D resin in THF (10 mL) was agitated at 270 rpm and then water (4.4 mL) was added, followed by potassium carbonate (1.26 g, 9.1 mmol), tetrabutylammonium hydroxide solution (0.60 mL, 1.53 M, 0.9 mmol) and sodium hydrosulfite (3.12 g, 18.2 mmol). After 76 h, the solid was washed six times with 1:1 DMF/water, then four times with DMF, three times with THF and twice with $CH_2Cl_2$ (15 mL portions) gave the title compounds.

F.

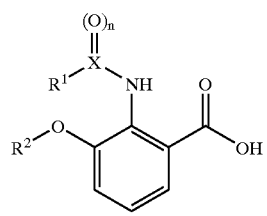

A suspension of Part D resin (60 mg) in $ClCH_2CH_2Cl$ (500 μL) was treated with a solution of DMAP in pyridine (0.5 mL, 0.1 M, 0.05 mmol) and then a solution of $R^1$—X(O)$_n$—Cl (0.5 mL, 1 M). The vessels were agitated at 580 rpm for 14 h. Each resin was washed twice with DMF, three times with 1:1 DMF/water, three times with THF, twice with $CH_2Cl_2$ (1 mL portions) and then treated with 1% TFA in $ClCH_2CH_2Cl$ for 40 min at 550 rpm. The solution was evaporated and the residues were dissolved in isopropanol (0.5 mL), filtered and evaporated to give the title compounds.

The following $R^1$—X(O)$_n$—Cl were included: benzoyl chloride, 2-chlorobenzoyl chloride, o-anisoyl chloride, 3-chlorobenzoyl chloride, m-anisoyl chloride, heptanoyl chloride, cyclohexanecarbonyl chloride, 2-quinoxaloyl choride, benzenesulfonyl chloride, 2-chloronicotinyl chloride, 3-chorobenzenesulfonyl chloride and 6-chloronicotinyl chloride.

| Ex. | CAS Name | Elemental formula | Mass Spec, m/z | ion type inferred |
|---|---|---|---|---|
| 394 | 3-[[(3-Chlorophenyl)sulfonyl]amino]-2-(1-phenylethoxy)benzoic acid | C21 H18 Cl N O5 S | 432 | (M + H) |
| 395 | 2-[(2-Chlorobenzoyl)amino]-3-(phenylmethoxy)benzoic acid | C21 H16 Cl N O4 | 382 | (M + H) |

| Ex. | CAS Name | Elemental formula | Mass Spec, m/z | ion type inferred |
|---|---|---|---|---|
| 396 | 2-[(2-Methoxybenzoyl)amino]-3-(phenylmethoxy)benzoic acid | C22 H19 N O5 | 379 | (M + H) |
| 397 | 2-[(1-Oxoheptyl)amino]-3-(phenylmethoxy)benzoic acid | C21 H25 N O4 | 356 | (M + H) |
| 398 | 2-[(Cyclohexylcarbonyl)amino]-3-(phenylmethoxy)benzoic acid | C21 H23 N O4 | 354 | (M + H) |
| 399 | 3-(Phenylmethoxy)-2-[(2-quinoxalinylcarbonyl)amino]benzoic acid | C23 H17 N3 O4 | 400 | (M + H) |
| 400 | 3-(Phenylmethoxy)-2-[(phenylsulfonyl)amino]benzoic acid | C20 H17 N O5 S | 384 | (M + H) |
| 401 | 2-[[(6-Chloro-3-pyridinyl)carbonyl]amino]-3-(phenylmethoxy)benzoic acid | C20 H15 Cl N2 O4 | 383 | (M + H) |
| 402 | 2-(Benzoylamino)-3-[(2-bromophenyl)methoxy]benzoic acid | C21 H16 Br N O4 | 426 | (M + H) |
| 403 | 3-[(2-Bromophenyl)methoxy]-2-[(3-chlorobenzoyl)amino]benzoic acid | 21 H15 Br Cl N O4 | 460 | (M + H) |
| 404 | 3-[(2-Bromophenyl)methoxy]-2-[(cyclohexylcarbonyl)amino]benzoic acid | C21 H22 Br N O4 | 432 | (M + H) |
| 405 | 3-[(2-Bromophenyl)methoxy]-2-[(2-quinoxalinylcarbonyl)amino]benzoic acid | C23 H16 Br N3 O4 | 478 | (M + H) |
| 406 | 2-(Benzoylamino)-3-[(2-methylphenyl)methoxy]benzoic acid | C22 H19 N O4 | 362 | (M + H) |
| 407 | 2-[(2-Methoxybenzoyl)amino]-3-[(2-methylphenyl)methoxy]benzoic acid | C23 H21 N O5 | 392 | (M + H) |
| 408 | 2-[(3-Chlorobenzoyl)amino]-3-[(2-methylphenyl)methoxy]benzoic acid | C22 H18 Cl N O4 | 396 | (M + H) |
| 409 | 3-[(2-Methylphenyl)methoxy]-2-[(1-oxoheptyl)amino]benzoic acid | C22 H27 N O4 | 70 | (M + H) |
| 410 | 2-[(Cyclohexylcarbonyl)amino]-3-[(2-methylphenyl)methoxy]benzoic acid | C22 H25 N O4 | 368 | (M + H) |
| 411 | 3-[(2-Methylphenyl)methoxy]-2-[(2-quinoxalinylcarbonyl)amino]benzoic acid | C24 H19 N3 O4 | 14 | (M + H) |
| 412 | 2-[[(6-Chloro-3-pyridinyl)carbonyl]amino]-3-[(2-methylphenyl)methoxy]benzoic acid | C21 H17 Cl N2 O4 | 397 | (M + H) |

-continued

| Ex. | CAS Name | Elemental formula | Mass Spec, m/z | ion type inferred |
|---|---|---|---|---|
| 413 | 2-[(2-Chlorobenzoyl)amino]-3-[(3-methylphenyl)methoxy]benzoic acid | C22 H18 Cl N O4 | 396 | (M + H) |
| 414 | 2-[(2-Methoxybenzoyl)amino]-3-[(3-methylphenyl)methoxy]benzoic acid | C23 H21 N O5 | 392 | (M + H) |
| 415 | 2-[(3-Chlorobenzoyl)amino]-3-[(3-methylphenyl)methoxy]benzoic acid | C22 H18 Cl N O4 | 396 | (M + H) |
| 416 | 2-[(3-Methoxybenzoyl)amino]-3-[(3-methylphenyl)methoxy]benzoic acid | C23 H21 N O5 | 392 | (M + H) |
| 417 | 3-[(3-Methylphenyl)methoxy]-2-[(1-oxoheptyl)amino]benzoic acid | C22 H27 N O4 | 370 | (M + H) |
| 418 | 2-[(Cyclohexylcarbonyl)amino]-3-[(3-methylphenyl)methoxy]benzoic acid | C22 H25 N O4 | 368 | (M + H) |
| 419 | 3-[(3-Methylphenyl)methoxy]-2-[(2-quinoxalinylcarbonyl)amino]benzoic acid | C24 H19 N3 O4 | 414 | (M + H) |
| 420 | 3-[(3-Methylphenyl)methoxy]-2-[(phenylsulfonyl)amino]benzoic acid | C21 H19 N O5 S | 398 | (M + H) |
| 421 | 2-[[(2-Chloro-3-pyridinyl)carbonyl]amino]-3-[(3-methylphenyl)methoxy]benzoic acid | C21 H17 Cl N2 O4 | 398 | (M + H) |
| 422 | 2-[[(3-Chlorophenyl)sulfonyl]amino]-3-[(3-methylphenyl)methoxy]benzoic acid | C21 H18 Cl N O5 S | 432 | (M + H) |
| 423 | 2-[[(6-Chloro-3-pyridinyl)carbonyl]amino]-3-[(3-methylphenyl)methoxy]benzoic acid | C21 H17 Cl N2 O4 | 397 | (M + H) |
| 424 | 2-(Benzoylamino)-3-[(4-bromophenyl)methoxy]benzoic acid | C21 H16 Br N O4 | 426 | (M + H) |
| 425 | 3-[(4-Bromophenyl)methoxy]-2-[(2-chlorobenzoyl)amino]benzoic acid | C21 H15 Br Cl N O4 | 460 | (M + H) |
| 426 | 3-[(4-Bromophenyl)methoxy]-2-[(2-methoxybenzoyl)amino]benzoic acid | C22 H18 Br N O5 | 456 | (M + H) |
| 427 | 3-[(4-Bromophenyl)methoxy]-2-[(3-chlorobenzoyl)amino]benzoic acid | C21 H15 Br Cl N O4 | 460 | (M + H) |

-continued

| Ex. | CAS Name | Elemental formula | Mass Spec, m/z | ion type inferred |
|---|---|---|---|---|
| 428 | 3-[(4-Bromophenyl)methoxy]-2-[(3-methoxybenzoyl)amino]benzoic acid | C22 H18 Br N O5 | 456 | (M + H) |
| 429 | 3-[(4-Bromophenyl)methoxy]-2-[(1-oxoheptyl)amino]benzoic acid | C21 H24 Br N O4 | 434 | (M + H) |
| 430 | 3-[(4-Bromophenyl)methoxy]-2-[(cyclohexylcarbonyl)amino]benzoic acid | C21 H22 Br N O4 | 432 | (M + H) |
| 431 | 3-[(4-Bromophenyl)methoxy]-2-[(2-quinoxalinylcarbonyl)amino]benzoic acid | C23 H16 Br N3 O4 | 478 | (M + H) |
| 432 | 3-[(4-Bromophenyl)methoxy]-2-[(phenylsulfonyl)amino]benzoic acid | C20 H16 Br N O5 S | 462 | (M + H) |
| 433 | 3-[(4-Bromophenyl)methoxy]-2-[[(2-chloro-3-pyridinyl)carbonyl]amino]benzoic acid | C20 H14 Br Cl N2 O4 | 461 | (M + H) |
| 434 | 3-[(4-Bromophenyl)methoxy]-2-[[(3-chlorophenyl)sulfonyl]amino]benzoic acid | C20 H15 Br Cl N O5 S | 496 | (M + H) |
| 435 | 3-[(4-Bromophenyl)methoxy]-2-[[(6-chloro-3-pyridinyl)carbonyl]amino]benzoic acid | C20 H14 Br Cl N2 O4 | 461 | (M + H) |
| 436 | 2-[(2-Methoxybenzoyl)amino]-3-[(4-methylphenyl)methoxy]benzoic acid | C23 H21 N O5 | 392 | (M + H) |
| 437 | 2-[(3-Chlorobenzoyl)amino]-3-[(4-methylphenyl)methoxy]benzoic acid | C22 H18 Cl N O4 | 397 | (M + H) |
| 438 | 2-[(3-Methoxybenzoyl)amino]-3-[(4-methylphenyl)methoxy]benzoic acid | C23 H21 N O5 | 392 | (M + H) |
| 439 | 3-[(4-Methylphenyl)methoxy]-2-[(1-oxoheptyl)amino]benzoic acid | C22 H27 N O4 | 370 | (M + H) |
| 440 | 2-[(Cyclohexylcarbonyl)amino]-3-[(4-methylphenyl)methoxy]benzoic acid | C22 H25 N O4 | 368 | (M + H) |
| 441 | 3-[(4-Methylphenyl)methoxy]-2-[(2-quinoxalinylcarbonyl)amino]benzoic acid | C24 H19 N3 O4 | 414 | (M + H) |
| 442 | 2-[[(2-Chloro-3-pyridinyl)carbonyl]amino]-3-[(4-methylphenyl)methoxy]benzoic acid | C21 H17 Cl N2 O4 | 397 | (M + H) |

| Ex. | CAS Name | Elemental formula | Mass Spec, m/z | ion type inferred |
|---|---|---|---|---|
| 443 | 2-[[(3-Chlorophenyl)sulfonyl]amino]-3-[(4-methylphenyl)methoxy]benzoic acid | C21 H18 Cl N O5 S | 432 | (M + H) |
| 444 | 2-[[(6-Chloro-3-pyridinyl)carbonyl]amino]-3-[(4-methylphenyl)methoxy]benzoic acid | C21 H17 Cl N2 O4 | 397 | (M + H) |
| 445 | 2-(Benzoylamino)-3-[[4-(trifluoromethyl)phenyl]methoxy]benzoic acid | C22 H16 F3 N O4 | 414 | (M + H) |
| 446 | 2-[(2-Chlorobenzoyl)amino]-3-[[4-(trifluoromethyl)phenyl]methoxy]benzoic acid | C22 H15 Cl F3 N O4 | 450 | (M + H) |
| 447 | 2-[(2-Methoxybenzoyl)amino]-3-[[4-(trifluoromethyl)phenyl]methoxy]benzoic acid | C23 H18 F3 N O5 | 446 | (M + H) |
| 448 | 2-[(3-Chlorobenzoyl)amino]-3-[[4-(trifluoromethyl)phenyl]methoxy]benzoic acid | C22 H15 Cl F3 N O4 | 450 | (M + H) |
| 449 | 2-[(3-Methoxybenzoyl)amino]-3-[[4-(trifluoromethyl)phenyl]methoxy]benzoic acid | C23 H18 F3 N O5 | 446 | (M + H) |
| 450 | 2-[(1-Oxoheptyl)amino]-3-[[4-(trifluoromethyl)phenyl]methoxy]benzoic acid | C22 H24 F3 N O4 | 424 | (M + H) |
| 451 | 2-[(Cyclohexylcarbonyl)amino]-3-[[4-(trifluoromethyl)phenyl]methoxy]benzoic acid | C22 H22 F3 N O4 | 422 | (M + H) |
| 452 | 2-[(2-Quinoxalinylcarbonyl)amino]-3-[[4-(trifluoromethyl)phenyl]methoxy]benzoic acid | C24 H16 F3 N3 O4 | 468 | (M + H) |
| 453 | 2-[(Phenylsulfonyl)amino]-3-[[4-(trifluoromethyl)phenyl]methoxy]benzoic acid | C21 H16 F3 N O5 S | 452 | (M + H) |
| 454 | 2-[[(2-Chloro-3-pyridinyl)carbonyl]amino]-3-[[4-(trifluoromethyl)phenyl]methoxy]benzoic acid | C21 H14 Cl F3 N2 O4 | 451 | (M + H) |
| 455 | 2-[[(3-Chlorophenyl)sulfonyl]amino]-3-[[4-(trifluoromethyl)phenyl]methoxy]benzoic acid | C21 H15 Cl F3 N O5 S | 486 | (M + H) |
| 456 | 2-[[(6-Chloro-3-pyridinyl)carbonyl]amino]-3-[[4-(trifluoromethyl)phenyl]methoxy]benzoic acid | C21 H14 Cl F3 N2 O4 | 451 | (M + H) |
| 457 | 2-[(2-Chlorobenzoyl)amino]-3-[(3-chlorophenyl)methoxy]benzoic acid | C21 H15 Cl2 N O4 | 416 | (M + H) |
| 458 | 3-[(3-Chlorophenyl)methoxy]-2-[(2-methoxybenzoyl)amino]benzoic acid | C22 H18 Cl N O5 | 412 | (M + H) |

-continued

| Ex. | CAS Name | Elemental formula | Mass Spec, m/z | ion type inferred |
|---|---|---|---|---|
| 459 | 2-[(3-Chlorobenzoyl)amino]-3-[(3-chlorophenyl)methoxy]benzoic acid | C21 H15 Cl2 N O4 | 416 | (M + H) |
| 460 | 3-[(3-Chlorophenyl)methoxy]-2-[(3-methoxybenzoyl)amino]benzoic acid | C22 H18 Cl N O5 | 412 | (M + H) |
| 461 | 3-[(3-Chlorophenyl)methoxy]-2-[(1-oxoheptyl)amino]benzoic acid | C21 H24 Cl N O4 | 390 | (M + H) |
| 462 | 3-[(3-Chlorophenyl)methoxy]-2-[(cyclohexylcarbonyl)amino]benzoic acid | C21 H22 Cl N O4 | 388 | (M + H) |
| 463 | 3-[(3-Chlorophenyl)methoxy]-2-[(phenylsulfonyl)amino]benzoic acid | C20 H16 Cl N O5 S | 418 | (M + H) |
| 464 | 3-[(3-Chlorophenyl)methoxy]-2-[[(2-chloro-3-pyridinyl)carbonyl]amino]benzoic acid | C20 H14 Cl2 N2 O4 | 417 | (M + H) |
| 465 | 3-[(3-Chlorophenyl)methoxy]-2-[[(3-chlorophenyl)sulfonyl]amino]benzoic acid | C20 H15 Cl2 N O5 S | 452 | (M + H) |
| 466 | 3-[(2-Chlorophenyl)methoxy]-2-[(2-methoxybenzoyl)amino]benzoic acid | C22 H18 Cl N O5 | 412 | (M + H) |
| 467 | 2-[(3-Chlorobenzoyl)amino]-3-[(2-chlorophenyl)methoxy]benzoic acid | C21 H15 Cl2 N O4 | 416 | (M + H) |
| 468 | 3-[(2-Chlorophenyl)methoxy]-2-[(3-methoxybenzoyl)amino]benzoic acid | C22 H18 Cl N O5 | 412 | (M + H) |
| 469 | 3-[(2-Chlorophenyl)methoxy]-2-[(1-oxoheptyl)amino]benzoic acid | C21 H24 Cl N O4 | 390 | (M + H) |
| 470 | 3-[(2-Chlorophenyl)methoxy]-2-[(cyclohexylcarbonyl)amino]benzoic acid | C21 H22 Cl N O4 | 388 | (M + H) |
| 471 | 3-[(2-Chlorophenyl)methoxy]-2-[(2-quinoxalinylcarbonyl)amino]benzoic acid | C23 H16 Cl N3 O4 | 434 | (M + H) |
| 472 | 3-[(2-Chlorophenyl)methoxy]-2-[[(2-chloro-3-pyridinyl)carbonyl]amino]benzoic acid | C20 H14 Cl2 N2 O4 | 417 | (M + H) |
| 473 | 3-[(2-Chlorophenyl)methoxy]-2-[[(6-chloro-3-pyridinyl)carbonyl]amino]benzoic acid | C20 H14 Cl2 N2 O4 | 417 | (M + H) |

| Ex. | CAS Name | Elemental formula | Mass Spec, m/z | ion type inferred |
|---|---|---|---|---|
| 474 | 2-[(2-Chlorobenzoyl)amino]-3-[(2,4-dichlorophenyl)methoxy]benzoic acid | C21 H14 Cl3 N O4 | 450 | (M + H) |
| 475 | 3-[(2,4-Dichlorophenyl)methoxy]-2-[(2-methoxybenzoyl)amino]benzoic acid | C22 H17 Cl2 N O5 | 446 | (M + H) |
| 476 | 2-[(3-Chlorobenzoyl)amino]-3-[(2,4-dichlorophenyl)methoxy]benzoic acid | C21 H14 Cl3 N O4 | 450 | (M + H) |
| 477 | 3-[(2,4-Dichlorophenyl)methoxy]-2-[(3-methoxybenzoyl)amino]benzoic acid | C22 H17 Cl2 N O5 | 446 | (M + H) |
| 478 | 3-[(2,4-Dichlorophenyl)methoxy]-2-[(1-oxoheptyl)amino]benzoic acid | C21 H23 Cl2 N O4 | 424 | (M + H) |
| 479 | 3-[(2,4-Dichlorophenyl)methoxy]-2-[(cyclohexylcarbonyl)amino]benzoic acid | C21 H21 Cl2 N O4 | 423 | (M + H) |
| 480 | 3-[(2,4-Dichlorophenyl)methoxy]-2-[(phenylsulfonyl)amino]benzoic acid | C20 H15 Cl2 N O5 S | 452 | (M + H) |
| 481 | 2-[[(2-Chloro-3-pyridinyl)carbonyl]amino]-3-[(2,4-dichlorophenyl)methoxy]benzoic acid | C20 H13 Cl3 N2 O4 | 452 | (M + H) |
| 482 | 2-(Benzoylamino)-3-([1,1'-biphenyl]-4-ylmethoxy)benzoic acid | C27 H21 N O4 | 424 | (M + H) |
| 483 | 3-([1,1'-Biphenyl]-4-ylmethoxy)-2-[(2-chlorobenzoyl)amino]benzoic acid | C27 H20 Cl N O4 | 458 | (M + H) |
| 484 | 3-([1,1'-Biphenyl]-4-ylmethoxy)-2-[(2-methoxybenzoyl)amino]benzoic acid | C28 H23 N O5 | 454 | (M + H) |
| 485 | 3-([1,1'-Biphenyl]-4-ylmethoxy)-2-[(3-chlorobenzoyl)amino]benzoic acid | C27 H20 Cl N O4 | 458 | (M + H) |
| 486 | 3-([1,1'-Biphenyl]-4-ylmethoxy)-2-[(3-methoxybenzoyl)amino]benzoic acid | C28 H23 N O5 | 454 | (M + H) |
| 487 | 3-([1,1'-Biphenyl]-4-ylmethoxy)-2-[(1-oxoheptyl)amino]benzoic acid | C27 H29 N O4 | 432 | (M + H) |
| 488 | 3-([1,1'-Biphenyl]-4-ylmethoxy)-2-[(cyclohexylcarbonyl)amino]benzoic acid | C27 H27 N O4 | 430 | (M + H) |
| 489 | 3-([1,1'-Biphenyl]-4-ylmethoxy)-2-[(2-quinoxalinylcarbonyl)amino]benzoic acid | C29 H21 N3 O4 | 476 | (M + H) |
| 490 | 3-([1,1'-Biphenyl]-4-ylmethoxy)-2-[[(2-chloro-3-pyridinyl)carbonyl]amino]benzoic acid | C26 H19 Cl N2 O4 | 459 | (M + H) |

-continued

| Ex. | CAS Name | Elemental formula | Mass Spec, m/z | ion type inferred |
|---|---|---|---|---|
| 491 | 3-([1,1'-Biphenyl]-4-ylmethoxy)-2-[[(6-chloro-3-pyridinyl)carbonyl]amino]benzoic acid | C26 H19 Cl N2 O4 | 459 | (M + H) |
| 492 | 2-[(2-Chlorobenzoyl)amino]-3-(2-oxo-2-phenylethoxy)benzoic acid | C22 H16 Cl N O5 | 410 | (M + H) |
| 493 | 2-[(2-Methoxybenzoyl)amino]-3-(2-oxo-2-phenylethoxy)benzoic acid | C23 H19 N O6 | 406 | (M + H) |
| 494 | 2-(Benzoylamino)-3-butoxybenzoic acid | C18 H19 N O4 | 314 | (M + H) |
| 495 | 3-Butoxy-2-[(2-methoxybenzoyl)amino]benzoic acid | C19 H21 N O5 | 344 | (M + H) |
| 496 | 3-Butoxy-2-[(3-chorobenzoyl)amino]benzoic acid | C18 H18 Cl N O4 | 348 | (M + H) |
| 497 | 3-Butoxy-2-[(3-methoxybenzoyl)amino]benzoic acid | C19 H21 N O5 | 344 | (M + H) |
| 498 | 3-Butoxy-2-[(1-oxoheptyl)amino]benzoic acid | C18 H27 N O4 | 322 | (M + H) |
| 499 | 3-Butoxy-2-[(cyclohexylcarbonyl)amino]benzoic acid | C18 H25 N O4 | 320 | (M + H) |
| 500 | 3-Butoxy-2-[(2-quinoxalinylcarbonyl)amino]benzoic acid | C20 H19 N3 O4 | 366 | (M + H) |
| 501 | 3-Butoxy-2-[(phenylsulfonyl)amino]benzoic acid | C17 H19 N O5 S | 350 | (M + H) |
| 502 | 3-Butoxy-2-[[(2-chloro-3-pyridinyl)carbonyl]amino]benzoic acid | C17 H17 Cl N2 O4 | 349 | (M + H) |
| 503 | 3-Butoxy-2-[[(3-chlorophenyl)sulfonyl]amino]benzoic acid | C17 H18 Cl N O5 S | 384 | (M + H) |
| 504 | 3-Butoxy-2-[[(6-chloro-3-pyridinyl)carbonyl]amino]benzoic acid | C17 H17 Cl N2 O4 | 349 | (M + H) |
| 505 | 2-(Benzoylamino)-3-(cyclohexylmethoxy)benzoic acid | C21 H23 N O4 | 354 | (M + H) |
| 506 | 2-[(2-Chlorobenzoyl)amino]-3-(cyclohexylmethoxy)benzoic acid | C21 H22 Cl N O4 | 388 | (M + H) |
| 507 | 3-(Cyclohexylmethoxy)-2-[(2-methoxybenzoyl)amino]benzoic acid | C22 H25 N O5 | 384 | (M + H) |
| 508 | 2-[(3-Chlorobenzoyl)amino]-3-(cyclohexylmethoxy)benzoic acid | C21 H22 Cl N O4 | 388 | (M + H) |
| 509 | 3-(Cyclohexylmethoxy)-2-[(3-methoxybenzoyl)amino]benzoic acid | C22 H25 N O5 | 384 | (M + H) |
| 510 | 3-(Cyclohexylmethoxy)-2-[(1-oxoheptyl)amino]benzoic acid | C21 H31 N O4 | 362 | (M + H) |
| 511 | 2-[(Cyclohexylcarbonyl)amino]-3-(cyclohexylmethoxy)benzoic acid | C21 H29 N O4 | 360 | (M + H) |

| Ex. | CAS Name | Elemental formula | Mass Spec, m/z | ion type inferred |
|---|---|---|---|---|
| 512 | 3-(Cyclohexylmethoxy)-2-[(2-quinoxalinylcarbonyl)amino]benzoic acid | C23 H23 N3 O4 | 406 | (M + H) |
| 513 | 3-(Cyclohexylmethoxy)-2-[(phenylsulfonyl)amino]benzoic acid | C20 H23 N O5 S | 390 | (M + H) |
| 514 | 2-[[(2-Chloro-3-pyridinyl)carbonyl]amino]-3-(cyclohexylmethoxy)benzoic acid | C20 H21 Cl N2 O4 | 389 | (M + H) |
| 515 | 2-[[(3-Chlorophenyl)sulfonyl]amino]-3-(cyclohexylmethoxy)benzoic acid | C20 H22 Cl N O5 S | 424 | (M + H) |
| 516 | 2-[[(6-Chloro-3-pyridinyl)carbonyl]amino]-3-(cyclohexylmethoxy)benzoic acid | C20 H21 Cl N2 O4 | 389 | (M + H) |
| 517 | 2-(Benzoylamino)-3-(1-naphthalenylmethoxy)benzoic acid | C25 H19 N O4 | 398 | (M + H) |
| 518 | 2-[(2-Chlorobenzoyl)amino]-3-(1-naphthalenylmethoxy)benzoic acid | C25 H18 Cl N O4 | 432 | (M + H) |
| 519 | 2-[(2-Methoxybenzoyl)amino]-3-(1-naphthalenylmethoxy)benzoic acid | C26 H21 N O5 | 428 | (M + H) |
| 520 | 2-[(3-Chlorobenzoyl)amino]-3-(1-naphthalenylmethoxy)benzoic acid | C25 H18 Cl N O4 | 432 | (M + H) |
| 521 | 2-[(3-Methoxybenzoyl)amino]-3-(1-naphthalenylmethoxy)benzoic acid | C26 H21 N O5 | 428 | (M + H) |
| 522 | 3-(1-Naphthalenylmethoxy)-2-[(1-oxoheptyl)amino]benzoic acid | C25 H27 N O4 | 406 | (M + H) |
| 523 | 2-[(Cyclohexylcarbonyl)amino]-3-(1-naphthalenylmethoxy)benzoic acid | C25 H25 N O4 | 404 | (M + H) |
| 524 | 3-(1-Naphthalenylmethoxy)-2-[(2-quinoxalinylcarbonyl)amino]benzoic acid | C27 H19 N3 O4 | 450 | (M + H) |
| 525 | 2-[[(2-Chloro-3-pyridinyl)carbonyl]amino]-3-(1-naphthalenylmethoxy)benzoic acid | C24 H17 Cl N2 O4 | 433 | (M + H) |
| 526 | 2-[[(6-Chloro-3-pyridinyl)carbonyl]amino]-3-(1-naphthalenylmethoxy)benzoic acid | C24 H17 Cl N2 O4 | 433 | (M + H) |
| 527 | 2-(Benzoylamino)-3-(2-naphthalenylmethoxy)benzoic acid | C25 H19 N O4 | 398 | (M + H) |
| 528 | 2-[(2-Chlorobenzoyl)amino]-3-(2-naphthalenylmethoxy)benzoic acid | C25 H18 Cl N O4 | 432 | (M + H) |

| Ex. | CAS Name | Elemental formula | Mass Spec, m/z | ion type inferred |
|---|---|---|---|---|
| 529 | 2-[(2-Methoxybenzoyl)amino]-3-(2-naphthalenylmethoxy)benzoic acid | C26 H21 N O5 | 428 | (M + H) |
| 530 | 2-[(3-Chlorobenzoyl)amino]-3-(2-naphthalenylmethoxy)benzoic acid | C25 H18 Cl N O4 | 432 | (M + H) |
| 531 | 2-[(3-Methoxybenzoyl)amino]-3-(2-naphthalenylmethoxy)benzoic acid | C26 H21 N O5 | 428 | (M + H) |
| 532 | 3-(2-Naphthalenylmethoxy)-2-[(1-oxoheptyl)amino]benzoic acid | C25 H27 N O4 | 406 | (M + H) |
| 533 | 2-[(Cyclohexylcarbonyl)amino]-3-(2-naphthalenylmethoxy)benzoic acid | C25 H25 N O4 | 404 | (M + H) |
| 534 | 3-(2-Naphthalenylmethoxy)-2-[(2-quinoxalinylcarbonyl)amino]benzoic acid | C27 H19 N3 O4 | 450 | (M + H) |
| 535 | 2-[[(2-Chloro-3-pyridinyl)carbonyl]amino]-3-(2-naphthalenylmethoxy)benzoic acid | C24 H17 Cl N2 O4 | 433 | (M + H) |
| 536 | 2-[[(6-Chloro-3-pyridinyl)carbonyl]amino]-3-(2-naphthalenylmethoxy)benzoic acid | C24 H17 Cl N2 O4 | 433 | (M + H) |
| 537 | 2-[(2-Chlorobenzoyl)amino]-3-[(4-chlorophenyl)methoxy]benzoic acid | C21 H15 Cl2 N O4 | 416 | (M + H) |
| 538 | 3-[(4-Chlorophenyl)methoxy]-2-[(2-methoxybenzoyl)amino]benzoic acid | C22 H18 Cl N O5 | 412 | (M + H) |
| 539 | 2-[(3-Chlorobenzoyl)amino]-3-[(4-chlorophenyl)methoxy]benzoic acid | C21 H15 Cl2 N O4 | 416 | (M + H) |
| 540 | 3-[(4-Chlorophenyl)methoxy]-2-[(3-methoxybenzoyl)amino]benzoic acid | C22 H18 Cl N O5 | 412 | (M + H) |
| 541 | 3-[(4-Chlorophenyl)methoxy]-2-[(1-oxoheptyl)amino]benzoic acid | C21 H24 Cl N O4 | 390 | (M + H) |
| 542 | 3-[(4-Chlorophenyl)methoxy]-2-[(cyclohexylcarbonyl)amino]benzoic acid | C21 H22 Cl N O4 | 388 | (M + H) |
| 543 | 3-[(4-Chlorophenyl)methoxy]-2-[(2-quinoxalinylcarbonyl)amino]benzoic acid | C23 H16 Cl N3 O4 | 434 | (M + H) |

| Ex. | CAS Name | Elemental formula | Mass Spec, m/z | ion type inferred |
|---|---|---|---|---|
| 544 | 3-[(4-Chlorophenyl)methoxy]-2-[[(2-chloro-3-pyridinyl)carbonyl]amino]benzoic acid | C20 H14 Cl2 N2 O4 | 417 | (M + H) |
| 545 | 3-[(4-Chlorophenyl)methoxy]-2-[[(6-chloro-3-pyridinyl)carbonyl]amino]benzoic acid | C20 H14 Cl2 N2 O4 | 417 | (M + H) |
| 546 | 2-(Benzoylamino)-3-[(3-phenoxyphenyl)methoxy]benzoic acid | C27 H21 N O5 | 440 | (M + H) |
| 547 | 2-[(2-Chlorobenzoyl)amino]-3-[(3-phenoxyphenyl)methoxy]benzoic acid | C27 H20 Cl N O5 | 474 | (M + H) |
| 548 | 2-[(2-Methoxybenzoyl)amino]-3-[(3-phenoxyphenyl)methoxy]benzoic acid | C28 H23 N O6 | 470 | (M + H) |
| 549 | 2-[(3-Chlorobenzoyl)amino]-3-[(3-phenoxyphenyl)methoxy]benzoic acid | C27 H20 Cl N O5 | 474 | (M + H) |
| 550 | 2-[(3-Methoxybenzoyl)amino]-3-[(3-phenoxyphenyl)methoxy]benzoic acid | C28 H23 N O6 | 470 | (M + H) |
| 551 | 2-[(1-Oxoheptyl)amino]-3-[(3-phenoxyphenyl)methoxy]benzoic acid | C27 H29 N O5 | 448 | (M + H) |
| 552 | 2-[(Cyclohexylcarbonyl)amino]-3-[(3-phenoxyphenyl)methoxy]benzoic acid | C27 H27 N O5 | 446 | (M + H) |
| 553 | 3-[(3-Phenoxyphenyl)methoxy]-2-[(2-quinoxalinylcarbonyl)amino]benzoic acid | C29 H21 N3 O5 | 492 | (M + H) |
| 554 | 2-[[(2-Chloro-3-pyridinyl)carbonyl]amino]-3-[(3-phenoxyphenyl)methoxy]benzoic acid | C26 H19 Cl N2 O5 | 475 | (M + H) |
| 555 | 2-[[(6-Chloro-3-pyridinyl)carbonyl]amino]-3-[(3-phenoxyphenyl)methoxy]benzoic acid | C26 H19 Cl N2 O5 | 475 | (M + H) |
| 556 | 2-(Benzoylamino)-3-[(3-methoxyphenyl)methoxy]benzoic acid | C22 H19 N O5 | 378 | (M + H) |
| 557 | 2-[(2-Chlorobenzoyl)amino]-3-[(3-methoxyphenyl)methoxy]benzoic acid | C22 H18 Cl N O5 | 412 | (M + H) |
| 558 | 2-[(2-Methoxybenzoyl)amino]-3-[(3-methoxyphenyl)methoxy]benzoic acid | C23 H21 N O6 | 408 | (M + H) |
| 559 | 2-[(3-Chlorobenzoyl)amino]-3-[(3-methoxyphenyl)methoxy]benzoic acid | C22 H18 Cl N O5 | 412 | (M + H) |
| 560 | 3-[(3-Methoxyphenyl)methoxy]-2-[(1-oxoheptyl)amino]benzoic acid | C22 H27 N O5 | 386 | (M + H) |

| Ex. | CAS Name | Elemental formula | Mass Spec, m/z | ion type inferred |
|---|---|---|---|---|
| 561 | 2-[(Cyclohexylcarbonyl)amino]-3-[(3-methoxyphenyl)methoxy]benzoic acid | C22 H25 N O5 | 384 | (M + H) |
| 562 | 3-[(3-Methoxyphenyl)methoxy]-2-[(2-quinoxalinylcarbonyl)amino]benzoic acid | C24 H19 N3 O5 | 430 | (M + H) |
| 563 | 3-[(3-Methoxyphenyl)methoxy]-2-[(phenylsulfonyl)amino]benzoic acid | C21 H19 N O6 S | 414 | (M + H) |
| 564 | 2-[[(2-Chloro-3-pyridinyl)carbonyl]amino]-3-[(3-methoxyphenyl)methoxy]benzoic acid | C21 H17 Cl N2 O5 | 413 | (M + H) |
| 565 | 2-[[(6-Chloro-3-pyridinyl)carbonyl]amino]-3-[(3-methoxyphenyl)methoxy]benzoic acid | C21 H17 Cl N2 O5 | 413 | (M + H) |
| 566 | 2-(Benzoylamino)-3-(phenylmethoxy)benzoic acid | C21 H17 N O4 | 348 | (M + H) |
| 567 | 2-[(3-Chlorobenzoyl)amino]-3-(phenylmethoxy)benzoic acid | C21 H16 Cl N O4 | 382 | (M + H) |
| 568 | 2-(Benzoylamino)-3-[(2-chlorophenyl)methoxy]benzoic acid | C21 H16 Cl N O4 | 382 | (M + H) |
| 569 | 2-[(2-Chlorobenzoyl)amino]-3-[(2-chlorophenyl)methoxy]benzoic acid | C21 H15 Cl2 N O4 | 416 | (M + H) |
| 570 | 2-(Benzoylamino)-3-[(2,4-dichlorophenyl)methoxy]benzoic acid | C21 H15 Cl2 N O4 | 416 | (M + H) |
| 571 | 2-(Benzoylamino)-3-[(4-chlorophenyl)methoxy]benzoic acid | C21 H16 Cl N O4 | 382 | (M + H) |

EXAMPLES 572–728

The title compounds were prepared as part of a solid-phase library run employing the method of Examples 394–571, but using 2-hydroxy-3-nitrobenzoic acid instead of 3-hydroxy-2-nitrobenzoic acid.

| Ex. | CAS Name | Elemental formula | Mass Spec, m/z | ion type inferred |
|---|---|---|---|---|
| 572 | 3-[(2-Bromobenzoyl)amino]-2-[(2-chlorophenyl)methoxy]benzoic acid | C21 H15 Br Cl N O4 | 460 | [M + H] |
| 573 | 2-[(2-Chlorophenyl)methoxy]-3-[(2-fluorobenzoyl)amino]benzoic acid | C21 H15 Cl F N O4 | 400 | [M + H] |

| Ex. | CAS Name | Elemental formula | Mass Spec, m/z | ion type inferred |
|---|---|---|---|---|
| 574 | 2-[(2-Chlorophenyl)methoxy]-3-[(2,4-difluorobenzoyl)amino]benzoic acid | C21 H14 Cl F2 N O4 | 418 | [M + H] |
| 575 | 2-[(2-Chlorophenyl)methoxy]-3-[(2-methoxybenzoyl)amino]benzoic acid | C22 H18 Cl N O5 | 412 | [M + H] |
| 576 | 2-[(2-Chlorophenyl)methoxy]-3-[(2-methylbenzoyl)amino]benzoic acid | C22 H18 Cl N O4 | 396 | [M + H] |
| 577 | 3-[(3-Bromobenzoyl)amino]-2-[(2-chlorophenyl)methoxy]benzoic acid | C21 H15 Br Cl N O4 | 461 | [M + H] |
| 578 | 2-[(2-Chlorophenyl)methoxy]-3-[(3-fluorobenzoyl)amino]benzoic acid | C21 H15 Cl F N O4 | 401 | [M + H] |
| 579 | 3-[(3-Chlorobenzoyl)amino]-2-[(2-chlorophenyl)methoxy]benzoic acid | C21 H15 Cl2 N O4 | 416 | [M + H] |
| 580 | 2-[(2-Chlorophenyl)methoxy]-3-[(3-methoxybenzoyl)amino]benzoic acid | C22 H18 Cl N O5 | 412 | [M + H] |
| 581 | 2-[(2-Chlorophenyl)methoxy]-3-[(3-methylbenzoyl)amino]benzoic acid | C22 H18 Cl N O4 | 396 | [M + H] |
| 582 | 2-[(2-Chlorophenyl)methoxy]-3-[(4-fluorobenzoyl)amino]benzoic acid | C21 H15 Cl F N O4 | 400 | [M + H] |
| 583 | 3-[(4-Chlorobenzoyl)amino]-2-[(2-chlorophenyl)methoxy]benzoic acid | C21 H15 Cl2 N O4 | 416 | [M + H] |
| 584 | 2-[(2-Chlorophenyl)methoxy]-3-[(4-methoxybenzoyl)amino]benzoic acid | C22 H18 Cl N O5 | 412 | [M + H] |
| 585 | 3-[(4-Butoxybenzoyl)amino]-2-[(2-chlorophenyl)methoxy]benzoic acid | C25 H24 Cl N O5 | 454 | [M + H] |
| 586 | 3-[([1,1'-Biphenyl]-4-ylcarbonyl)amino]-2-[(2-chlorophenyl)methoxy]benzoic acid | C27 H20 Cl N O4 | 458 | [M + H] |
| 587 | 2-[(2-Chlorophenyl)methoxy]-3-[[4-(trifluoromethyl)benzoyl]amino]benzoic acid | C22 H15 Cl F3 N O4 | 450 | [M + H] |
| 588 | 2-[(2-Chlorophenyl)methoxy]-3-[(4-methylbenzoyl)amino]benzoic acid | C22 H18 Cl N O4 | 396 | [M + H] |
| 589 | 2-[(2-Chlorophenyl)methoxy]-3-[(4-propylbenzoyl)amino]benzoic acid | C24 H22 Cl N O4 | 424 | [M + H] |

-continued

| Ex. | CAS Name | Elemental formula | Mass Spec, m/z | ion type inferred |
|---|---|---|---|---|
| 590 | 2-[(2-Chlorophenyl)methoxy]-3-[(2-methyl-1-oxopropyl)amino]benzoic acid | C18 H18 Cl N O4 | 348 | [M + H] |
| 591 | 2-[(2-Chlorophenyl)methoxy]-3-[(phenoxyacetyl)amino]benzoic acid | C22 H18 Cl N O5 | 412 | [M + H] |
| 592 | 2-[(2-Chlorophenyl)methoxy]-3-[[(2E)-1-oxo-3-phenyl-2-propenyl]amino]benzoic acid | C23 H18 Cl N O4 | 408 | [M + H] |
| 593 | 2-[(2-Chlorophenyl)methoxy]-3-[(1-oxopropyl)amino]benzoic acid | C17 H16 Cl N O4 | 334 | [M + H] |
| 594 | 2-[(2-Chlorophenyl)methoxy]-3-[(1-oxo-3-phenylpropyl)amino]benzoic acid | C23 H20 Cl N O4 | 410 | [M + H] |
| 595 | 2-[(2-Chlorophenyl)methoxy]-3-[(1-oxoheptyl)amino]benzoic acid | C21 H24 Cl N O4 | 390 | [M + H] |
| 596 | 2-[(2-Chlorophenyl)methoxy]-3-[(4-iodobenzoyl)amino]benzoic acid | C21 H15 Cl I N O4 | 508 | [M + H] |
| 597 | 2-[(2-Chlorophenyl)methoxy]-3-[(cyclopropylcarbonyl)amino]benzoic acid | C18 H16 Cl N O4 | 346 | [M + H] |
| 598 | 2-[(2-Chlorophenyl)methoxy]-3-[(cyclopentylcarbonyl)amino]benzoic acid | C20 H20 Cl N O4 | 374 | [M + H] |
| 599 | 2-[(2-Chlorophenyl)methoxy]-3-[(3-cyclopentyl-1-oxopropyl)amino]benzoic acid | C22 H24 Cl N O4 | 402 | [M + H] |
| 600 | 2-[(2-Chlorophenyl)methoxy]-3-[(cyclohexylcarbonyl)amino]benzoic acid | C21 H22 Cl N O4 | 388 | [M + H] |
| 601 | 2-[(2-Chlorophenyl)methoxy]-3-[(2-furanylcarbonyl)amino]benzoic acid | C19 H14 Cl N O5 | 372 | [M + H] |
| 602 | 2-[(2-Chlorophenyl)methoxy]-3-[(2-thienylacetyl)amino]benzoic acid | C20 H16 Cl N O4 S | 402 | [M + H] |
| 603 | 2-[(2-Chlorophenyl)methoxy]-3-[(phenylsulfonyl)amino]benzoic acid | C20 H16 Cl N O5 S | 418 | [M + H] |
| 604 | 2-[(2-Chlorophenyl)methoxy]-3-[(4-pyridinylcarbonyl)amino]benzoic acid | C20 H15 Cl N2 O4 | 383 | [M + H] |
| 605 | 3-[(1,3-Benzodioxol-5-ylcarbonyl)amino]-2-[(2-chlorophenyl)methoxy]benzoic acid | C22 H16 Cl N O6 | 426 | [M + H] |
| 606 | 3-[(Benzo[b]thiophen-2-ylcarbonyl)amino]-2-[(2-chlorophenyl)methoxy]benzoic acid | C23 H16 Cl N O4 S | 434 | [M + H] |

| Ex. | CAS Name | Elemental formula | Mass Spec, m/z | ion type inferred |
|---|---|---|---|---|
| 607 | 2-[(2-Chlorophenyl)methoxy]-3-[[(2-chloro-3-pyridinyl)carbonyl]amino]benzoic acid | C20 H14 Cl2 N2 O4 | 417 | [M + H] |
| 608 | 2-[(2-Chlorophenyl)methoxy]-3-[[(3-chlorophenyl)sulfonyl]amino]benzoic acid | C20 H15 Cl2 N O5 S | 452 | [M + H] |
| 609 | 2-[(2-Chlorophenyl)methoxy]-3-[[(6-chloro-3-pyridinyl)carbonyl]amino]benzoic acid | C20 H14 Cl2 N2 O4 | 417 | [M + H] |
| 610 | 3-[[(3-Chlorobenzo[b]thiophen-2-yl)carbonyl]amino]-2-[(2-chlorophenyl)methoxy]benzoic acid | C23 H15 Cl2 N O4 S | 472 | [M + H] |
| 611 | 3-[[(5-Bromo-3-pyridinyl)carbonyl]amino]-2-[(2-chlorophenyl)methoxy]benzoic acid | C20 H14 Br Cl N2 O4 | 461 | [M + H] |
| 612 | 3-[[[3,5-Bis(methylthio)-4-isothiazolyl]carbonyl]amino]-2-[(2-chlorophenyl)methoxy]benzoic acid | C20 H17 Cl N2 O4 S3 | 481 | [M + H] |
| 613 | 2-[(2-Bromophenyl)methoxy]-3-[(2-fluorobenzoyl)amino]benzoic acid | C21 H15 Br F N O4 | 444 | [M + H] |
| 614 | 2-[(2-Bromophenyl)methoxy]-3-[(2,4-difluorobenzoyl)amino]benzoic acid | C21 H14 Br F2 N O4 | 462 | [M + H] |
| 615 | 2-[(2-Bromophenyl)methoxy]-3-[(2,4-dichlorobenzoyl)amino]benzoic acid | C21 H14 Br Cl2 N O4 | 494 | [M + H] |
| 616 | 2-[(2-Bromophenyl)methoxy]-3-[(2-methoxybenzoyl)amino]benzoic acid | C22 H18 Br N O5 | 456 | [M + H] |
| 617 | 2-[(2-Bromophenyl)methoxy]-3-[(2-methylbenzoyl)amino]benzoic acid | C22 H18 Br N O4 | 440 | [M + H] |
| 618 | 3-[(3-Bromobenzoyl)amino]-2-[(2-bromophenyl)methoxy]benzoic acid | C21 H15 Br2 N O4 | 504 | [M + H] |
| 619 | 2-[(2-Bromophenyl)methoxy]-3-[(3-fluorobenzoyl)amino]benzoic acid | C21 H15 Br F N O4 | 444 | [M + H] |
| 620 | 2-[(2-Bromophenyl)methoxy]-3-[(3-chlorobenzoyl)amino]benzoic acid | C21 H15 Br Cl N O4 | 460 | [M + H] |
| 621 | 2-[(2-Bromophenyl)methoxy]-3-[(3-methoxybenzoyl)amino]benzoic acid | C22 H18 Br N O5 | 456 | [M + H] |

| Ex. | CAS Name | Elemental formula | Mass Spec, m/z | ion type inferred |
|---|---|---|---|---|
| 622 | 2-[(2-Bromophenyl)methoxy]-3-[(3-methylbenzoyl)amino]benzoic acid | C22 H18 Br N O4 | 440 | [M + H] |
| 623 | 2-[(2-Bromophenyl)methoxy]-3-[(4-fluorobenzoyl)amino]benzoic acid | C21 H15 Br F N O4 | 444 | [M + H] |
| 624 | 2-[(2-Bromophenyl)methoxy]-3-[(4-chlorobenzoyl)amino]benzoic acid | C21 H15 Br Cl N O4 | 460 | [M + H] |
| 625 | 2-[(2-Bromophenyl)methoxy]-3-[(4-methoxybenzoyl)amino]benzoic acid | C22 H18 Br N O5 | 456 | [M + H] |
| 626 | 2-[(2-Bromophenyl)methoxy]-3-[(4-butoxybenzoyl)amino]benzoic acid | C25 H24 Br N O5 | 498 | [M + H] |
| 627 | 3-[([1,1'-Biphenyl]-4-ylcarbonyl)amino]-2-[(2-bromophenyl)methoxy]benzoic acid | C27 H20 Br N O4 | 502 | [M + H] |
| 628 | 2-[(2-Bromophenyl)methoxy]-3-[[4-(trifluoromethyl)benzoyl]amino]benzoic acid | C22 H15 Br F3 N O4 | 494 | [M + H] |
| 629 | 2-[(2-Bromophenyl)methoxy]-3-[(4-methylbenzoyl)amino]benzoic acid | C22 H18 Br N O4 | 440 | [M + H] |
| 630 | 2-[(2-Bromophenyl)methoxy]-3-[(4-propylbenzoyl)amino]benzoic acid | C24 H22 Br N O4 | 468 | [M + H] |
| 631 | 2-[(2-Bromophenyl)methoxy]-3-[(2-methyl-1-oxopropyl)amino]benzoic acid | C18 H18 Br N O4 | 392 | [M + H] |
| 632 | 2-[(2-Bromophenyl)methoxy]-3-[(phenoxyacetyl)amino]benzoic acid | C22 H18 Br N O5 | 456 | [M + H] |
| 633 | 2-[(2-Bromophenyl)methoxy]-3-[[(2E)-1-oxo-3-phenyl-2-propenyl]amino]benzoic acid | C23 H18 Br N O4 | 452 | [M + H] |
| 634 | 2-[(2-Bromophenyl)methoxy]-3-[(3-ethoxy-1,3-dioxopropyl)amino]benzoic acid | C19 H18 Br N O6 | 436 | [M + H] |
| 635 | 2-[(2-Bromophenyl)methoxy]-3-[(1-oxopropyl)amino]benzoic acid | C17 H16 Br N O4 | 378 | [M + H] |
| 636 | 2-[(2-Bromophenyl)methoxy]-3-[(1-oxo-3-phenylpropyl)amino]benzoic acid | C23 H20 Br N O4 | 454 | [M + H] |
| 637 | 2-[(2-Bromophenyl)methoxy]-3-[(1-oxoheptyl)amino]benzoic acid | C21 H24 Br N O4 | 434 | [M + H] |

-continued

| Ex. | CAS Name | Elemental formula | Mass Spec, m/z | ion type inferred |
|---|---|---|---|---|
| 638 | 2-[(2-Bromophenyl)methoxy]-3-[(4-iodobenzoyl)amino]benzoic acid | C21 H15 Br I N O4 | 552 | [M + H] |
| 639 | 2-[(2-Bromophenyl)methoxy]-3-[(cyclopentylcarbonyl)amino]benzoic acid | C20 H20 Br N O4 | 418 | [M + H] |
| 640 | 2-[(2-Bromophenyl)methoxy]-3-[(3-cyclopentyl-1-oxopropyl)amino]benzoic acid | C22 H24 Br N O4 | 446 | [M + H] |
| 641 | 2-[(2-Bromophenyl)methoxy]-3-[(cyclohexylcarbonyl)amino]benzoic acid | C21 H22 Br N O4 | 432 | [M + H] |
| 642 | 2-[(2-Bromophenyl)methoxy]-3-[(2-furanylcarbonyl)amino]benzoic acid | C19 H14 Br N O5 | 416 | [M + H] |
| 643 | 2-[(2-Bromophenyl)methoxy]-3-[(2-thienylacetyl)amino]benzoic acid | C20 H16 Br N O4 S | 446 | [M + H] |
| 644 | 2-[(2-Bromophenyl)methoxy]-3-[(phenylsulfonyl)amino]benzoic acid | C20 H16 Br N O5 S | 462 | [M + H] |
| 645 | 2-[(2-Bromophenyl)methoxy]-3-[[(3-methoxyphenyl)acetyl]amino]benzoic acid | C23 H20 Br N O5 | 470 | [M + H] |
| 646 | 2-[(2-Bromophenyl)methoxy]-3-[(3-pyridinylcarbonyl)amino]benzoic acid | C20 H15 Br N2 O4 | 427 | [M + H] |
| 647 | 2-[(2-Bromophenyl)methoxy]-3-[(4-pyridinylcarbonyl)amino]benzoic acid | C20 H15 Br N2 O4 | 427 | [M + H] |
| 648 | 3-[(1,3-Benzodioxol-5-ylcarbonyl)amino]-2-[(2-bromophenyl)methoxy]benzoic acid | C22 H16 Br N O6 | 470 | [M + H] |
| 649 | 3-[(Benzo[b]thiophen-2-ylcarbonyl)amino]-2-[(2-bromophenyl)methoxy]benzoic acid | C23 H16 Br N O4 S | 482 | [M + H] |
| 650 | 2-[(2-Bromophenyl)methoxy]-3-[[(3-chlorophenyl)sulfonyl]amino]benzoic acid | C20 H15 Br Cl N O5 S | 496 | [M + H] |
| 651 | 2-[(2-Bromophenyl)methoxy]-3-[[(5-bromo-3-pyridinyl)carbonyl]amino]benzoic acid | C20 H14 Br2 N2 O4 | 505 | [M + H] |
| 652 | 3-[(2-Bromobenzoyl)amino]-2-[(4-bromophenyl)methoxy]benzoic acid | C21 H15 Br2 N O4 | 504 | [M + H] |
| 653 | 2-[(4-Bromophenyl)methoxy]-3-[(2-methoxybenzoyl)amino]benzoic acid | C22 H18 Br N O5 | 456 | [M + H] |

| Ex. | CAS Name | Elemental formula | Mass Spec, m/z | ion type inferred |
|---|---|---|---|---|
| 654 | 2-[(4-Bromophenyl)methoxy]-3-[(2-methylbenzoyl)amino]benzoic acid | C22 H18 Br N O4 | 440 | [M + H] |
| 655 | 3-[(3-Bromobenzoyl)amino]-2-[(4-bromophenyl)methoxy]benzoic acid | C21 H15 Br2 N O4 | 504 | [M + H] |
| 656 | 2-[(4-Bromophenyl)methoxy]-3-[(3-chlorobenzoyl)amino]benzoic acid | C21 H15 Br Cl N O4 | 460 | [M + H] |
| 657 | 2-[(4-Bromophenyl)methoxy]-3-[(3-methoxybenzoyl)amino]benzoic acid | C22 H18 Br N O5 | 456 | [M + H] |
| 658 | 2-[(4-Bromophenyl)methoxy]-3-[(3-methylbenzoyl)amino]benzoic acid | C22 H18 Br N O4 | 440 | [M + H] |
| 659 | 3-[(4-Bromobenzoyl)amino]-2-[(4-bromophenyl)methoxy]benzoic acid | C21 H15 Br2 N O4 | 504 | [M + H] |
| 660 | 2-[(4-Bromophenyl)methoxy]-3-[(4-fluorobenzoyl)amino]benzoic acid | C21 H15 Br F N O4 | 444 | [M + H] |
| 661 | 2-[(4-Bromophenyl)methoxy]-3-[(4-chlorobenzoyl)amino]benzoic acid | C21 H15 Br Cl N O4 | 460 | [M + H] |
| 662 | 2-[(4-Bromophenyl)methoxy]-3-[(4-methoxybenzoyl)amino]benzoic acid | C22 H18 Br N O5 | 456 | [M + H] |
| 663 | 2-[(4-Bromophenyl)methoxy]-3-[(4-butoxybenzoyl)amino]benzoic acid | C25 H24 Br N O5 | 498 | [M + H] |
| 664 | 2-[(4-Bromophenyl)methoxy]-3-[(4-methylbenzoyl)amino]benzoic acid | C22 H18 Br N O4 | 440 | [M + H] |
| 665 | 2-[(4-Bromophenyl)methoxy]-3-[(4-propylbenzoyl)amino]benzoic acid | C24 H22 Br N O4 | 468 | [M + H] |
| 666 | 2-[(4-Bromophenyl)methoxy]-3-[(phenoxyacetyl)amino]benzoic acid | C22 H18 Br N O5 | 456 | [M + H] |
| 667 | 2-[(4-Bromophenyl)methoxy]-3-[[(2E)-1-oxo-3-phenyl-2-propenyl]amino]benzoic acid | C23 H18 Br N O4 | 452 | [M + H] |
| 668 | 2-[(4-Bromophenyl)methoxy]-3-[(1-oxopropyl)amino]benzoic acid | C17 H16 Br N O4 | 378 | [M + H] |
| 669 | 2-[(4-Bromophenyl)methoxy]-3-[(1-oxo-3-phenylpropyl)amino]benzoic acid | C23 H20 Br N O4 | 454 | [M + H] |

-continued

| Ex. | CAS Name | Elemental formula | Mass Spec, m/z | ion type inferred |
|---|---|---|---|---|
| 670 | 2-[(4-Bromophenyl)methoxy]-3-[(1-oxoheptyl)amino]benzoic acid | C21 H24 Br N O4 | 434 | [M + H] |
| 671 | 2-[(4-Bromophenyl)methoxy]-3-[(cyclopentylcarbonyl)amino]benzoic acid | C20 H20 Br N O4 | 418 | [M + H] |
| 672 | 2-[(4-Bromophenyl)methoxy]-3-[(3-cyclopentyl-1-oxopropyl)amino]benzoic acid | C22 H24 Br N O4 | 446 | [M + H] |
| 673 | 2-[(4-Bromophenyl)methoxy]-3-[(cyclohexylcarbonyl)amino]benzoic acid | C21 H22 Br N O4 | 432 | [M + H] |
| 674 | 2-[(4-Bromophenyl)methoxy]-3-[(2-furanylcarbonyl)amino]benzoic acid | C19 H14 Br N O5 | 416 | [M + H] |
| 675 | 2-[(4-Bromophenyl)methoxy]-3-[(2-thienylacetyl)amino]benzoic acid | C20 H16 Br N O4 S | 446 | [M + H] |
| 676 | 2-[(4-Bromophenyl)methoxy]-3-[(phenylsulfonyl)amino]benzoic acid | C20 H16 Br N O5 S | 462 | [M + H] |
| 677 | 2-[(4-Bromophenyl)methoxy]-3-[(3-pyridinylcarbonyl)amino]benzoic acid | C20 H15 Br N2 O4 | 427 | [M + H] |
| 678 | 2-[(4-Bromophenyl)methoxy]-3-[(4-pyridinylcarbonyl)amino]benzoic acid | C20 H15 Br N2 O4 | 427 | [M + H] |
| 679 | 3-[(1,3-Benzodioxol-5-ylcarbonyl)amino]-2-[(4-bromophenyl)methoxy]benzoic acid | C22 H16 Br N O6 | 470 | [M + H] |
| 680 | 3-[(Benzo[b]thiophen-2-ylcarbonyl)amino]-2-[(4-bromophenyl)methoxy]benzoic acid | C23 H16 Br N O4 S | 482 | [M + H] |
| 681 | 2-[(4-Bromophenyl)methoxy]-3-[[(2-chloro-3-pyridinyl)carbonyl]amino]benzoic acid | C20 H14 Br Cl N2 O4 | 461 | [M + H] |
| 682 | 2-[(4-Bromophenyl)methoxy]-3-[[(3-chlorobenzo[b]thiophen-2-yl)carbonyl]amino]benzoic acid | C23 H15 Br Cl N O4 S | 516 | [M + H] |
| 683 | 3-[[[3,5-Bis(methylthio)-4-isothiazolyl]carbonyl]amino]-2-[(4-bromophenyl)methoxy]benzoic acid | C20 H17 Br N2 O4 S3 | 525 | [M + H] |
| 684 | 3-[(2-Bromobenzoyl)amino]-2-(cyclohexylmethoxy)benzoic acid | C21 H22 Br N O4 | 432 | [M + H] |
| 685 | 2-(Cyclohexylmethoxy)-3-[(2,4-difluorobenzoyl)amino]benzoic acid | C21 H21 F2 N O4 | 390 | [M + H] |
| 686 | 3-[(2-Chlorobenzoyl)amino]-2-(cyclohexylmethoxy)benzoic acid | C21 H22 Cl N O4 | 388 | [M + H] |

| Ex. | CAS Name | Elemental formula | Mass Spec, m/z | ion type inferred |
|---|---|---|---|---|
| 687 | 2-(Cyclohexylmethoxy)-3-[(2,4-dichlorobenzoyl)amino]benzoic acid | C21 H21 Cl2 N O4 | 422 | [M + H] |
| 688 | 2-(Cyclohexylmethoxy)-3-[(2-methoxybenzoyl)amino]benzoic acid | C22 H25 N O5 | 384 | [M + H] |
| 689 | 2-(Cyclohexylmethoxy)-3-[(2-methylbenzoyl)amino]benzoic acid | C22 H25 N O4 | 368 | [M + H] |
| 690 | 3-[(3-Bromobenzoyl)amino]-2-(cyclohexylmethoxy)benzoic acid | C21 H22 Br N O4 | 432 | [M + H] |
| 691 | 2-(Cyclohexylmethoxy)-3-[(3-fluorobenzoyl)amino]benzoic acid | C21 H22 F N O4 | 372 | [M + H] |
| 692 | 3-[(3-Chlorobenzoyl)amino]-2-(cyclohexylmethoxy)benzoic acid | C21 H22 Cl N O4 | 388 | [M + H] |
| 693 | 2-(Cyclohexylmethoxy)-3-[(3-methoxybenzoyl)amino]benzoic acid | C22 H25 N O5 | 384 | [M + H] |
| 694 | 2-(Cyclohexylmethoxy)-3-[(3-methylbenzoyl)amino]benzoic acid | C22 H25 N O4 | 368 | [M + H] |
| 695 | 3-[(4-Bromobenzoyl)amino]-2-(cyclohexylmethoxy)benzoic acid | C21 H22 Br N O4 | 432 | [M + H] |
| 696 | 2-(Cyclohexylmethoxy)-3-[(4-fluorobenzoyl)amino]benzoic acid | C21 H22 F N O4 | 372 | [M + H] |
| 697 | 3-[(4-Chlorobenzoyl)amino]-2-(cyclohexylmethoxy)benzoic acid | C21 H22 Cl N O4 | 388 | [M + H] |
| 698 | 2-(Cyclohexylmethoxy)-3-[(4-methoxybenzoyl)amino]benzoic acid | C22 H25 N O5 | 384 | [M + H] |
| 699 | 3-[(4-Butoxybenzoyl)amino]-2-(cyclohexylmethoxy)benzoic acid | C25 H31 N O5 | 426 | [M + H] |
| 700 | 3-[([1,1'-Biphenyl]-4-ylcarbonyl)amino]-2-(cyclohexylmethoxy)benzoic acid | C27 H27 N O4 | 430 | [M + H] |
| 701 | 2-(Cyclohexylmethoxy)-3-[[4-(trifluoromethyl)benzoyl]amino]benzoic acid | C22 H22 F3 N O4 | 422 | [M + H] |
| 702 | 2-(Cyclohexylmethoxy)-3-[(4-methylbenzoyl)amino]benzoic acid | C22 H25 N O4 | 368 | [M + H] |
| 703 | 2-(Cyclohexylmethoxy)-3-[(4-propylbenzoyl)amino]benzoic acid | C24 H29 N O4 | 396 | [M + H] |
| 704 | 2-(Cyclohexylmethoxy)-3-[(1-oxo-2-methylpropyl)amino]benzoic acid | C18 H25 N O4 | 320 | [M + H] |
| 705 | 2-(Cyclohexylmethoxy)-3-[(phenoxyacetyl)amino]benzoic acid | C22 H25 N O5 | 384 | [M + H] |
| 706 | 2-(Cyclohexylmethoxy)-3-[[(2E)-1-oxo-3-phenyl-2-propenyl]amino]benzoic acid | C23 H25 N O4 | 380 | [M + H] |

-continued

| Ex. | CAS Name | Elemental formula | Mass Spec, m/z | ion type inferred |
|---|---|---|---|---|
| 707 | 2-(Cyclohexylmethoxy)-3-[(1-oxopropyl)amino]benzoic acid | C17 H23 N O4 | 306 | [M + H] |
| 708 | 2-(Cyclohexylmethoxy)-3-[(1-oxo-3-phenylpropyl)amino]benzoic acid | C23 H27 N O4 | 382 | [M + H] |
| 709 | 2-(Cyclohexylmethoxy)-3-[(1-oxoheptyl)amino]benzoic acid | C21 H31 N O4 | 362 | [M + H] |
| 710 | 2-(Cyclohexylmethoxy)-3-[(cyclopropylcarbonyl)amino]benzoic acid | C18 H23 N O4 | 318 | [M + H] |
| 711 | 2-(Cyclohexylmethoxy)-3-[(cyclopentylcarbonyl)amino]benzoic acid | C20 H27 N O4 | 346 | [M + H] |
| 712 | 2-(Cyclohexylmethoxy)-3-[(3-cyclopentyl-1-oxopropyl)amino]benzoic acid | C22 H31 N O4 | 374 | [M + H] |
| 713 | 3-[(Cyclohexylcarbonyl)amino]-2-(cyclohexylmethoxy)benzoic acid | C21 H29 N O4 | 360 | [M + H] |
| 714 | 2-(Cyclohexylmethoxy)-3-[(2-furanylcarbonyl)amino]benzoic acid | C19 H21 N O5 | 344 | [M + H] |
| 715 | 2-(Cyclohexylmethoxy)-3-[(2-thienylacetyl)amino]benzoic acid | C20 H23 N O4 S | 374 | [M + H] |
| 716 | 2-(Cyclohexylmethoxy)-3-(phenylsulfonyl)amino]benzoic acid | C20 H23 N O5 S | 390 | [M + H] |
| 717 | 2-(Cyclohexylmethoxy)-3-[[(3-methoxyphenyl)acetyl]amino]benzoic acid | C23 H27 N O5 | 398 | [M + H] |
| 718 | 2-(Cyclohexylmethoxy)-3-[(3-pyridinylcarbonyl)amino]benzoic acid | C20 H22 N2 O4 | 355 | [M + H] |
| 719 | 2-(Cyclohexylmethoxy)-3-[(4-pyridinylcarbonyl)amino]benzoic acid | C20 H22 N2 O4 | 355 | [M + H] |
| 720 | 3-[(1,3-Benzodioxol-5-ylcarbonyl)amino]-2-(cyclohexylmethoxy)benzoic acid | C22 H23 N O6 | 398 | [M + H] |
| 721 | 3-[(Benzo[b]thiophen-2-ylcarbonyl)amino]-2-(cyclohexylmethoxy)benzoic acid | C23 H23 N O4 S | 410 | [M + H] |
| 722 | 3-[[(2-Chloro-3-pyridinyl)carbonyl]amino]-2-(cyclohexylmethoxy)benzoic acid | C20 H21 Cl N2 O4 | 389 | [M + H] |
| 723 | 3-[[(3-Chlorophenyl)sulfonyl]amino]-2-(cyclohexylmethoxy)benzoic acid | C20 H22 Cl N O5 S | 424 | [M + H] |
| 724 | 3-[[(6-Chloro-3-pyridinyl)carbonyl]amino]-2-(cyclohexylmethoxy)benzoic acid | C20 H21 Cl N2 O4 | 389 | [M + H] |
| 725 | 3-[[(5-Bromo-3-pyridinyl)carbonyl]amino]-2-(cyclohexylmethoxy)benzoic acid | C20 H21 Br N2 O4 | 433 | [M + H] |

-continued

| Ex. | CAS Name | Elemental formula | Mass Spec, m/z | ion type inferred |
|---|---|---|---|---|
| 726 | 3-(Benzoylamino)-2-[(2-bromophenyl)methoxy] benzoic acid | C21 H16 Br N O4 | 426 | [M + H] |
| 727 | 3-(Benzoylamino)-2-[(2-chlorophenyl)methoxy] benzoic acid | C21 H16 Cl N O4 | 382 | [M + H] |
| 728 | 3-(Benzoylamino)-2-(cyclohexylmethoxy) benzoic acid | C21 H23 N O4 | 354 | [M + H] |

What is claimed is:

1. A compound of the following formula I

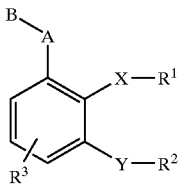

or pharmaceutically acceptable salts thereof, or prodrug esters thereof, or stereoisomers thereof, or solvates thereof wherein A is
    a bond;
    a $C_1$–$C_3$ alkylene group optionally independently substituted on available atoms with one to six halo, hydroxy, alkoxy, hydroxyalkyl, $SR^4$, alkyl, alkenyl, cyano, $CONHR^4$, $COOR^4$, oxo, $NHOR^4$, $=NOR^4$, or $N(R^8)COR^4$; or
    a $C_2$–$C_3$ alkenylene group optionally independently substituted on available atoms with one to four halo, hydroxy, alkoxy, hydroxyalkyl, $SR^4$, alkyl, alkenyl, cyano, $CONHR^4$, $COOR^4$, oxo, $NHOR^4$, $=NOR^4$, or $N(R^8)COR^4$;
    with the proviso that A is a bond only when $Z^{1a}$, $Z^{2a}$ and $Z^{3a}$ are independently halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl; and $Z^{1b}$, $Z^{2b}$ and $Z^{3b}$ are independently halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl;

B is carboxyl or tetrazole;

X and Y are independently
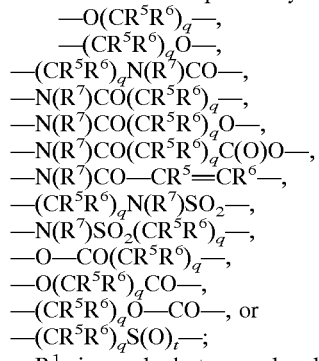

$R^1$ is aryl, heteroaryl, alkyl, cycloalkyl, aralkyl, heteroarylalkyl, cylcoalkenyl or heterocyclo any of which may be optionally substituted with $Z^{1a}$, $Z^{2a}$ and one or more $Z^{3a}$;

$R^2$ is aryl, heteroaryl, alkyl, cycloalkyl, aralkyl, heteroarylalkyl, cylcoalkenyl or heterocyclo any of which may be optionally substituted with $Z^{1b}$, $Z^{2b}$ and one or more $Z^{3b}$;

$R^3$ is H, OH, alkyl, hydroxyalkyl, aryl, nitro, halo, amino, alkylamino, alkoxy, cyano, thioalkyl, carboxyl, $COOR^4$, $NR^7COR^4$, or $NR^7COOR^4$;

$R^4$ is
  (1) H; or
  (2) alkyl, haloalkyl, aminoalkyl, alkoxyalkyl, hydroxyalkyl, aryl or heteroaryl any of which may be optionally substituted with $Z^{1c}$, $Z^{2c}$ and one or more $Z^{3c}$;

$R^5$ and $R^6$ are independently
  (1) H, OH, halo, cyano or oxo; or
  (2) alkoxy, alkyl, alkenyl, hydroxyalkyl, aryl, aralkyl, heteroaryl, heteroarylalkyl, alkylthio, aryloxy or heteroaryloxy any of which may be optionally substituted with $Z^{1d}$, $Z^{2d}$ and one more $Z^{3d}$;

$R^7$ is
  (1) H, OH, or cyano; or
  (2) alkoxy, alkyl, alkenyl, hydroxyalkyl, aryl, aralkyl, heteroaryl, heteroarylalkyl, alkylthio, aryloxy or heteroaryloxy any of which may be optionally substituted with $Z^{1e}$, $Z^{2e}$ and one more $Z^{3e}$;

$R^8$ is
  (1) H, OH; or
  (2) alkyl, aryl, heteroaryl, alkoxy, aryloxy, or alkenyl any of which may be optionally substituted with $Z^{1f}$, $Z^{2f}$ and one or more $Z^{3f}$;

t is 0, 1 or 2;

q is 0 to 5, $Z^{1a-1f}$, $Z^{2a-2f}$, and $Z^{3a-3f}$ are optional substituents independently selected from
  (1) V, where V is
    (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
    (ii) a group (i) which is itself substituted by one or more of the same or different groups (i); or
    (iii) a group (i) or (ii) which is independently substituted by one or more of the following groups (2) to (13) of the definition of $Z^{1a}$,
  (2) —OH or —OV,
  (3) —SH or —SV,
  (4) —C(O)$_p$H, —C(O)$_p$V, or —O—C(O)V, where p is 1 or 2, (5) —SO₃H, —S(O)ₚV, or —S(O)ₚN(V¹)V,
(6) halo,
(7) cyano,
(8) nitro,
(9) —U¹—NV²V³,
(10) —U¹—N(V¹)—U²—NV²V³,
(11) —U¹—N(V⁴)—U²—V,
(12) —U¹—N(V⁴)—U²—H,
(13) oxo;
U¹ and U² are each independently
(1) a single bond,
(2) —U³—S(O)ₚ—U⁴—,
(3) —U³—C(O)—U⁴—,
(4) —U³—C(S)—U⁴—,
(5) —U3—O—U⁴—,
(6) —U³—S—U⁴—,
(7) —U³—O—C(O)—U⁴—,
(8) —U³—C(O)—O—U⁴—,
(9) —U³—C(=NV¹ᵃ)—U⁴—, or
(10) —U³—C(O)—C(O)—U⁴—;
V¹,V¹ᵃ,V²,V³ and V⁴
(1) are each independently hydrogen or a group provided in the definition of $Z^{1a}$; or
(2) V² and V³ may together be alkylene or alkenylene, completing a 3- to 8-membered saturated or unsaturated ring together with the atoms to which they are attached, which ring is unsubstituted or substituted with one or more groups listed in the definition of $Z^{1a}$; or
(3) V² or V³, together with V¹, may be alkylene or alkenylene completing a 3- to 8-memberd saturated or unsaturated ring together with the nitrogen atoms to which they are attached, which ring is unsubstituted or substituted with one or more groups listed in the definition of $Z^{1a}$; or
(4) V² and V³ together with the nitrogen atom to which they are attached may combine to form a group —N=CV⁵V⁶ where V⁵ and V⁶ are each independently H or a group provided in the definition of V; and
U³ and U⁴ are each independently
(1) a single bond,
(2) alkylene,
(3) alkenylene, or
(4) alkynylene;
provided that said compound is other than a compound of formula X

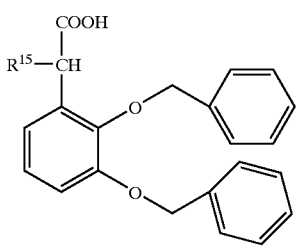

wherein
R¹⁵ is H, hydroxy or alkoxy.
2. A compound of claim 1 wherein
A is a bond, an optionally substituted $C_1$–$C_2$ alkylene group, or an optionally substituted $C_2$ alkenylene group;
X and Y are independently —O(CR⁵R⁶)_q—, —(CR⁵R⁶)_q O—, —N(R⁷)CO(CR⁵R⁶)_q O—, —N(R⁷)CO(CR⁵R⁶)_q —N(R⁷)CO(CR⁵R⁶)_qC(O)O—, —N(R⁷)CO—CR⁵=CR⁶—, —N(R⁷)SO₂(CR⁵R⁶)_q—, or —O(CR⁵R⁶)_qCO—
where
q is 0, 1 or 2;
R¹ is aryl, heteroaryl, cycloalkyl or alkyl, any of which may be optionally substituted with $Z^{1a}$, $Z^{2a}$ and one more $Z^{3a}$;
R² is aryl, heeteroaryl, cycloalkyl or alkyl, any of which be optionally substituted with $Z^{1b}$, $Z^{2b}$ and one more $Z^{3b}$;
R³ is H, OH, halo, alkyl, haloalkyl or hydroxyalkyl;
R⁵ and R⁶ are independently
(1) H or OH; or
(2) alkyl, aryl, aralkyl or heteroarylalkyl any of which may be optionally substituted with $Z^{1d}$, $Z^{2d}$ and one or more $Z^{3d}$; and
R⁷ is
(1) H or OH; or
(2) alkyl, aryl, aralkyl or heteroarylalkyl any of which may be optionally substituted with $Z^{1e}$, $Z^{2e}$ and one or more $Z^{3e}$.
3. A compound of claim 1 wherein B is carboxyl or an ester thereof.
4. A compound of claim 2 wherein
A is a bond, or a $C_1$–$C_2$ alkylene group optionally substituted with one OH, SH, NH², or NHOR⁴, or optionally substituted with at least one COOR⁴, halogen N(R⁸)COR⁴, hydroxyalkyl or oxo;
X and Y are independently —O(CR⁵R⁶)_q—, —(CR⁵R⁶)_q O—, —N R⁷)CO(CR⁵R⁶)_q— or —N(R⁷)SO₂(CR⁵ R⁶)_q—;
where
q is 0 or 1;
R¹ is aryl, heteroaryl or $C_3$–$C_6$ cycloalkyl any of which may be optionally substituted with one or more $Z^{1a}$, $Z^{2a}$ and one or more $Z^{3a}$;
R² is aryl, heteroaryl or $C_3$–$C_6$ cycloalkyl any of which may be optionally substituted with $Z^{1b}$, $Z^{2b}$ and one or more $Z^{3b}$;
R³ is H, OH, halo; alkyl, or haloalkyl;
R⁵ and R⁶ are independently
(1) H; or
(2) alkyl, aralkyl, or heteroarylalkyl any of which may be optionally substituted with $Z^{1d}$, $Z^{2d}$ and one or more $Z^{3d}$; and
R⁷ is
(1) H; or
(2) alkyl, aralkyl, or heteroarylalkyl any of which may be optionally substituted with $Z^{1d}$, $Z^{2d}$ and one or more $Z^{3d}$.
5. A compound of claim 4 wherein
R¹ is aryl or heteroaryl either of which may be optionally substituted with $Z^{1a}$, $Z^{2a}$ and one or more $Z^{3a}$; and
R² is aryl or heteroaryl either of which may be optionally substituted with $Z^{1b}$, $Z^{2b}$ and one or more $Z^{3ab}$.
6. A compound of claim 5 wherein
$Z^{1a}$, $Z^{2a}$ and $Z^{3a}$ are independently halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl; and
$Z^{1b}$, $Z^{2b}$ and $Z^{3b}$ are independently halogen, alkyl, alkoxy, alkylthio, haloalkyl, haloalkoxy, aryloxy, aralkoxy, aryl, arylcarbonyl, carboxyl, cyano, nitro, oxo, arylsulfonylalkyl or alkylsulfonyl.

7. A compound of claim 6 wherein B is carboxyl or an ester thereof.

8. A compound of claim 6 wherein $R^5$, $R^6$ and $R^7$ are independently H, alkyl, aralkyl, or heteroarylalkyl.

9. A compound of claim 8 wherein $R^5$ and $R^6$ are hydrogen; and $R^7$ is hydrogen, alkyl, or aralkyl.

10. A compound of claim 5 wherein $R^1$ is phenyl, napthyl, benzodioxolyl, benzodioxinyl, anthracenyl, pyridinyl, benzimidazolyl, quinoxalinyl, furanyl, thienyl, benzothiophenyl, or isothiozolyl any of which may be optionally substituted with $Z^{1a}$, $Z^{2a}$ and one or more $Z^{3a}$; and $R^2$ is phenyl, napthyl, benzodioxolyl, benzodioxinyl, anthracenyl, pyridinyl, benzimidazolyl, quinoxalinyl, furanyl, thienyl, benzothiophenyl, or isothiozolyl any of which may be optionally substituted with $Z^{1b}$, $Z^{2b}$ and one or more $Z^{3b}$.

11. A pharmaceutical composition comprising at least one compound of claim 1 and a pharmacuetically acceptable vehicle or carrier therefor.

12. The pharmaceutical composition of claim 11 further comprising at least one additional therapeutic agent selected from antidiabetic agents, antihyperglycemic agents, hypolipidemic agents, antiobesity agents, antihypertensive agents, antiplatelet agents, antiinfective agents, antiathersclerotic agents and anti-inflammatory agents.

13. The pharmaceutical composition of claim 12 wherein the other therapeutic agent is at least one antidiabetic agent selected from biguanides, sulfonyl ureas, glucosidase inhibitors, PPAR modulators, insulin sensitizers, glucagon-like peptide-1 (GLP-1), insulin or biguanide/glyburide combination.

14. The pharmaceutical composition of claim 13 wherein the antidiabetic agent is metformin, glyburide, glimepiride, glipyride, glipizide, chlorpropamide, gliclazide, acarbose, miglitol, troglitazone, rosiglitizone, piaglitazone, insulin, and/or metformin/glyburide combinations.

* * * * *